United States Patent [19]
Salituro et al.

[11] Patent Number: 5,519,048
[45] Date of Patent: May 21, 1996

[54] 3-(INDOL-3-YL)-PROPENOIC ACID DERIVATIVES AND PHARMACEUTICAL COMPOSITIONS THEREOF

[75] Inventors: Francesco G. Salituro, Marlborough, Mass.; Bruce M. Baron; Boyd L. Harrison, both of Cincinnati, Ohio; Philip L. Nyce, Millbury, Mass.

[73] Assignee: Merrell Pharmaceuticals Inc., Cincinnati, Ohio

[21] Appl. No.: 441,911

[22] Filed: May 16, 1995

Related U.S. Application Data

[63] Continuation-in-part of Ser. No. 331,419, Oct. 31, 1994, abandoned, which is a continuation-in-part of Ser. No. 190,814, Feb. 2, 1994, abandoned, which is a continuation-in-part of Ser. No. 139,323, Oct. 19, 1993, abandoned, which is a continuation of Ser. No. 68,367, May 27, 1993, abandoned.

[51] Int. Cl.$^6$ .............. A61K 31/40; C07D 209/12; C07D 401/06; C07D 413/06
[52] U.S. Cl. ............ 514/419; 514/231.5; 514/253; 544/143; 544/373; 548/492
[58] Field of Search .............. 548/492; 514/419, 514/231.5, 253; 544/143, 373

[56] References Cited

U.S. PATENT DOCUMENTS 5,106,847  4/1992  Salituro et al. .............. 514/232.5

FOREIGN PATENT DOCUMENTS

| 0568136 | 11/1993 | European Pat. Off. ...... C07D 209/42 |
| 92/16205 | 10/1992 | WIPO ........................ C07D 209/42 |
| 93/21153 | 4/1993 | WIPO ........................ C07D 209/40 |

OTHER PUBLICATIONS

Salituro F. G. et al, *Bioorganic & Medicinal Chem. Ltrs*, vol. 1, No. 9 pp. 455–460, 1991.
Kemp, John A. et al, *TiPS*—January (vol. 14) 1992.

*Primary Examiner*—Jacqueline Haley
*Attorney, Agent, or Firm*—Michael J. Sayles

[57] ABSTRACT

The present invention is new 3-(indol-3-yl)-propenoic acid derivatives and pharmaceutical compositions thereof. These new 3-indolyl-3-yl-prpopenoic acid derivatives are useful as NMDA antagonist.

65 Claims, No Drawings

3-(INDOL-3-YL)-PROPENOIC ACID DERIVATIVES AND PHARMACEUTICAL COMPOSITIONS THEREOF

This is a Continuation-in-part of application Ser. No. 08/331,419, filed Oct. 31, 1994 now abandoned; which is a Continuation-in-part of application Ser. No. 08/190,814, filed Feb. 2, 1994 now abandoned; which is a Continuation-in-part of application Ser. No. 08/139,323, filed Oct. 19, 1993, now abandoned; which is a 1.62 Con. of application Ser. No. 08/068,367, filed May 27, 1993, now abandoned.

The present invention is directed to a new class of excitatory amino acid antagonists. These new antagonists, 3-(indol-3-yl)-propenoic acid derivatives, are useful as NMDA (N-methyl-D-aspartate) antagonists. They preferentially bind to the strychnine-insensitive glycine binding site on the NMDA receptor complex associated with the treatment of a number of disease states. Another aspect of the invention is directed to their use in treatment of a number of diseases as well as to pharmaceutical compositions containing these excitatory amino acid antagonists.

In accordance with the present invention, a new class of NMDA antagonists have been discovered which can be described by the formula:

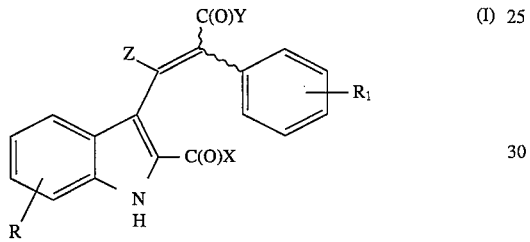

(I)

in which Z is represented by: hydrogen, —$CH_3$, or —$C_2H_5$; R is represented by from 1 to 3 substituents independently chosen from the group: hydrogen, $C_{1-4}$ alkyl, $C_{1-4}$ alkoxy, halogen, —$CF_3$, or —$OCF_3$; $R_1$ is represented by from 1 to 3 substituents independently chosen from the group: hydrogen, amino, nitro, $C_{1-4}$ alkyl, $C_{1-4}$ alkoxy, halogen, —$CF_3$, or —$OCF_3$; X and Y are represented by —OH, a physiologically acceptable ester, or a physiologically acceptable amide, and pharmaceutically acceptable addition salts thereof.

As used in this application:

a) the term "$C_{1-4}$ alkyl" refers to a branched or straight chained alkyl radical containing from 1–carbon atoms, such as methyl, ethyl, n-propyl, isopropyl, n-butyl, isobutyl, and the like;

b) the term "$C_{1-4}$ alkoxy" refers to a branched or straight chained alkoxy radical containing from 1–carbon atoms, such as methoxy, ethoxy, n-propoxy, isopropoxy, n-butoxy, isobutoxy, and the like;

c) the term "halogen" refers to a fluorine atom, a chlorine atom, a bromine atom, or a iodine atom;

d) the term "physiologically acceptable ester" refers to any non-toxic ester or any prodrug that allows the compounds of this application to function as NMDA antagonist: these physiologically acceptable esters may be chosen from but are not limited to compounds wherein X and Y may each independently be represented by —$OR_2$, —$OCH_2OR_2$ or —O—$(CH_2)_p$—$NR_5R_6$; $R_2$ is represented by $C_{1-4}$ alkyl, phenyl, substituted phenyl, or a phenylalkyl substituent in which the phenyl ring may be optionally substituted; p is 2 or 3, $R_5$ and $R_6$ are each independently represented by a $C_{1-4}$ alkyl or together with the adjacent nitrogen atom form a piperidino, morpholino, or pyrrolidino group; and the pharmaceutically acceptable addition salts thereof;

e) the term "physiologically acceptable amide" refers to any non-toxic amide or any prodrug that allows the compounds of this application to function as NMDA antagonists: these physiologically acceptable amides may be chosen from, but are not limited to, compounds wherein X and Y may each independently be represented by —$NR_3R_4$; $R_3$ and $R_4$ are each independently represented by hydrogen, phenyl, substituted phenyl, phenylalkyl, or a $C_{1-4}$ alkyl; or $R_3$ and $R_4$ are taken together with the adjacent nitrogen to form a ring —$CH_2$—$CH_2$—Z—$CH_2$—$CH_2$— wherein Z is a bond, O, S, or $NR_7$ in which $R_7$ is hydrogen or $C_{1-4}$ alkyl; such rings include but are not limited to piperidino, morpholino, thiomorpholino, piperazino, N-methylpiperazino, or pyrrolidino and the pharmaceutically acceptable addition salts thereof;

f) the term "phenyl" or "Ph" refers to a phenyl moiety ($C_6H_5$) of the formula;

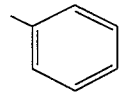

g) the term "substituted phenyl" refers to a phenyl moiety of the formula

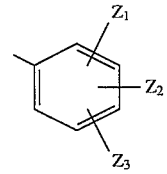

which may have from 1 to 3 substituents independently chosen from the group: hydrogen, halogens, $C_{1-4}$ alkyl, $C_{1-4}$ alkoxy, —$CF_3$, —$OCF_3$, —OH, —CN, and —$NO_2$. These substituents may be the same or different and may be located at any of the ortho, meta, or para positions;

h) the term "phenylalkyl substituent" or "phenylalkyl" refers to the following structure, —$(CH_2)_m$—$C_6H_xZ_y$, in which m is an integer from 1–3. This phenyl ring may be substituted in the manner described in (g);

i) the designation " 〰〰 " refers to a bond for which the stereochemistry is not designated.

j) the term "pharmaceutically acceptable addition salts" refers to either an acid addition salt or a basic addition salt;

The expression "pharmaceutically acceptable acid addition salts" is intended to apply to any non-toxic organic or inorganic acid addition salt of the base compounds represented by Formula (I) or any of its intermediates. Illustrative inorganic acids which form suitable salts include hydrochloric, hydrobromic, sulfuric, and phosphoric acid and acid metal salts such as sodium monohydrogen orthophosphate, and potassium hydrogen sulfate. Illustrative organic acids which form suitable salts include the mono-, di-, and tricarboxylic acids. Illustrative of such acids are for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicylic, 2-phenoxybenzoic, and sulfonic acids such as p-toluenesulfonic acid, methane sulfonic acid and 2-hydroxyethane sulfonic acid. Such salts can exist in either a hydrated or substantially anhydrous form. In general, the acid addition salts of these compounds are soluble in water and various hydrophilic organic solvents, and which in comparison to their free base forms, generally demonstrate higher melting points.

The expression "pharmaceutically acceptable basic addition salts" is intended to apply to any non-toxic organic or inorganic basic addition salts of the compounds represented by the Formula (I) or any of its intermediates. Illustrative bases which form suitable salts include alkali metals or alkaline-earth metals hydroxides such as, sodium, potassium, calcium, magnesium, or barium hydroxides; ammonia and aliphatic, cyclic, or aromatic organic amines such as methylamine, dimethylamine, trimethylamine,and picoline.

The compounds of Formula (I) exist as geometric isomers. Any reference in this application to one of the compounds of Formula (I) is meant to encompass either a specific geometrical isomer or a mixture of isomers. The specific isomers can be separated and recovered by techniques known in the art such as chromatography, and selective crystallization.

Illustrative examples of compounds encompassed by Formula (I) include:

a) (E)-2-Phenyl-3-(2-carboethoxy-4,6-dichloroindol-3-yl)propenoic acid, ethyl ester,
b) (Z)-2-Phenyl-3-(2-carboethoxy-4,6-dichloroindol-3-yl)propenoic acid, ethyl ester,
c) (E)-2-Phenyl-3-(4,6-dichloroindol-3-yl-2-carboxylic acid)propenoic acid,
d) (Z)-2-Phenyl-3-(4,6-dichloroindol-3-yl-2-carboxylic acid)propenoic acid,
e) (E)-2-Phenyl-3-(2-carboethoxy-5,6-dichloroindol-3-yl)propenoic acid, ethyl ester,
f) (Z)-2-Phenyl-3-(2-carboethoxy-5,6-dichloroindol-3-yl)propenoic acid, ethyl ester,
g) (E)-2-Phenyl-3-(5,6-dichloroindol-3-yl-2-carboxylic acid)propenoic acid,
h) (Z) -2-Phenyl-3-(5,6-dichloroindol-3-yl-2-carboxylic acid)propenoic acid,
i) -N-Methyl-2-phenyl-3-(2-carbomethylamino-4,6-dichloroindol-3-yl)propenoic amide,
j) (z) -N-Methyl-2-phenyl-3-(2-carbomethylamino-4,6dichloroindol-3-yl)propenoic amide,
k) (E)-2-Phenyl-3-(2-carboethoxy-6-chloroindol-3-yl-)propenoic acid, ethyl ester,
l) (Z)-2-Phenyl-3-(2-carboethoxy-6-chloroindol-3-yl-)propenoic acid, ethyl ester,
m) (E) -2-Phenyl-3-(6-chloroindol-3-yl-2-carboxylic acid)propenoic acid,
n) (z) -2-Phenyl-3-(6-chloroindol-3-yl-2-carboxylic acid)propenoic acid,
o) (E) -2-(4-Methoxyphenyl)-3-(2-carboethoxy-4,6-dichloroindol-3-yl)propenoic acid, ethyl ester,
p) (Z) -2-(4-Methoxyphenyl)-3-(2-carboethoxy-4,6-dichloroindol-3-yl)propenoic acid, ethyl ester,
q) (E)-2-(4-Methoxyphenyl)-3-(4,6-dichloroindol-3-yl-2-carboxylic acid)propenoic acid,
r) (Z)-2-(4-Methoxyphenyl)-3-(4,6-dichloroindol-3-yl-2-carboxylic acid)propenoic acid,
s) (E)-2-(4-Aminophenyl)-3-(2-carboethoxy-4,6-dichloroindol-3-yl)propenoic acid, ethyl ester,
t) (Z)-2-(4-Aminophenyl)-3-(2-carboethoxy-4,6-dichloroindol-3-yl)propenoic acid, ethyl ester,
u) (E)-2-(4-Aminophenyl)-3-(4,6-dichloroindol-3-yl-2-carboxylic acid)propenoic acid
v) (Z)-2-(4-Aminophenyl)-3-(4,6-dichloroindol-3-yl-2-carboxylic acid)propenoic acid
w) (E)-2-(4-Chlorophenyl)-3-(2-carboethoxy-4,6-dichloroindol-3-yl)propenoic acid, ethyl ester,
x) (Z)-2-(4-Chlorophenyl)-3-(2-carboethoxy-4,6-dichloroindol-3-yl)propenoic acid, ethyl ester,
y) (E)-2-(4-Chlorophenyl)-3-(4,6-dichloroindol-3-yl-2-carboxylic acid)propenoic acid
z) (Z)-2-(4-Chlorophenyl)-3-(4,6-dichloroindol-3-yl-2-carboxylic acid)propenoic acid,
aa) (E)-2-(4-Methylphenyl)-3-(2-carboethoxy-4,6-dichloroindol-3-yl)propenoic acid, ethyl ester,
bb) (Z)-2-(4-Methylphenyl)-3-(2-carboethoxy-4,6-dichloroindol-3-yl)propenoic acid, ethyl ester,
cc) (E)-2-(4-Methylphenyl)-3-(4,6-dichloroindol-3-yl-2-carboxylic acid)propenoic
dd) (Z)-2-(4-Methylphenyl)-3-(4,6-dichloroindol-3-yl-2-carboxylic acid)propenoic acid,
ee) (E)-N-Methyl-2-phenyl-3-(4,6-dichloroindol-3-yl-2-carboxylic acid)propenoic amide,
ff) (Z)-N-Methyl-2-phenyl-3-(4,6-dichloroindol-3-yl-2-carboxylic acid)propenoic amide,
gg) (E)-N,N-Dimethyl-2-phenyl-3-(4,6-dichloroindol-3-yl-2-carboxylic acid)propenoic amide,
hh) (Z)-N,N-Dimethyl-2-phenyl-3-(4,6-dichloroindol-3-yl-2-carboxylic acid)propenoic amide,
ii) (E)-N-Phenyl-2-phenyl-3-(4,6-dichloroindol-3-yl-2-carboxylic acid)propenoic amide,
jj) (Z)-N-Phenyl-2-phenyl-3-(4,6-dichloroindol-3-yl-2-carboxylic acid)propenoic amide,
kk) (E)-N-Methyl-N-phenyl-2-phenyl-3-(4,6-dichloroindol-3-yl-2-carboxylic acid)propenoic amide,
ll) (Z)-N-Methyl-N-phenyl-2-phenyl-3-(4,6-dichloroindol-3-yl2-carboxylic acid)propenoic amide,
mm) (E)-N-Benzyl-2-phenyl-3-(4,6-dichloroindol-3-yl-2-carboxylic acid)propenoic amide,
nn) (Z)-N-Benzyl-2-phenyl-3-(4,6-dichloroindol-3-yl-2-carboxylic acid)propenoic amide,
oo) (E)-N-Morphilino-2-phenyl-3-(4,6-dichloroindol-3-yl-2-carboxylic acid)propenoic amide,
pp) (Z)-N-Morphilino-2-phenyl-3-(4,6-dichloroindol-3-yl-2-carboxylic acid)propenoic amide,
qq) (E)-N-4-Methylpiperazino-2-phenyl-3-(4,6-dichloroindol-3-yl-2-carboxylic acid)propenoic amide,
rr) (Z)-N-4-Methylpiperazino-2-phenyl-3-(4,6-dichloroindol-3-yl-2-carboxylic acid)propenoic amide,
ss) (E)-2-Phenyl-3-(2-carboethoxy-4,6-dichloroindol-3-yl)propenoic acid,
tt) (Z)-2-Phenyl-3-(2-carboethoxy-4,6-dichloroindol-3-yl) propenoic acid,
uu) (E)-2-Phenyl-3-(2-carboethoxy-4,6-dichloroindol-3-yl)propenoic acid, t-butyl ester,
vv) (Z)-2-Phenyl-3-(2-carboethoxy-4,6-dichloroindol-3-yl)propenoic acid, t-butyl ester,
ww) (S)-2-(3-Aminophenyl)-3-(4,6-dichloroindol-3-yl-2-carboxylic acid)propenoic acid,
xx) (Z)-2-(3-Aminophenyl)-3-(4,6-dichloroindol-3-yl-2-carboxylic acid)propenoic acid,
yy) (E)-2-(2-Chlorophenyl )-3-(4,6-dichloroindol-3-yl-2-carboxylic acid)propenoic zz) (Z)-2-(2-Chlorophenyl)-3-(4,6-dichloroindol-3-yl-2-carboxylic acid)propenoic acid, aaa) (E)-2-(2,4-Dichlorophenyl)-3-(4,6-dichloroindol-3-yl-2-carboxylic acid)propenoic acid, bbb) (Z)-2-(2,4-Dichlorophenyl)-3-(4,6-dichloroindol-3-yl-2-carboxylic acid)propenoic acid, ccc) (E)-2-Phenyl-3-(-4,6-dichloroindol-3-yl-2-carboxylic acid)propenoic acid amide, ddd) (Z)-2-Phenyl-3-(4,6-dichloroindol-3-yl-2-carboxylic acid)propenoic acid amide, eee) (E)-2-(4-Bromophenyl)-3-(4,6-dichloroindol-3-yl-2-carboxylic acid)propenoic acid, fff) (Z)-2-(4-Bromophenyl)-3-(4,6-dichloroindol-3-yl-2-carboxylic acid)propenoic acid, ggg) (E)-2-(4-Fluorophenyl)-3-(4,6-dichloroindol-3-yl-2-carboxylic acid)propenoic acid, hhh) (Z)-2-(4-Fluorophenyl)-3-(4,6-dichloroindol-3-yl-2-carboxylic acid)propenoic acid, iii) (E)-2-(3-Nitrophenyl)-3-(2-carboethoxy-4,6-dichloroindol-3-yl-2)propenoic acid, methyl ester, jjj) (Z)-2-(3-Nitrophenyl)-3-(2-carboethoxy-4,6-dichloroindol-3-yl)propenoic acid, methyl ester, kkk) (E)-2-(3-Nitrophenyl)-3-(4,6-dichloroindol-3-yl-2-carboxylic acid)propenoic acid, lll) (Z)-2-(3-Nitrophenyl)-3-(4,6-dichloroindol-3-yl-2-carboxylic acid)propenoic acid, mmm) (E)-2-(3-Aminophenyl)-3-(2-carboethoxy-4,6-dichloroindol-3-yl)propenoic acid, methyl ester, nnn) (Z)-2-(3-Aminophenyl)-3-(2-carboethoxy-4,6-dichloroindol-3-yl)propenoic acid, methyl ester, ooo) (E)-N-(Phenylethyl)-2-phenyl-3-(-4,6-dichloroindol-3-yl-2-carboxylic acid)propenoic acid amide, ppp) (Z)-N-(Phenylethyl)-2-phenyl-3-(4,6-dichloroindol-3-yl-2-carboxylic acid)propenoic acid amide, qqq) (E)-2-(4-Trifluoromethylphenyl)-3-(4,6-dichloroindol-3-yl-2-carboxylic acid)propenoic acid, rrr) (Z)-2-(4-Trifluoromethylphenyl)-3-(4,6-dichloroindol-3-yl-2-carboxylic acid)propenoic acid.

The compounds of Formula (I) can be prepared utilizing techniques that are analogously known in the art. One method of preparing these compounds is disclosed below in Reaction Scheme 1.

REACTION SCHEME 1

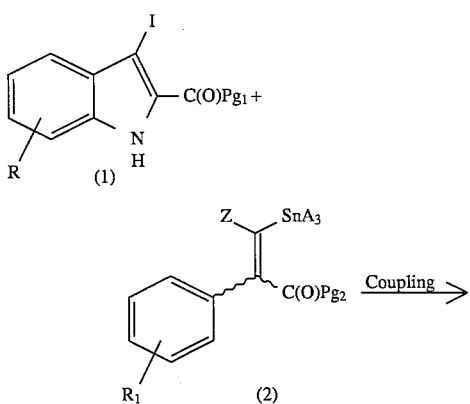

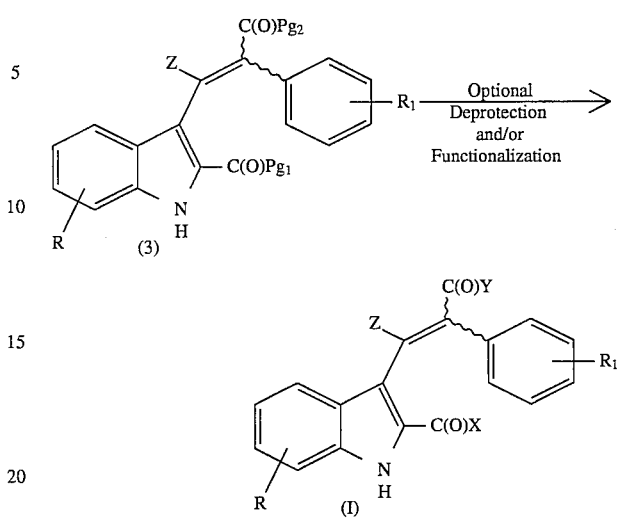

As disclosed in Reaction Scheme 1, the compounds of Formula (I) can be prepared by submitting an appropriately substituted 3-iodoindole (1) to a coupling reaction with an appropriately substituted 3-stannylpropenoic acid (2) to give compound (3). The stannyl group, $SnA_3$, of compound (2) will have three substituents, A, that may be either alkyl or aryl, such as phenyl, methyl, ethyl, n-butyl, etc., with methyl and n-butyl being preferred and n-butyl being most preferred. In structure (1), R is as defined for compounds of Formula (I). In structure (2) $R_1$ and Z are as defined for compounds of Formula (I) or give rise after deprotection to $R_1$ as defined for compounds of Formula (I). $Pg_1$ and $Pg_2$ are each independently represented by groups such as, physiologically acceptable esters, physiologically acceptable amides, hydrolyzable esters, or active ester leaving groups known in the art.

The formation and use of active ester leaving groups is well known and appreciated in the art. Active ester leaving groups include but are not limited to anhydrides, mixed anhydrides, acid chlorides, acid bromides, 1-hydroxybenzotriazole esters, 1-hydroxysuccinimide esters, or the activated intermediates formed in the presence of coupling reagents, such as dicyclohexylcarbodiimide, 1-(3-dimethyaminopropyl)-3-ethylcarbodiimide, and 2-ethoxy-1-ethoxycarbonyl-1,2-dihydroquinolone. Active ester leaving groups may be prepared and isolated before their use or may be prepared and used without isolation to form physiologically acceptable esters or physiologically acceptable amides.

The starting materials (1) and (2) are readily available to one of ordinary skill in the art; M. R. Brennan, et al., *Heterocycles*, 24, 2879–2884, (1986); R. D. Arnold, et al., *J. Org. Chem.*, 24, 117–118, (1959); [J. C. Cochran, et al., *Organometallics*, 8, 804–812, (1989)] J. S. Nimitz and H. S. Mosher *JOC* 46, 211–213, (1981); (T. A. Blumenkopf *Synth. Commun.* 16, 139–147, (1986); D. Habäch and K. Metzger *Heterocycles* 24, 289–296, (1986); Y. Watanabe et al *Tet. Let.* 27, 215–218 (1986); J. R. McCarthy et al *JACS* 113, 7439–7440, (1991).

Typically, the coupling reaction depicted in Reaction Scheme 1 is performed in a suitable solvent, such as 1-methyl-2-pyrrolidinone. The reaction is performed using a molar excess of 3-iodoindole (1), the amount of (1) used ranges from 1.1 to 10 equivalents with 1.5 equivalents being preferred. The coupling is performed using a suitable palladium catalyst, such as tetrakis(triphenylphosphine- )palladium (0), bis(acetonitrile)palladium (II) chloride, palladium (II) chloride, palladium (II) acetate, palladium (II) bromide, bis(benzonitrile)palladium (II) chloride, palladium (II) acetoacetate with tetrakis(triphenylphosphine)palladium (0), bis(acetonitrile)palladium (II) chloride, palladium (II) chloride, palladium (II) acetate, being preferred and bis(acetonitrile)palladium (II) chloride being most preferred. The coupling is performed at a temperature ranging from 0° C. to the refluxing temperature of the solvent. For couplings performed in 1-methyl-2-pyrrolidinone the preferred temperature is 60° C. The coupling reactions depicted in Reaction Scheme 1 require from 1 to 72 hours and should be stopped at a time that maximizes the desired product (3) and minimizes undesired products. The product (3) of the coupling reaction can be isolated and purified using techniques well known in the art. These techniques include aqueous extraction using suitable organic solvents, such as ethyl acetate, diethyl ether, dichloromethane, etc., evaporation, chromatography using suitable eluent, such as mixtures of ethyl acetate and hexane, dichloromethane, etc., and recrystallization.

The product (3) obtained from the coupling reaction may be optionally deprotected and/or functionalized using techniques well known in the art to give compounds of Formula (I). These techniques include hydrolysis of esters, selective hydrolysis of esters, transesterification, amidation of activated ester leaving groups, and esterification of activated ester leaving groups.

As is disclosed in Reaction Scheme 1, the compounds of Formula (I) can be prepared by submitting a compound (3) to an appropriate functionalization reaction which introduces the appropriate functionality at the 2-position of the indole nucleus and/or at the 1-position of the propenoic acid thereby producing one of the desired compounds of Formula (I). In structure (3), Z, R, and $R_1$ are as defined in Formula (I) or give rise after deprotection to $R_1$ as defined in Formula (I) and $Pg_1$ and $Pg_2$ are each independently represented by groups such as, $C_{1-4}$ alkyl, or other active ester leaving groups known in the art, physiologically acceptable ester, or physiologically acceptable amide.

The functionalization reactions can be carried out using techniques well known in the art. For example, ester functionalities can be added to the 2-position of the indole nucleus and/or at the 1-position of the propenoic acid utilizing a variety of esterification techniques. One suitable esterification technique comprises contacting the appropriate compound of structure (3) in which $Pg_1$ and $Pg_2$ are $C_{1-4}$ alkyl functions with an excess of an alcohol of the formula XOH or YOH in which X and Y are the same as defined for Formula (I). The reaction is typically carried out in the presence of an excess of a base such as potassium carbonate. The reaction is typically carried out at a temperature ranging from room temperature to reflux for a period of time ranging from 1 hour to 24 hours. After the reaction is completed, the desired product of Formula (I) can be recovered by organic extraction. It may then be purified by flash chromatography and/or recrystallization as is known in the art. Suitable chromatographic solvents include mixtures of ethyl acetate and hexane, dichloromethane, and mixtures of dichloromethane and methanol. Suitable recrystallization solvents include ethyl acetate/hexane.

Amides can also be easily be prepared by contacting a compound of structure (3) in which $Pg_1$ and $Pg_2$ are $C_{1-4}$ alkyls with an excess of ammonia or a mono- or dialkylamine corresponding to the desired X or Y substituent at a temperature of from 0°–100° C. for a period of time ranging from 1–48 hours using the amine as solvent or in an inert solvent such as tetrahydrofuran. The resulting amide derivatives of Formula I can then be isolated and purified by techniques known in the art.

As is readily apparent to those skilled in the art, if X and Y are not both represented by the same function in the final product, then it will be necessary to carry out the deprotection and the functionalization reactions in a sequential manner utilizing suitable protecting groups such as those described in *Protecting Groups in Organic Synthesis*, T. Greene. This can be done utilizing techniques known to those skilled in the art; D. B. Bryan et al, *JACS*, 99, 2353 (1977); E. Wuensch, *Methoden der Organischen Chemie* (Houben-Weyl), E. Mueller, Ed., George Theime Verlag, Stuttgart, 1974, Vol. 15; M. G. Saulnierand and G. W. Gribble, *JOC*, 47, 2810 (1982); Y. Egawa et al, *Chem. Pharm. Bull.* 7, 896 (1963); R. Adams and L. H. Ulich, *JACS*, 42, 599 (1920); and J Szmuszkoviocz, *JOC*, 29, 834 (1964).

For example, a compound of Formula (I) in which Y is a physiologically acceptable amide and X is a physiologically acceptable ester or -OH can be prepared from a compound of structure (3) in which $Pg_2$ is t-butyl-O— and $Pg_1$ is a physiologically acceptable ester other than t-butyl or a hydrolyzable ester. Selective removal of the t-butyl group gives a compound of structure (3) in which $Pg_2$ is —OH and $Pg_1$ is a pysiologically acceptable ester other than t-butyl or a hydrolyzable ester which can be amidated through the formation of an activated ester leaving group followed by the addition of an suitable amine as is well known in the art. A suitable amine is one which gives a physiologically acceptable amide, Y, as is desired in the final product of Formula (I). Suitable amines include but are not limited to methylamine, dimethylamine, ethylamine, diethylamine, propylamine, butylamine, aniline, 4-chloroaniline, N-methylaniline, benzylamine, phenethylamine, morpholine, piperazine, piperidine, N-methylpiperazine, thiomorpholine, pyrrolidine, and N-methylbenzylamine. Formation of an active ester leaving group may require protection of the indole NH using a suitable protecting group, such as benzenesulfonyl, p-toluenesulfonyl, trimethylsilyl, trimethylsilylethoxymethyl, and the like. In cases in which the indole NH requires protection this is best done before the removal of t-butyl from $Pg_2$. Further functionalization or hydrolysis gives a compound of Formula (I) in which Y is a physiologically acceptable amide and X is a physiologically acceptable ester or —OH. After the functionalization removal of the indole NH protecting group gives a compound of Formula (I).

Similarly, a compound of Formula (I) in which X is a physiologically acceptable amide and Y is a physiologically acceptable ester or —OH can be prepared from a compound of structure (3) in which $Pg_1$ is t-butyl-O— and $Pg_2$ is a physiologically acceptable ester other than t-butyl or a hydrolyzable ester.

The compounds of Formula (I) in which X and Y are —OH can be prepared from a compound of structure (3) in which $Pg_1$ and $Pg_2$ are $C_{1-4}$ alkoxy, or an activated ester leaving group by deprotection using a molar excess of a suitable reagent, such as lithium hydroxide, sodium hydroxide, potassium hydroxide, sodium bicarbonate, sodium carbonate, or potassium carbonate with lithium hydroxide, sodium hydroxide, potassium hydroxide being preferred and lithium hydroxide being most preferred. These deprotections are carried out in a suitable solvent, such as methanol, ethanol, mixtures of methanol or ethanol and water, mixtures of tetrahydrofuran and water, or water. The reaction is typically carried out at a temperature ranging from room temperature to reflux for a period of time ranging from 1 hour to 24 hours. After the reaction is completed, the desired product of Formula (I) can be recovered by techniques well known in the art, such as evaporation, precipitation by adjustment of the pH of the solution with a suitable acid such as hydrochloric acid, acetic acid, etc., extraction, and recrystallization.

The compounds of structure (2) can be prepared utilizing techniques that are analogously known in the art, J. S. Nimitz and H. S. Mosher *JOC* 46, 211–213, (1981), (T. A. Blumenkopf *Synth. Commun.* 16, 139–147, (1986), D. Habäch and K. Metzger *Heterocycles* 24, 289–296, (1986), Y. Watanabe et al *Tet. Let.* 27, 215–218 (1986), J. R. McCarthy et al *JACS* 113, 7439–7440, (1991). One method of preparing these compounds is disclosed below in Reaction Scheme 1a.

REACTION SCHEME 1a

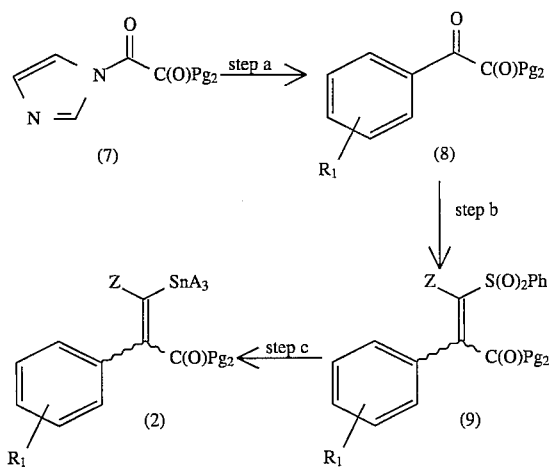

In Reaction Scheme 1a, step a, an appropriate imidazolide of structure (7) prepared by the method of J. S. Nimitz and H. S. Mosher *JOC* 46, 211–213, (1981), is contacted with an appropriate organometallic reagent to give an α-keto ester of structure (8).

An appropriate imidazolide of structure (7) is one in which $Pg_2$ is a physiologically acceptable ester, physiologically acceptable amide, hydrolyzable ester, or active ester leaving group; or is a group which gives rise to a physiologically acceptable ester or a physiologically acceptable amide as desired in the final product of Formula (I) or gives rise to an active ester leaving group which is converted to a physiologically acceptable ester or a physiologically acceptable amide as desired in the final product of Formula (I).

An appropriate organometallic reagent is one which transfers a phenyl or substituted phenyl of the formula

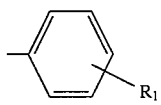

in which $R_1$ as is desired in the final product of the Formula (I) or gives rise upon deprotection to $R_1$ as desired in the final product of Formula (I).

For example, an imidazolide of structure (7) is contacted with a suitable organometallic reagent. As is appreciated by one of ordinary skill in the art a suitable organometallic reagent can be chosen from the following: organolithium reagents, organosodium reagents, organomagnesium reagents, organozinc reagents, organomanganese reagents, etc., with organolithium reagents and organomagnesium reagents being preferred and organomagnesium reagents being most preferred. The reaction is carried out in a suitable solvent, such as tetrahydrofuran or diethyl ether, at a temperature of from −78° C. to the reflux temperature of the solvent. The product can be isolated by techniques well known in the art, such as extraction and evaporation in vacuo. The product can then be purified by techniques well known in the art, such as distillation, chromatography, or recrystallization.

In Reaction Scheme 1a, step b, an appropriate α-keto ester of structure (8) known in the art and known analogously in the art (J. S. Nimitz and H. S. Mosher *JOC* 46, 211–213, (1981)), is contacted with an appropriate organophosphorous ylide to give an vinyl sulfone of structure (9).

An appropriate α-keto ester of structure (8) is one in which Z is as desired in the final product of Formula (I); $Pg_2$ is a physiologically acceptable ester, physiologically acceptable amide, hydrolyzable ester, or active ester leaving group; or gives rise to a —OH, physiologically acceptable ester or a physiologically acceptable amide as desired in the final product of Formula (I); and $R_1$ is as desired in the final product of the Formula (I) or gives rise upon deprotection to $R_1$ as desired in the final product of Formula (I).

An appropriate organophosphorous ylide is one which converts a α-keto ester of structure (8) to a vinyl sulfone of structure (9). An appropriate organophosphorous ylide is formed by contacting an appropriate organophosphorous reagent, such as diethyl phenylsulphonylmethylphosphonate (T. A. Blumenkopf *Synth. Commun.* 16,139–147, (1986), diethyl 1-(phenylsulphonyl)ethylphosphonate, or diethyl 1-(phenylsulphonyl)propylphosphonate with a suitable base, such as lithium diisopropylamide, sodium hydride, lithium bis(trimethylsilyl)amide or potassium t-butoxide. Appropriate organophosphorous reagents and the use of appropriate organophosphorous reagents is well known and appreciated in the art (J. Boutagy and R. Thomas *Chem. Rev.* 74, 8799, (1974); D. Habäch and K. Metzger *Heterocycles* 24, 289–296, (1986); P. J. Kocienski and J. Tideswell *Synth. Commun.* 9, 411–419, (1979)).

For example, an appropriate organophosphorous reagent is contacted with a suitable base, such as lithium diisopropylamide, sodium hydride, lithium bis(trimethylsilyl)amide or potassium t-butoxide. The ylide formation is carried out in a suitable solvent, such as tetrahydrofuran, benzene, or diethyl ether. The ylide formation is generally carried out at a temperature of from −78° C. to ambient temperature. An appropriate organophosphorous ylide is contacted with an appropriate α-keto ester of structure (8). The reaction is carried out in a suitable solvent, such as tetrahydrofuran, benzene, or diethyl ether. Generally, the reaction is carried out in the same solvent used to form the appropriate organophosphorous ylide. The reaction is carried out at temperatures of from −78° C. to the reflux temperature of the solvent. The reaction generally requires form 1 hour to 48 hours. The product can be isolated by techniques well known in the art, such as extraction and evaporation in vacuo. The product can then be purified by techniques well known in the art, such as distillation, chromatography, or recrystallization.

In Reaction Scheme 1a, step c, an appropriate vinyl sulfone of structure (9) is contacted with an appropriate tri-substitutedtin hydride reagent to give an appropriately substituted 3-stannylpropenoic acid (2).

An appropriate vinyl sulfone of structure (9) is one in which Z, $R_1$, and $Pg_2$ are as is desired on the final product of Formula (I) or is one in which $R_1$ and $Pg_2$ which give rise after deprotection and/or functionalization to $R_1$ and Y as are desired in the final product of Formula (I).

An appropriate tri-substituted tin hydride reagent is one which introduces the stannyl group, $SnA_3$. An appropriate tri-substitutedtin hydride reagent has three substituents, A, which may be either alkyl or aryl, such as phenyl, methyl, ethyl, n-butyl, etc., with methyl and n-butyl being preferred and n-butyl being most preferred.

For example, an appropriate vinyl sulfone of structure (9) is contacted with from 2 to 5 molar equivalents of an appropriate tri-substitutedtin hydride reagent. The reaction is carried out in a suitable solvent, such as toluene, benzene, hexane, or cyclohexane. The reaction is carried out in the presence of a suitable catalyst, such as 2,2'-azobisisobutyronitrile (AIBN), benzoyl peroxide, and the like. The reaction is carried out at a temperature from ambient temperature to the refluxing temperature of the solvent. Compound of the structure (2) can be isolated and purified by techniques well known in the art, such as extraction, evaporation, chromatography, and recrystallization.

Another method of preparing the compounds of Formula (I) is disclosed below in Reaction Scheme 2.

REACTION SCHEME 2

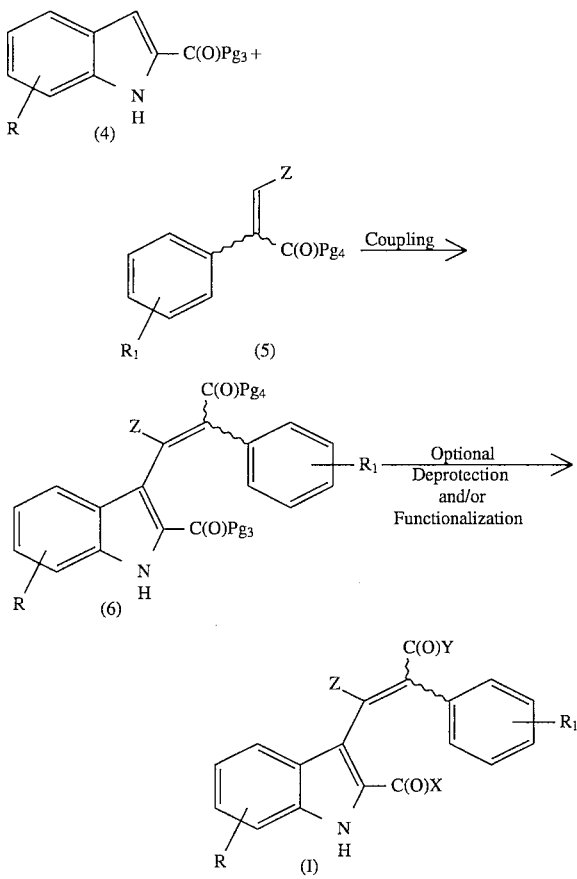

As disclosed in Reaction Scheme 2, the compounds of Formula (I) can be prepared by submitting an appropriately substituted indole (4) to a coupling reaction with an appropriately substituted propenoic acid derivative (5) to give compound (6). In structure (4), R is as defined for compounds of Formula (I). In structure (5) $R_1$ and Z are as defined for compounds of Formula (I) or give rise after deprotection to a group $R_1$ as desired in the final product of Formula (I). $Pg_3$ and $Pg_4$ are each independently represented by groups such as, physiologically acceptable esters, physiologically acceptable amides, hydrolyzable esters, or active ester leaving groups known in the art. The starting materials (4) and (5) and techniques used in Reaction Scheme 2 are readily available to one of ordinary skill in the art; I. Amer and H. Alper, *J. Organometallic Chem.*, 383, 573–77, (1990); C. Nájera, et al., *Tet. Let.*, 30, 6085–88, (1989); Y. Murakami, et al., *Heterocycles*, 22, 1493–96, (1984); J. C. Cochran, et al., *Organometallics*, 8, 804–812, (1989). The coupling reaction of Reaction Scheme 2 is preferred when compounds of Formula (I) in which Y is a physiologically acceptable amide are to be prepared directly in the coupling reaction. Typically, the coupling reaction depicted in Reaction Scheme 2 is performed in a suitable solvent, such as acetic acid, trifluoroacetic acid, acetonitrile, methanol, dimethylformamide with trifluoroacetic acid being preferred. The reaction is performed using an approximately one to one ratio of starting materials (4) and (5). The coupling is performed using an equimolar amount or a slight molar excess of a suitable palladium reagent, such as bis(acetonitrile)palladium (II) chloride, palladium (II) chloride, palladium (II) acetate, palladium (II) bromide, palladium (II) trifluoroacetate, bis(benzonitrile) palladium (II) chloride, palladium (II) acetoacetate with bis(acetonitrile)palladium (II) chloride, palladium (II) trifluoroacetate, palladium (II) chloride, palladium (II) acetate, being preferred and with palladium (II) chloride and palladium (II) trifluoroacetate being most preferred. The coupling is performed at a temperature ranging from 0° C. to the refluxing temperature of the solvent. For couplings performed in trifluoroacetic acid the preferred temperature is 50° C. The coupling reactions depicted in Reaction Scheme 2 require from 1 to 72 hours and should be stopped at a time that maximizes the desired product (6) and minimizes undesired products. The product (6) of the coupling reaction can be isolated and purified using techniques well known in the art. These techniques include: aqueous extraction using suitable organic solvents, such as ethyl acetate, diethyl ether, dichloromethane, etc., evaporation, chromatography using suitable eluent, such as mixtures of ethyl acetate and hexane, dichloromethane, etc., and recrystallization.

The compound (6) may be optionally deprotected and/or functionalized using techniques well known in the art to give compounds of Formula (I) as was taught above in Reaction Scheme 1 for compounds of structure (3).

Another method of preparing the compounds of Formula (I) is disclosed below in Reaction Scheme 3.

REACTION SCHEME 3

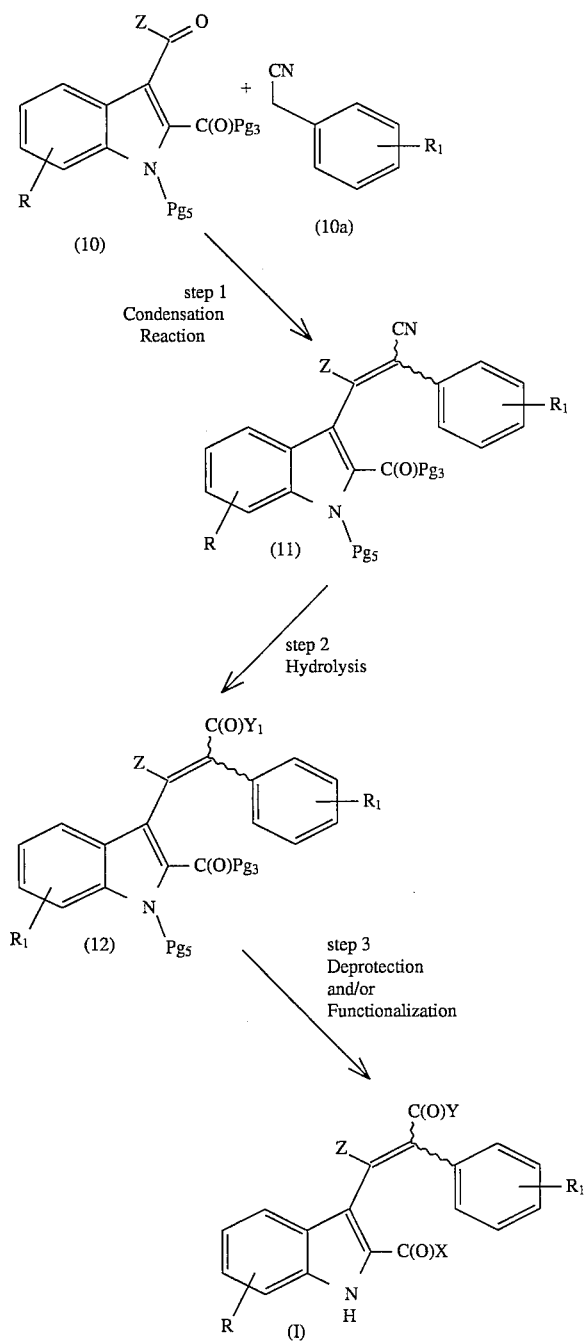

In Reaction Scheme 3, step 1, an appropriate indole of structure (10) is contacted with an appropriate arylacetonitrile (10a) in a condensation reaction to give a 2-aryl-3-(indol-3-yl)propenonitrile of structure (11).

An appropriate indole compound of structure (10) is one in which R, and Z are as desired in the final product of Formula (I), $Pg_3$ is X as desired in the final product of formula (I) or gives rise after deprotection and functionalization as required to X as desired in the final product of Formula (I), and $Pg_5$ is hydrogen or a protecting group which is readily removed to give a final product of Formula (I) or allows for selective deprotection and functionalization as may be required to incorporate X and Y desired in the final product of Formula (I). Appropriate indoles of structure (10) are readily prepared by methods well known in the art, such as the Fischer indole synthesis, introduction of a 3-position carbonyl substituent, and if required, protection of the indole nitrogen. An appropriate arylacetonitrile (10a) is one in which $R_1$ is as desired in the final product of Formula (I).

For example, an appropriate indole of structure (10) is contacted with an appropriate arylacetonitrile (10a). The reaction is carried out in a suitable solvent, such as tetrahydrofuran, ethanol, or methanol. The reaction is carried out using a suitable base, such as piperidine, triethylamine, sodium hydride, or sodium carbonate. The reaction is generally carried out at temperatures of from ambient temperature to the refluxing temperature of the solvent. The reaction generally requires from 1 hour to 120 hours. The product can be isolated by techniques well known in the art, such as extraction and evaporation. The product can then be purified by techniques well known in the art, such as distillation, chromatography, or recrystallization.

In Reaction Scheme 3, step 2, an appropriate 2-aryl-3-(indol-3-yl) propenonitrile of structure (11) is hydrolyzed to give a compound of structure (12) in which $Y_1$ is —OH or —$NH_2$. It is understood that such hydrolyses may be carried out in a number of steps through intermediates, such as imides.

In Reaction Scheme 3, step 3, the compound of structure (12) obtained from the hydrolysis reaction may be optionally protected, deprotected, and functionalized using techniques well known in the art and described in Reaction Scheme 1 to give compounds of Formula (I). These techniques include formation of esters to give a compound of structure (3), hydrolysis of esters, selective hydrolysis of esters, transesterification, removal of indole protecting groups, reduction of nitro groups to amino groups, amidation of activated ester leaving groups, and esterification of activated ester leaving groups.

Another method of preparing the compounds of Formula (I) in which Z is hydrogen is disclosed below in Reaction Scheme 4.

REACTION SCHEME 4

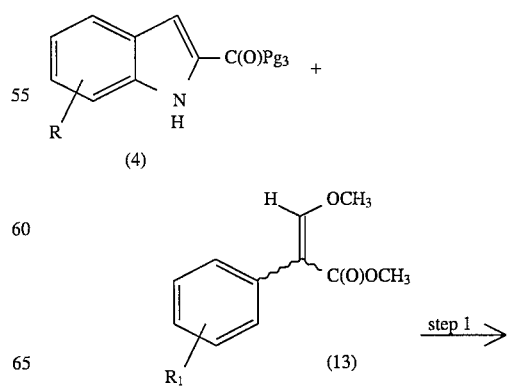

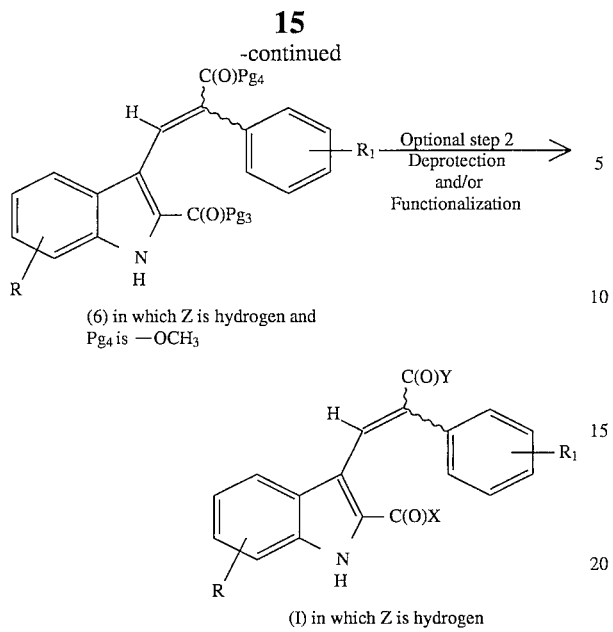

(6) in which Z is hydrogen and
Pg$_4$ is —OCH$_3$ (I) in which Z is hydrogen

In Reaction Scheme 4, step 1, an appropriate indole of structure (4) is contacted with an appropriate enol ether of structure (13) to give a compound (6) in which Z is hydrogen and Pg$_4$ is —OCH$_3$.

An appropriate indole compound of structure (4) is one as described in Reaction Scheme 2. An appropriate enol ether of structure (13) is one in which $R_1$ is as defined for compounds of Formula (I) or give rise after deprotection or functionalization, including the reduction of a nitro group to an amino group, to a group $R_1$ as desired in the final product of Formula (I). Appropriate enol ethers of structure (13) are readily available by methylation of the sodium salt of either methyl α-formylphenyl acetate or methyl α-formyl(substituted-phenyl) acetates as is well known and appreciated in the art.

For example, an appropriate indole of structure (4) is contacted with an appropriate enol ether of structure (13). The reaction is carried out in the presence of about 1 to about 1.5 molar equivalents of a suitable catalyst, such as trimethylsilyl triflate. The reaction is carried out in a suitable solvent, such as dichloromethane or dichloroethane. The reaction general is carried out at temperatures of from 0° C. to the refluxing temperature of the solvent. The reaction generally requires from 1 hour to 120 hours. The product can be isolated by techniques well known in the art, such as extraction and evaporation. The product can then be purified by techniques well known in the art, such as distillation, chromatography, or recrystallization.

In Reaction Scheme 4, optional step 2, a compound of structure (6) can be deprotected and/or functionalized as described in Reaction Scheme 1. It is understood that deprotection and/or functionalization encompasses the reduction of a nitro group to an amino group. Such reductions are well known and appreciated in the art.

Another method of preparing the compounds of Formula (I) is disclosed below in Reaction Scheme 5.

REACTION SCHEME 5

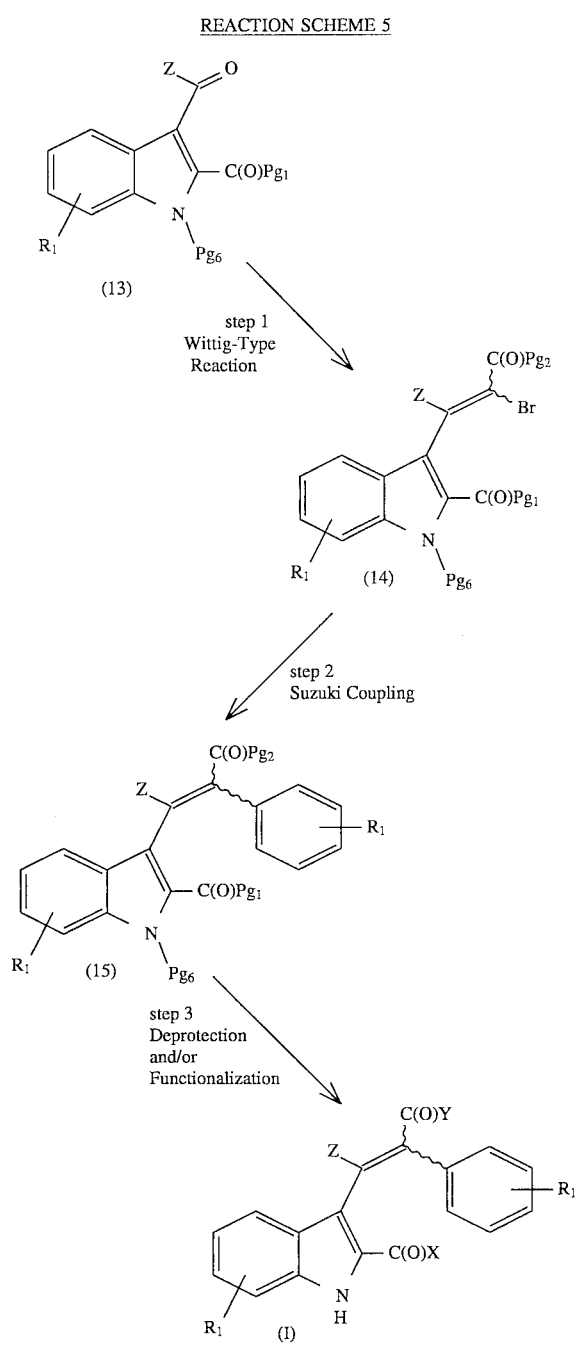

As disclosed in Reaction Scheme 5, the compounds of Formula (I) can be prepared by submitting an appropriate indole (13) to a Wittig-type reaction to give an 2-bromo-3-(indol-3-yl) propenoic acid ester of structure (14), a Suzuki coupling reaction with an appropriate phenylboronic acid or substituted phenylboronic acid to give compound (15), and deprotection and functionalization to give a compound of Formula (I).

In Reaction Scheme 5, step 1, an appropriate indole of structure (13) is contacted with an appropriate organophosphorous ylid in a Wittig-type reaction to give an 2-bromo-3-(indol-3-yl)propenoic acid ester of structure (14).

An appropriate indole compound of structure (13) is one in which R, and Z are as desired in the final product of Formula (I), $Pg_1$ is X as desired in the final product of Formula (I) or gives rise after deprotection and functionalization as required to X as desired in the final product of Formula (I), and $Pg_6$ is a protecting group which is readily removed to give a final product of Formula (I) or allows for selective deprotection and functionalization as may be required to incorporate X and Y desired in the final product of Formula (I). The use of indole compounds of structure (13) in which $Pg_6$ is tosyl is preferred. Appropriate indoles of structure (13) are readily prepared by methods well known in the art, such as the Fischer indole synthesis, introduction of a 3-position carbonyl substituent, and protection of the indole nitrogen.

An appropriate organophosphorous ylid is one which converts the 3-position carbonyl of an indole of structure (13) to an 2-bromopropenoic acid ester of structure (14) in which $Pg_2$ is Y as desired in the final product of Formula (I) or gives rise after deprotection and functionalization as required to Y as desired in the final product of Formula (I). An appropriate organophosphorous ylid is formed by contacting an appropriate organophosphorous reagent, such as t-butyl diethylphosphonobromoacetate or ethyl diethylphosphonobromoacetate, with a suitable base, such as lithium diisopropylamide, sodium hydride, lithium bis(trimethylsilyl)amide or potassium t-butoxide. Appropriate organophosphorous reagents and the use of appropriate organophosphorous reagents is well known and appreciated in the art.

For example, an appropriate organophosphorous reagent is contacted with a suitable base, such as lithium diisopropylamide, sodium hydride, lithium bis(trimethylsilyl)amide or potassium t-butoxide. The ylid formation is carried out in a suitable solvent, such as tetrahydrofuran, benzene, or diethyl ether. The ylid formation is generally carried out at a temperature of from −78° C. to ambient temperature. An appropriate organophosphorous ylid is contacted with an appropriate indole of structure (13). The reaction is carried out in a suitable solvent, such as tetrahydrofuran, benzene, or diethyl ether. Generally, the reaction is carried out in the same solvent used to form the appropriate organophosphorous ylid. The reaction is carried out at temperatures of from −78° C. to the reflux temperature of the solvent. The reaction generally requires from 1 hour to 48 hours. The product can be isolated by techniques well known in the art, such as extraction and evaporation. The product can then be purified by techniques well known in the art, such as distillation, chromatography, or recrystallization.

In Reaction Scheme 5, step 2, an appropriate 2-bromo-3-(indol-3-yl) propenoic acid ester of structure (14) is contacted with an appropriate phenylboronic acid or substituted phenylboronic acid in a Suzuki coupling to give a compound of structure (15). N. Miyaura et al., *J. Org. Chem.*, 51, 5467–5471 (1986); Y. Hoshino et al., *Bull. Chem. Soc. Japan*, 61, 3008–3010 (1988); N. Miyaura et al., *J. Am. Chem. Soc.*, 111, 314–321 (1989); W. J. Thompson et al., *J. Org. Chem.*, 53, 2052–2055 (1988); and T. I. Wallow and B. M. Novak, *J. Org. Chem.*, 59, 5034–5037 (1994).

An appropriate phenylboronic acid or substituted phenylboronic acid is one in which transfers a phenyl or substituted phenyl as desired in the 2-position of the compound of Formula (I) or is one which transfers a substituted phenyl which can be deprotected or modified to a substituted phenyl as desired in the final product of Formula (I). The preparation and use of phenylboronic acids and substituted phenylboronic acids is well known and appreciated in the art. W. J. Thompson and J Gaudino, *J. Org. Chem.*, 49, 5237–5243 (1984). Phenylboronic acids and substituted phenylboronic acids are frequently contaminated with their corresponding anhydrides which do not perform well in the Suzuki coupling. Material contaminated by detrimental amounts of anhydride can be converted to the corresponding acid by hydrolysis. The hydrolysis is performed, if required, by briefly boiling in water and the phenylboronic acid or substituted phenylboronic acid is recovered by filtration.

For example, an appropriate 2-bromo-3-(indol-3-yl)propenoic acid ester of structure (14) is contacted with an appropriate phenylboronic acid or substituted phenylboronic acid. The Suzuki coupling reaction is performed in a suitable solvent, such as toluene or tetrahydrofuran. The reaction is performed using from about 1.1 to about 3 molar equivalents of an appropriate phenylboronic acid or substituted phenylboronic acid. The reaction is carried out in the presence of from about 1 to about 3 molar equivalents of a suitable base, such as potassium carbonate, sodium carbonate. The coupling is performed using a suitable palladium catalyst, such as tetrakis(triphenylphosphine)palladium (0), bis(acetonitrile)palladium (II) chloride, palladium (II) chloride, palladium (II) acetoacetate, and tris(dibenzylideneacetone)dipalladium(0). The suitable palladium catalyst chosen may be modified by the use of ligands, such as tri(fur-2-yl)phosphine and tri(o-toluene)phosphine. V. Farina and B. Krishnan, *J. Am. Chem. Soc.*, 113, 9586–9595 (1991). The coupling is performed at a temperature ranging from 0° C. to the refluxing temperature of the solvent. The coupling reactions depicted in Reaction Scheme 5 generally require from 6 hours to 14 days. The product (15) of the coupling reaction can be isolated and purified using techniques well known in the art. These techniques include extraction, evaporation, chromatography and recrystallization.

In Reaction Scheme 5, step 3, the compound of structure (15) obtained from the coupling reaction is deprotected and functionalized using techniques well known in the art to give compounds of Formula (I). These techniques include hydrolysis of esters, selective hydrolysis of esters, transesterification, removal of indole protecting groups, amidation of activated ester leaving groups, and esterification of activated ester leaving groups. As is appreciated to one skilled in the art, in Scheme 5 the number and order of deprotection, functionalization, and protection steps carried out will depend on the compound of Formula (I) which is desired as the product of Scheme 5. The selection, use, and removal of protecting groups utilizing suitable protecting groups such as those described in *Protecting Groups in Organic Synthesis* by T. Greene, Wiley-Interscience (1981) is well known and appreciated in the art.

As is disclosed in Reaction Scheme 5, step 3, the compounds of Formula (I) can be prepared by submitting a compound (15) to an appropriate functionalization reaction which introduces the appropriate functionality at the 2-position of the indole nucleus and/or at the 1-position of the propenoic acid thereby producing one of the desired compounds of Formula (I).

The functionalization reactions can be carried out as taught in Reaction Scheme 1. In addition, amides can also be easily be prepared as taught in Reaction Scheme 1. As is readily apparent to those skilled in the art, if X and Y are not both represented by the same function in the final product, then it will be necessary to carry out deprotection and functionalization reactions in a sequential manner as taught in Reaction Scheme 1.

The formation and use of active ester leaving groups used in functionalization reactions is well known and appreciated in the art. Active ester leaving groups include but are not limited to anhydrides, mixed anhydrides, acid chlorides, acid bromides, 1-hydroxybenzotriazole esters, 1-hydroxysuccinimide esters, or the activated intermediates formed in the presence of coupling reagents, such as dicyclohexylcarbodiimide, 1-(3-dimethyaminopropyl)-3-ethylcarbodiimide, and 2-ethoxy-1-ethoxycarbonyl-1,2-dihydroquinolone. Active ester leaving groups may be prepared and isolated before their use or may be prepared and used without isolation to form physiologically acceptable esters or physiologically acceptable amides.

For example, a compound of Formula (I) in which Y is a physiologically acceptable amide and X is a physiologically acceptable ester or —OH can be prepared from a compound of structure (15) in which $Pg_2$ is t-butyl-O— and $Pg_1$ is a physiologically acceptable ester other than t-butyl-O— or a hydrolyzable ester. Selective removal of the t-butyl group gives a compound of structure (15) in which $Pg_2$ is —OH which can be amidated through the formation of an activated ester leaving group followed by the addition of an suitable amine as is well known in the art. A suitable amine is one which gives a physiologically acceptable amide as is desired in the final product of Formula (I). Suitable amines include but are not limited to methylamine, dimethylamine, ethylamine, diethylamine, propylamine, dipropylamine, butylamine, dibutylamine, aniline, 4-chloroaniline, N-methylaniline, benzylamine, phenethylamine, morpholine, piperazine, piperidine, N-methylpiperazine, thiomorpholine, pyrrolidine, and N-methylbenzylamine. Formation of an active ester leaving group requires protection of the indole NH using a suitable protecting group, such as benzenesulfonyl, p-toluenesulfonyl, trimethylsilyl, trimethylsilylethoxymethyl, and the like. Further functionalization or hydrolysis gives a compound of Formula (I) X is a physiologically acceptable ester or —OH. After the functionalization removal of the indole NH protecting group gives a compound of Formula (I).

Similarly, a compound of Formula (I) in which X is a physiologically acceptable amide and Y is a physiologically acceptable ester or —OH can be prepared from a compound of structure (15) in which $Pg_1$ is t-butyl-O— and $Pg_2$ is a physiologically acceptable ester other than t-butyl or a hydrolyzable ester.

The compounds of Formula (I) in which X and Y are —OH can be prepared from a compound of structure (15) as taught in Reaction Scheme 1.

Alternately, the compounds of Formula (I) can be prepared as described in Reaction Scheme 6. The reagents and starting materials are readily available to one of ordinary skill in the art.

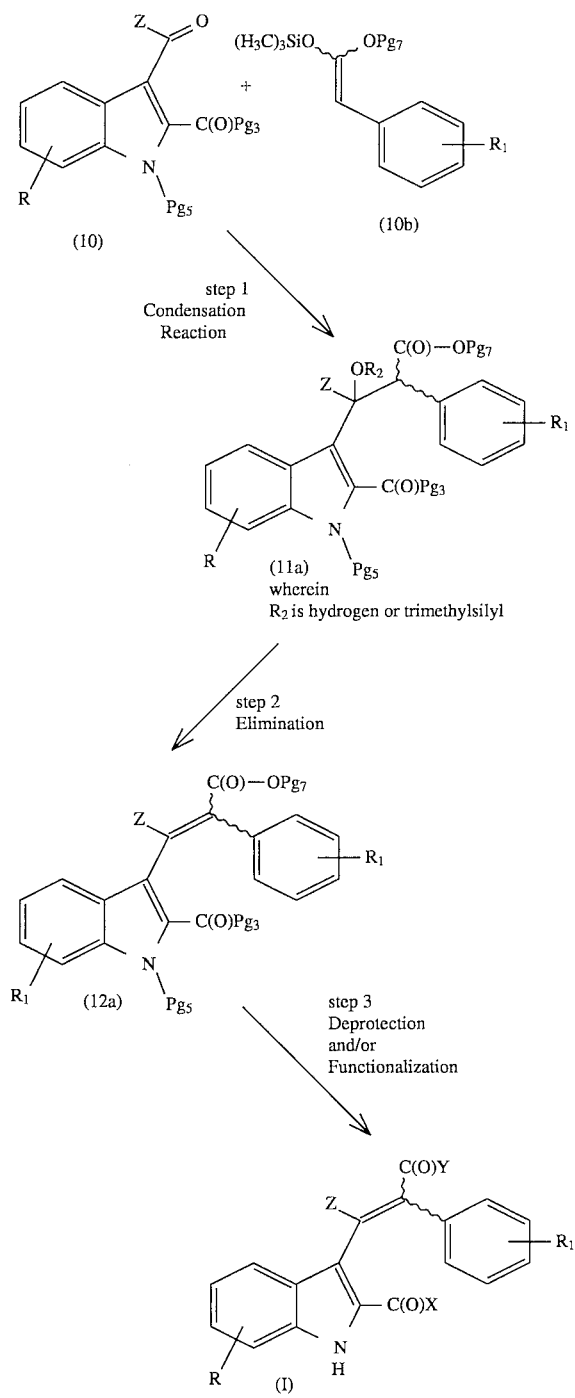

In Reaction Scheme 6, step 1, an appropriate indole of structure (10) is contacted with an appropriate ketene silyl acetal (10b) in a condensation reaction to give a 2-aryl-3-(indol-3-yl)propanoic ester of structure (11a).

An appropriate indole compound of structure (10) is one as defined in Reaction Scheme 3. In Reaction Scheme 6, the use of indole compound of structure (10) in which $Pg_5$ is hydrogen is preferred. An appropriate ketene silyl acetal (10b) is one in which $R_1$ is as desired in the final product of Formula (I) and —OPg$_7$ is Y as desired in the final product of formula (I) or gives rise after deprotection and functionalization as required to Y as desired in the final product of Formula (I). Appropriate ketene silyl acetals (10b) are readily prepared from α-phenylacetic acid esters by reaction with trimethylsilyl chloride or trimethylsilyl triflate in the presence of base as in well known and appreciated in the art and described in H. Emde and G. Simchen, *Synthesis* 867–869 (1977).

For example, an appropriate indole of structure (10) is contacted with an appropriate ketene silyl acetal (10b). The reaction is carried out in a suitable solvent, such as dichloromethane. The reaction is carried out using an appropriate ketene silyl acetal (10b) prepared in diethyl ether and used without isolation after solvent exchange to a suitable solvent, such as dichloromethane. Alternately, an appropriate ketene silyl acetal (10b) prepared in diethyl ether may be isolated by distillation prior to use. The reaction is carried out in presence of a suitable catalyst, such as trimethylsilyl triflate or phosphonium salts as described in T. Mukaiyama et al., *Chem. Lett.*, 993–996 (1989). The reaction is generally carried out at temperatures of from −78° C. to ambient temperature. The reaction generally requires from 1 hour to 12 hours. The product can be isolated by techniques well known in the art, such as extraction and evaporation. The product can then be purified by techniques well known in the art, such as distillation, chromatography, or recrystallization. As is well known and appreciated in the art, depending on the substituents present and the reaction conditions used a condensation reaction of this type may give a propenoic ester of structure (12a) directly.

In Reaction Scheme 6, step 2, an appropriate 2-aryl-3-(indol-3-yl)propanoic ester of structure (11a) in which R$_2$ is hydrogen or trimethylsilyl undergoes an elimination reaction to give propenoic ester of structure (12a) as is well known and appreciated in the art.

For example, an appropriate 2-aryl-3-(indol-3-yl)propanoic ester of structure (11a) in which R$_2$ is hydrogen or trimethylsilyl is contacted with a suitable catalyst, such as p-toluenesulfonic acid or trifluoroacetic acid. The reaction is carried out in a suitable solvent, such as toluene, benzene, or xylene. Generally, the reaction is carried out at temperatures of from ambient temperature to the refluxing temperature of the solvent and require for 1 hour to 2 days. The product can be isolated by techniques well known in the art, such as extraction and evaporation. The product can then be purified by techniques well known in the art, such as distillation, chromatography, or recrystallization.

Alternately, for example, an appropriate 2-aryl-3-(indol-3-yl) propanoic ester of structure (11a) in which R$_2$ is trimethylsilyl is contacted with 1 to 10 molar equivalents of a suitable reagent, such as trifluoromethanesulfonic anhydride in a solvent, such as dichloromethane. The reaction is carried out in the absence of base. Generally, the reaction is carried out at temperatures of from −20° C. to ambient temperature and require for 1 hour to 24 hours. The product can be isolated by techniques well known in the art, such as extraction and evaporation. The product can then be purified by techniques well known in the art, such as distillation, chromatography, or recrystallization.

In Reaction Scheme 6, step 3, a compound of structure (12a) may be optionally protected, deprotected, and functionalized using techniques well known in the art and described in Reaction Scheme 1 to give compounds of Formula (I).

The compounds of Formula (I) are excitatory amino acid antagonists. They antagonize the effects which excitatory amino acids have upon the NMDA receptor complex. They preferentially bind to the strychnine-insensitive glycine binding site on the NMDA receptor complex associated with the treatment of a number of disease states. See Palfreyman, M. G. and B. M. Baron, *Excitatory Amino Acid Antagonists,* B. S. Meldrum ed., Blackwell Scientific, 101–129 (1991); and, Kemp, J. A., and P. D. Leeson, *Trends in Pharmacological Sciences,* 14., 20–25 (1993).

The compounds exhibit anticonvulsant properties and are useful in the treatment of grand mal seizures, petit mal seizures, psychomotor seizures, autonomic seizures, etc. One method of demonstrating their antiepileptic properties is by their ability to exhibit the seizures that are caused by the administration of quinolinic acid. This test can be conducted in the following manner.

One group containing ten mice are administered 0.01–100 micrograms of test compound intracerebroventricularly in a volume of 5 microliters of saline. A second control group containing an equal number of mice are administered an equal volume of saline as a control. Approximately 5 minutes later, both groups are administered 7.7 micrograms of quinolinic acid intracerebroventricularly in a volume of 5 microliters of saline. The animals are observed for 15 minutes thereafter for signs of tonic seizures. The control group will have a statistically higher rate of tonic seizures than will the test group.

Another method of demonstrating the antiepileptic properties of these compounds is by their ability to inhibit audiogenic convulsions in DBA/2J mice. This test can be conducted in the following manner. Typically one group of from 6–8 male DBA/2J audiogenic mice are administered from about 0.01 micrograms to about 10 micrograms of the test compound. The test compound is administered into the lateral ventricle of the brain or intraperitoneally. A second group of mice are administered an equal volume of a saline control by the same route. Five minutes later the mice are placed individually in glass jars and are exposed to a sound of 110 decibels for 30 seconds. Each mouse is observed during the sound exposure for signs of seizure activity. The control group will have a statistically higher incidence of seizures than the group which receives the test compound.

The compounds of Formula (I) are useful for preventing or minimizing the damage which nervous tissues contained within the CNS suffer upon exposure to either ischemic, traumatic, or hypoglycemic conditions including strokes or cerebrovascular accidents, cardiovascular surgery, concussions, hyperinsulinemia, cardiac arrest, drownings, suffocations, and neonatal anoxic trauma. The compounds should be administered to the patient within 24 hours of the onset of the hypoxic, ischemic, traumatic, or hypoglycemic condition in order to minimize the CNS damage which the patient will experience.

The compounds are also useful in the treatment of neurodegenerative diseases such as Huntington's disease, Alzheimer's disease, senile dementia, glutaric acidaemia type I, multi-infarct dementia, amyotrophic lateral sclerosis, and neuronal damage associated with uncontrolled seizures. The administration of these compounds to a patient experiencing such a condition will serve to either prevent the patient from experiencing further neurodegeneration or it will decrease the rate at which the neurodegeneration occurs.

As is apparent to those skilled in the art, the compounds will not correct any CNS damage that has already occurred as the result of either disease, physical injury, or a lack of oxygen or sugar. As used in this application, the term "treat" refers to the ability of the compounds to prevent further damage or delay the rate at which any further damage occurs.

The compounds exhibit an anxiolytic effect and are thus useful in the treatment of anxiety. These anxiolytic properties can be demonstrated by their ability to block distress vocalizations in rat pups. This test is based upon the phenomenon that when a rat pup is removed from its litter, it will emit an ultrasonic vocalization. It was discovered that anxiolytic agents block these vocalizations. The testing methods have been described by Gardner, C. R., Distress Vocalization in Rat Pups: A Simple Screening Method For Anxiolytic Drugs, *J. Pharmacol. Methods*, 14, 181–87 (1986) and Insel et. al., Rat Pup Isolation Calls: Possible Mediation by the Benzodiazepine Receptor Complex, *Pharmacol. Biochem. Behav.*, 24, 1263–67 (1986).

The compounds also exhibit an analgesic effect and are useful in controlling pain. The compounds are also effective in the treatment of migraine.

In order to exhibit these therapeutic properties, the compounds need to be administered in a quantity sufficient to inhibit the effect which the excitatory amino acids have upon the NMDA receptor complex. The dosage range at which these compounds exhibit this antagonistic effect can vary widely depending upon the particular disease being treated, the severity of the patient's disease, the patient, the particular compound being administered, the route of administration, and the presence of other under lying disease states within the patient, etc. Typically the compounds exhibit their therapeutic effect at a dosage range of from about 0.1 mg/kg/day to about 50 mg/kg/day for any of the diseases or conditions listed above. Repetitive daily administration may be desirable and will vary according to the conditions outlined above.

The compounds of the present invention may be administered by a variety of routes. They are effective if administered orally. The compounds may also be administered parenterally (i.e. subcutaneously, intravenously, intramuscularly, intraperitoneally, or intrathecally).

Pharmaceutical compositions can be manufactured utilizing techniques known in the art. Typically a therapeutic amount of the compound will be admixed with a pharmaceutically acceptable carrier.

For oral administration, the compounds can be formulated into solid or liquid preparations such as capsules, pills, tablets, lozenges, melts, powders, suspensions, or emulsions. Solid unit dosage forms can be capsules of the ordinary gelatin type containing, for example, surfactants, lubricants and inert fillers such as lactose, sucrose, and cornstarch or they can be sustained release preparations.

In another embodiment, the compounds of Formula (I) can be tableted with conventional tablet bases such as lactose, sucrose, and cornstarch, in combination with binders, such as acacia, cornstarch, or gelatin, disintegrating agents such as potato starch or alginic acid, and a lubricant such as stearic acid or magnesium stearate. Liquid preparations are prepared by dissolving the active ingredient in an aqueous or nonaqueous pharmaceutically acceptable solvent which may also contain suspending agents, sweetening agents, flavoring agents, and preservative agents as are known in the art.

For parenteral administration the compounds may be dissolved in a physiologically acceptable pharmaceutical carrier and administered as either a solution or a suspension. Illustrative of suitable pharmaceutical carriers are water, saline, dextrose solutions, fructose solutions, ethanol, or oils of animal, vegetative, or synthetic origin. The pharmaceutical carrier may also contain preservatives, buffers, etc., as are known in the art. When the compounds are being administered intrathecally, they may also be dissolved in cerebrospinal fluid as is known in the art.

The compounds of this invention can also be administered topically. This can be accomplished by simply preparing a solution of the compound to be administered, preferably using a solvent known to promote transdermal absorption such as ethanol or dimethyl sulfoxide (DMSO) with or without other excipients. Preferably topical administration will be accomplished using a patch either of the reservoir and porous membrane type or of a solid matrix variety.

Some suitable transdermal devices are described in U.S. Pat. Nos. 3,742,951; 3,797,494; 3,996,934; and 4,031,894. These devices generally contain a backing member which defines one of its face surfaces, an active agent permeable adhesive layer defining the other face surface and at least one reservoir containing the active agent interposed between the face surfaces. Alternatively, the active agent may be contained in a plurality of microcapsules distributed throughout the permeable adhesive layer. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane.

In another device for transdermally administering the compounds in accordance with the present invention, the pharmaceutically active compound is contained in a matrix from which it is delivered in the desired gradual, constant and controlled rate. The matrix is permeable to the release of the compound through diffusion or microporous flow. The release is rate controlling. Such a system, which requires no membrane is described in U.S. Pat. No. 3,921,636. At least two types of release are possible in these systems. Release by diffusion occurs when the matrix is nonporous. The pharmaceutically effective compound dissolves in and diffuses through the matrix itself. Release by microporous flow occurs when the pharmaceutically effective compound is transported through a liquid phase in the pores of the matrix.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art.

As used in this application:

k) the "patient" refers to warm blooded animals such as, for example guinea pigs, mice, rats, cats, rabbits, dogs, monkeys, chimpanzees, and human;

l) the term "treat" refers to the ability of the compounds to either relieve, alleviate, or slow the progression of the patient's disease;

m) the term "neurodegeneration" refers to a progressive death and disappearance of a population of nerve cells occurring in a manner characteristic of a particular disease state and leading to brain damage.

The compounds of Formula (I) may also be admixed with any inert carrier and utilized in laboratory assays in order to determine the concentration of the compound within the serum, urine, etc., of the patient as is known in the art.

Neurodegeneration diseases are typically associated with a loss of NMDA receptors. Thus, the compounds of Formula (I) may be utilized in diagnostic procedures to aid physicians with the diagnosis of neurodegenerative diseases. The compounds may be labeled with imaging agents known in the art such as isotopic ions and administered to a patient in order to determine whether the patient is exhibiting a decreased number of NMDA receptors and the rate at which that loss is occurring.

The following preparations represent typical procedures for preparing starting materials used in the examples. The following examples present typical syntheses as described in Reaction Scheme 1, Reaction Scheme 2, and Reaction Scheme 3, and Reaction Scheme 4. These preparations and examples are understood to be illustrative only and are not intended to limit the scope of the invention in any way. As used in the following preparations and examples, the following terms have the meanings indicated: "g" refers to grams, "mg" refers to milligrams, "mmol" refers to millimoles, "mol" refers to moles, "mL" refers to milliliters, "L" refers to liters, "° C." refers to degrees Celsius, "M" refers to molar, "mp" refers to melting point, "dec" refers to decomposition, "THF" refers to tetrahydrofuran, "$R_f$" refers to retention factor, "ether" refers to diehyl ether, unless otherwide indicated.

PREPARATION 1

4,6-Dichloro-3-iodoindole-2-carboxylic acid, ethyl ester

Combine 4,6-dichloro-indole-2-carboxylic acid, ethyl ester (5.2 g, 20.0 mmol) and sodium hydroxide (0.80 g, 20 mmol) in ethanol (250 mL). Add iodine (5.1 g, 20.0 mmol) as a solution in ethanol (100 mL). After 1 hour, concentrate the reaction mixture in vacuo to obtain a residue. Dissolve the residue in ethyl acetate and extract with 1M hydrochloric acid solution and then with saturated sodium chloride solution. Dry the organic layer over magnesium sulfate and evaporate in vacuo. Chromatograph on silica gel eluting with 25% ethyl acetate/hexane. Combine the product containing fractions and evaporate in vacuo. Recrystallize form ethyl acetate/hexane to give the title compound as a solid; mp: 218°–220° C. Elem. Anal. calculated for $C_{11}H_8Cl_2INO_2$: C, 34.41; H, 2.10; N, 3.65. Found: C, 34.67; H, 2.09; N, 3.68.

PREPARATION 2

Ethyl 4-(N,N'-(1,1,4,4-tetramethyl-1,4-disilethyleneamino)benzoylformate

Combine magnesium turnings (12 mmol) and 1,2-dibromoethane (2 mmol) in anhydrous diethyl ether (500 mL). Heat to a gentle reflux and slowly add a solution of 4-bromo-N,N'-(1,1,4,4-tetramethyl-1,4-disilethylene)aniline (T. L. Guggenheim, *Tet. Lets.* 25, 1253–1254 (1984)) (10 mmol) in diethyl ether (100 mL). Heat until the magnesium turnings have reacted. Cool to 0° C. Add ethyl α-oxo-1H-imidazole-1-acetate (J. S. Nimitz and H. S. Mosher *JOC* 46, 211–213, (1981)) (10 mmol). After the addition is complete, warm to ambient temperature. After 18 hours, pour the reaction mixture into a cold ammonium chloride solution. Extract with ethyl acetate and combine the organic layers. Dry over magnesium sulfate and evaporate in vacuo. Chromatograph on silica gel to give the title compound.

PREPARATION 3 a) 2-Phenyl-3-(tri-n-butylstannyl),propenoic acid, methyl ester

Combine diethyl phenylsulphonylmethylphosphonate (T. A. Blumenkopf *Synth. Commun.* 26, 139–147, (1986)) (117.0 g, 400 mmol) and tetrahydrofuran (500 mL). Cool in an ice-bath. Add lithium bis(trimethylsilyl)amide (480 mL, 1M in tetrahydrofuran, 480 mmol). Stir for 30 minutes after the addition of lithium bis(trimethylsilyl)amide, then add methyl benzoylformate (72.0 g, 439 mmol). Warm to ambient temperature and stir for 2 hours. Partition between water and ethyl acetate. Extract the aqueous layer with ethyl acetate. Combine the organic layers, dry over magnesium sulfate and evaporate in vacuo to give an oil. Triturate with cyclohexane to give a solid. Chromatograph the solid on silica gel eluting sequentially with 10% ethyl acetate/hexane, 15% ethyl acetate/hexane, and 33% ethyl acetate/hexane. Evaporation of the product containing fractions give a solid. Recrystallize form ethyl acetate/hexane to give 2-phenyl-3-sulfonylphenyl-propenoic acid, methyl ester as a solid. Elem. Anal calculated for $C_{16}H_{14}O_4S$: C, 63.56; H, 4.67. Found: C, 63.25; H, 4.70.

Combine 2-phenyl-3-sulfonlyphenyl-propenoic acid, methyl ester (41.0 g, 136 mmol) and tri-n-butyltin hydride (79.0 g, 271 mmol) in cyclohexane (900 mL). Add 2,2'-azobisisobutyronitrile (AIBN) (0.7 g, 4.3 mmol) and heat to reflux for 3 hours. Cool to ambient temperature and evaporate in vacuo. Chromatograph on silica gel eluting with 20% ethyl acetate/hexane. Evaporate the product containing fractions and chromatograph on silica gel eluting sequentially with 5% ethyl acetate/hexane and 10% ethyl acetate/hexane to give the title compound and a clear oil.

b) 2-Phenyl-3-(tri-n-butylstannyl)-propenoic acid, ethyl ester can be prepared by the method of Preparation 3 by using ethyl benzoylformate (J. S. Nimitz and H. S. Mosher *JOC* 46, 211–213, (1981)).

c) 2-Phenyl-3-(tri-n-butylstannyl)-propenoic acid, ethyl ester can be prepared by the method of Preparation 3 by using ethyl benzoylformate (J. S. Nimitz and H. S. Mosher *JOC* 46, 211–213, (1981)).

d) 2-(4-Methylphenyl)-3-(tri-n-butylstannyl)-propenoic acid, t-butyl ester can be prepared by the method of Preparation 3 by using t-butyl 4-methylbenzoylformate (J. S. Nimitz and H. S. Mosher *JOC* 46, 211–213, (1981)).

e) 2-(4-Chlorophenyl)-3-(tri-n-butylstannyl)-propenoic acid, t-butyl ester can be prepared by the method of Preparation 3 by using t-butyl 4-chlorobenzoylformate (J. S. Nimitz and H. S. Mosher *JOC* 46, 211–213, (1981)).

f) 2-(4-Methoxyphenyl)-3-(tri-n-butylstannyl-propenoic acid, t-butyl ester can be prepared by the method of Preparation 3 by using t-butyl 4-methoxybenzoylformate (J. S. Nimitz and H. S. Mosher *JOC* 46, 211–213, (1981)).

g) 2-(N,N'-(1,1,4,4-Tetramethyl-1,4-disilethylenaeminophenyl)-3-(tri-n-butylstannyl)-propenoic acid, t-butyl ester can be prepared by the method of Preparation 3 by using t-butyl 4-(N,N'-(1,1,4,4-tetramethyl-1,4-disilethyleneamino)benzoylformate prepared as in Preparation 2 using t-butyl benzoylformate (J. S. Nimitz and H. S. Mosher *JOC* 46, 211–213, (1981)).

h) 2-(4-Methylphenyl)-3-(tri-n-butylstannyl)-propenoic acid, ethyl ester can be prepared by the method of Preparation 3 by using ethyl 4-methylbenzoylformate (J. S. Nimitz and H. S. Mosher *JOC* 46, 211–213, (1981)).

i) 2-(4-Chlorophenyl)-3-(tri-n-butylstannyl)-propenoic acid, ethyl ester can be prepared by the method of Preparation 3 by using ethyl 4-chlorobenzoylformate (J. S. Nimitz and H. S. Mosher *JOC* 46, 211–213, (1981)).

j) 2-(4-Methoxyphenyl)-3-(tri-n-butylstannyl)-propenoic acid, ethyl ester can be prepared by the method of Preparation 3 by using ethyl 4-methoxybenzoylformate (J. S. Nimitz and H. S. Mosher *JOC* 46, 211–213, (1981)).

k) 2-(4-N,N'-(1,1,4,4-Tetramethyl-1,4-disilethyleneaminophenyl)-3-(tri-n-butylstannyl)-propenoic acid, ethyl ester

27 can be prepared by the method of Preparation 3 by using ethyl 4-(N,N'-(1,1,4,4-tetramethyl-1,4-disilethyleneamino)benzoylformate as prepared in Preparation 2.

EXAMPLE 1

(E) and (Z)-2-Phenyl-3-(2-carboethoxy-4,6-dichloroindol-3-yl)-propenoic acid, ethyl ester

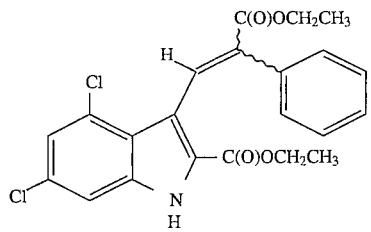

Combine 4,6-dichloro-3-iodoindole-2-carboxylic acid, ethyl ester (1.5g, 3.9 mmol) and 2-phenyl-3-(tri-n-butylstannyl)-propenoic acid, ethyl ester (1.1g, 2.4 mmol) in 1-methyl-2-pyrrolidinone (5 mL) and add bis-acetonitrilepalladium (II) dichloride (2.07 mg, 0.08 mmol). Flush the vessel with nitrogen gas seal and heat to 60° C. After stirring for 8 hours add more bis-(acetonitrile)palladium (II) dichloride (2.07 mg, 0.08 mmol) and continue stirring for 16 hours. Pour the reaction mixture into water and extract with diethyl ether, dry over magnesium sulfate and evaporate in vacuo. Chromatograph on silica gel eluting with 15% ethyl acetate/hexane to give 0.60 g of the title compound; mp: 179°–182° C. Elem. Anal. calculated for $C_{22}H_{19}Cl_2NO_4$: C, 61.12; H, 4.43; N, 3.24. Found: C, 60.84; H, 4.33; N, 3.17.

EXAMPLE 2

(E) and (Z)-2-Phenyl-3-(2-carboethoxy-4,6-dichloroindol-3-yl)-propenoic acid, ethyl ester

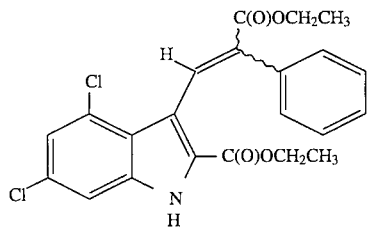

Combine 4,6-dichloro-indole-2-carboxylic acid, ethyl ester (1.50 g, 4.0 mmol) and palladium (II) diacetate (0.90 g, 4.0 mmol) in trifluoroacetic acid (5 mL) and heat at 50° C. for 0.5 hours to dissolve the solids. Add 2-phenyl-propenoic acid, ethyl ester (1.5g, 8.5 mmol) and stir at 50° C. for 16 hours. Remove the solid by evaporation in vacuo and dilute the residue with ethyl acetate and extract with saturated sodium bicarbonate solution. Chromatograph on silica gel eluting with 15% ethyl acetate/hexane to give 0.40 g of the title compound; mp: 164°–168° C. Elem. Anal. Calculated. for $C_{22}H_{19}Cl_2NO_4$: C, 61.12; H, 4.43; N, 3.24. Found: C, 60.82; H, 4.43; N, 3.16.

28

EXAMPLE 3

(E)-2-Phenyl-3-(4,6-dichloroindol-3-yl-2-carboxylic acid)-propenoic acid

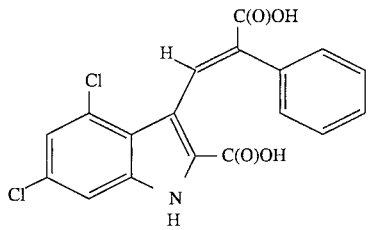

Combine (E) and (Z)-2-phenyl-3-(2-carboethoxy-4,6-dichloroindo-3-yl)-propenoic acid, ethyl ester (65 mg, 0.16 mmol) and lithium hydroxide (20.2 mg, 0.48 mmol) in THF/water (3 mL, 1/1) and heat to 50° C. for 24 hours. Dilute the reaction mixture with water (5 mL) and acidify with 1M hydrochloric acid. Extract with ethyl dry the organic layer with magnesium sulfate. Evaporate in vacuo and recrystallize the residue from ethyl acetate/hexane to give 57 mg of the title compound; mp: 268°–270° C. (dec). Elem. Anal. Calculated. for $C_{18}H_{11}Cl_2NO_4$(0.5 ethyl acetate): C, 57.16; H, 3.60; N, 3.33. Found: C, 56.95; H, 3.67; N, 3.29.

EXAMPLE 4

(E) and (Z)-2-Phenyl-3-(2-carboethoxy-5,6-dichloroindol-3-yl)-propenoic acid, ethyl ester

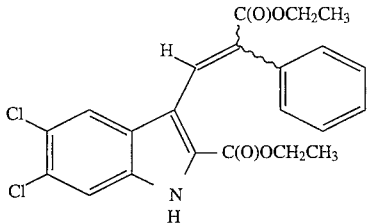

Combine 5,6-dichloro-3-iodoindole-2-carboxylic acid, ester ester (1.5g, 3.9 mmol) and 2-phenyl-3-(tri-n-butylstannyl)-propenoic acid, ethyl ester (1g, 2.4 mmol) in 1-methyl-2-pyrrolidinone (5 mL) and add bis-(acetonitrile)palladium (II) dichloride (2.07 mg, 0.08 mmol). Flush the vessel with nitrogen gas seal and heat to 0° C. After stirring for 5 hours, pour the reaction mixture into water and extract with diethyl ether, dry over magnesium sulfate and evaporate in vacuo. Chromatograph on silica gel eluting with 15% ethyl acetate/hexane to give 0.85 g of the title compound.

EXAMPLE 5

(E)-2-phenyl-3-(5,6-dichloroindol-3-yl-2-carboxylic acid)-propenoic acid

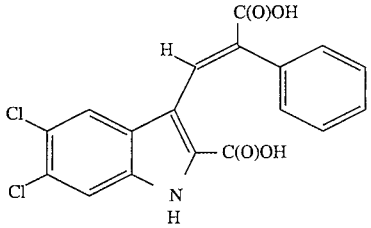

Combine (E) and (Z)-2-phenyl-3-(2-carboethoxy-5,6-dichloroindo-3-yl)-propenoic acid, ethyl ester (850 mg, 1.7 mmol) and lithium hydroxide hydrate (508 mg, 12.1 mmol) in THF/water (20 mL, 1/1) and heat to 50° C. for 24 hours. Dilute the reaction mixture with water (50 mL) and acidify with 1M hydrochloric acid. Extract with ethyl acetate and dry the organic layer with magnesium sulfate. Evaporate in vacuo and recrystallize the residue from ethyl acetate/hexane to give 330 mg of the title compound; mp: 272°–276° C. (dec). Elem. Anal. Calculated. for $C_{18}H_{11}Cl_2NO_4$(0.25 ethyl acetate) (0.5): C, 56.04; H, 3.46; N, 3.45. Found: C, 56.07; H, 3.37; N, 3.60.

EXAMPLE 6

(E) and (Z)-N-Methyl-2-phenyl-3-(2-carbomethylamino-4,6-dichloroindol-3-yl)propenoic amide

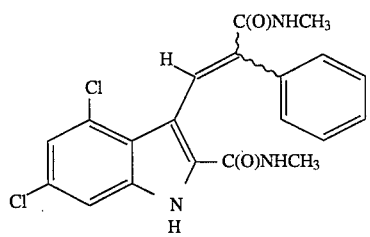

Combine (E) and (Z)-2-phenyl-3-(2-carboethoxy-4,6-dichloroindo-3-yl)-propenoic acid, ethyl ester in THF/water (3 mL, 1/1) bubble in an excess of methylamine gas, seal and stir for 24 hours. Dilute the reaction mixture with water (5 mL) and acidify with 1N hydrochloric acid. Extract with ethyl acetate and dry the organic layer with magnesium sulfate. Evaporate in vacuo and recrystallize the residue to give the title compound.

EXAMPLE 7

(E) and (Z)-2-Phenyl-3-(2-carboethoxy-6-chloroindol-3-yl)-propenoic acid, ethyl ester

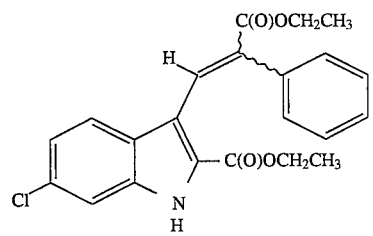

Combine 6-chloro-3-iodoindole-2-carboxylic acid, ethyl ester (0.34g, 0.98 mmol) and 2-phenyl-3-(tri-n-butylstannyl)-propenoic acid, ethyl ester (0.44 g, 0.98 mmol) in 1-methyl-2-pyrrolidinone (2 mL) and add bis-acetonitrile-palladium (II) dichloride (2.07 mg, 0.08 mmol). Flush the vessel with nitrogen gas seal and heat to 80° C. After stirring for 5 pour the reaction mixture into water and extract with ethyl acetate, dry over magnesium sulfate and evaporate in vacuo. Chromatograph on silica gel eluting with 1/6 ethyl acetate/hexane to give 0.13 g of the title compound. $R_f$=0.20, silica gel, 1/6 ethyl acetate/hexane.

EXAMPLE 8

(E)-2,Phenyl-3-(6-chloroindol-3-yl-2-carboxylic acid)-propenoic acid

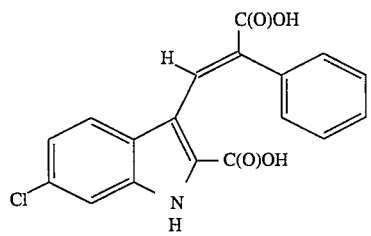

Combine (E) and (Z)-2-phenyl-3-(2-carboethoxy-6-chloroindo-3-yl)-propenoic acid, ethyl ester (123 mg, 0.32 mmol) and an aqueous solution of lithium hydroxide hydrate (2.6 mL, 1.0M, 2.6 mmol) in THF (5 mL) and heat to reflux for 24 hours. Evaporate in vacuo to remove most of the THF. Dilute the reaction mixture with water (50 mL) and extract with ethyl acetate and discard the organic layer. Acidify with aqueous layer with 1M hydrochloric acid. Extract with ethyl acetate (3×75 mL), combine the organic layers, and dry over magnesium sulfate. Evaporate in vacuo and recrystallize the residue from ethyl acetate/hexane to give the title compound; mp: 232°–236° C. (dec).

EXAMPLE 9

(E) and (Z)-2-(4-Methoxyphenyl )-3,(2-carboethoxy-4,6-dichloroindol-3-yl)propenoic acid, ethyl ester

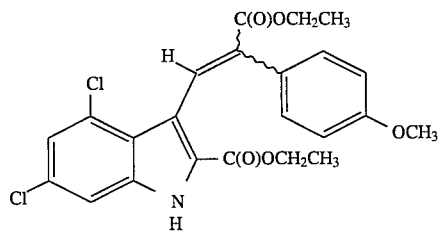

Combine 4,6-dichloro-3-iodoindole-2-carboxylic acid, ethyl ester (4.0 mmol) and 2-(4-methoxyphenyl)-3-(tri-n-butylstannyl)-propenoic acid, ethyl ester (2.5 mmol) in 1-methyl-2-pyrrolidinone (5 mL) and add bis-acetonitrile-palladium (II) dichloride (0.08 mmol). Flush the vessel with nitrogen gas seal and heat to 60° C. After stirring for 8 hours add more bis-(acetonitrile)palladium (II) dichloride (2.07 mg, 0.08 mmol) and continue stirring for 16 hours. Pour the reaction mixture into water and extract with diethyl ether, dry over magnesium sulfate and evaporate in vacuo. Chromatograph on silica gel to give the title compound.

EXAMPLE 10

(E) and (Z)-2-(4-Methylphenyl)-3-(2-carboethoxy-4,6-dichloroindol-3-yl)propenoic acid, ethyl ester

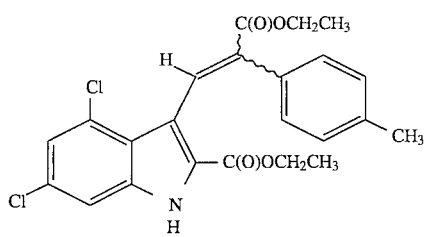

Prepare by the method of Example 9 using 2-(4-methylphenyl)-3-(tri-n-butylstannyl)-propenoic acid, ethyl ester.

EXAMPLE 11

(E) and (Z)-2-(4-Chlorophenyl)-3-(2-carboethoxy-4,6-dichloroindol-3-yl)-propenoic acid, ethyl ester

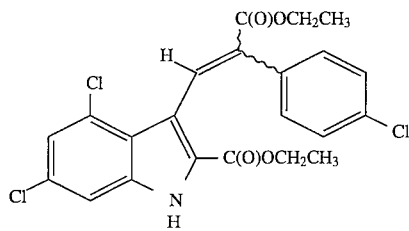

Prepare by the method of Example 9 using 2-(4-chlorophenyl)-3-(tri-n-butylstannyl)-propenoic, ethyl ester.

EXAMPLE 12

(E) and (Z)-2-(4-N,N'-(1,1,4,4-Tetramethyl-1,4-disilethyleneaminophenyl)-3-(2-carboethoxy-4,6-dichloroindol-3-yl)-propenoic acid, ethyl ester

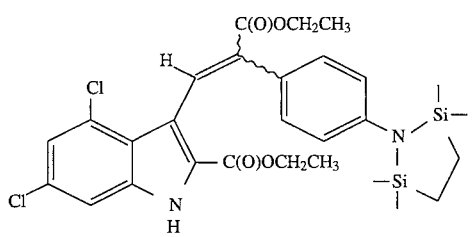

Prepare by the method of Example 9 using 2-(4-N,N'-(1,1,4,4-tetramethyl-1,4-disilethyleneaminophenyl)-3-(tri-n-butylstannyl)-propenoic acid, ethyl ester.

EXAMPLE 13

(E) and (Z)-2-Phenyl-3-(2-carboethoxy-4,6-dichloroindol-3-yl)-propenoic acid, t-butyl ester

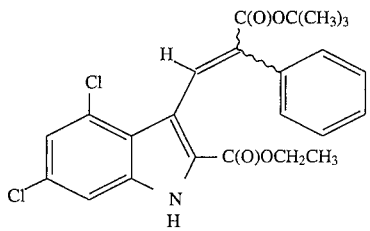

Prepare by the method of Example 9 using 2-phenyl-3-(tri-n-butylstannyl)-propenoic acid, t-butyl ester.

EXAMPLE 14

(E) and (Z)-2-(4-Methoxyphenyl)-3-(4,6-dichloroindol-3-yl-2-carboxylic acid)propenoic acid

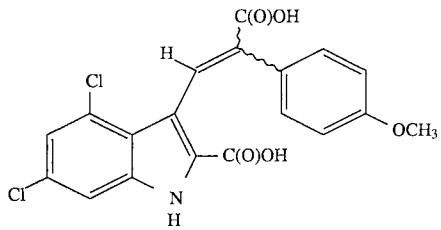

Prepare by the method of Example 3 using (E) and (Z)-2-(4-methoxyphenyl)-3-(2-carboethoxy-4,6-dichloroindol-3-yl)propenoic acid, ethyl ester.

EXAMPLE 15

(E) and (Z)-2-(4-Methylphenyl)-3-(4,6-dichloroindol-3-yl–2-carboxylic acid)propenoic acid

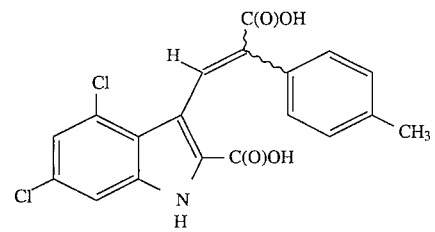

Prepare by the method of Example 3 using (E) and (Z)-2-(4-methylphenyl)-3-(2-carboethoxy-4,6-dichloroindol-3-yl)propenoic acid, ethyl ester.

EXAMPLE 15.1

(E) and (Z)-2-(4-Methylphenyl)-3-(4,6-dichloroindol-3-yl-2-carboxylic acid)propenoic acid Combine (E) and (Z)-2-(4-methylphenyl)-3-(2-carboethoxy-4,6-dichloroindol-3-yl)-propenoic acid, methyl ester (2.73 g, 6.32 mmol), tetrahydrofuran (38 mL), methanol (19 mL), and aqueous 1M sodium hydroxide solution (37.9 mL). Heat to reflux. After 18 hours, cool the reaction mixture to 0° C. and acidify with 1M hydrochloric acid solution to give a solid. Collect the solid by filtration. Recrystallize from ethyl acetate/cyclohexane, filter, and dry to give the title compound.

EXAMPLE 16

(E) and (Z)-2-(4-Chlorophenyl)-3-(4,6-dichloroindol-3-yl-2-carboxylic acid)propenoic acid

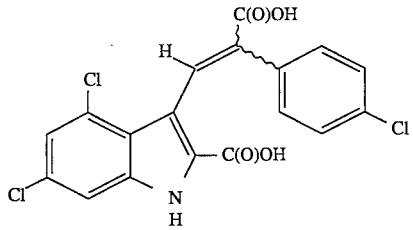

Prepare by the method of Example 3 using (E) and (Z)-2-(4-chlorophenyl)-3-(2-carboethoxy-4,6-dichloroindol-3-yl)propenoic acid, ethyl ester.

EXAMPLE 17

(E) and (Z)-2,(4-Aminophenyl)-3-(2-carboethoxy-4-dichloroindol-3-yl)propenoic acid, ethyl ester

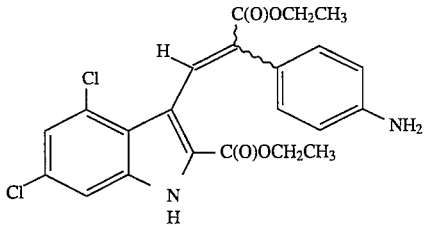

Combine (E) and (Z)-2-(4-N,N'-(1,1,4,4-tetramethyl-1,4-disilethyleneaminophenyl)-3-(2-carboethoxy-4,6-dichloroindol-3-yl)propenoic acid, ethyl ester (2 mmol) and ethanol (10 mL). Cool to 0° C. in an ice-bath and add 2M hydrochloric acid solution (0.5 mL). After 1 hour, partition the reaction mixture between saturated sodium bicarbonate solution and dichloromethane. Extract the aqueous layer with dichloromethane and combine the organic layers. Dry the organic layers over magnesium sulfate, filter, and evaporate in vacuo to give the title compound.

EXAMPLE 18

(E) and (Z)-2-(4-Aminophenyl)-3-(4,6-dichloroindol-3-yl-2-carboxylic acid)propenoic acid

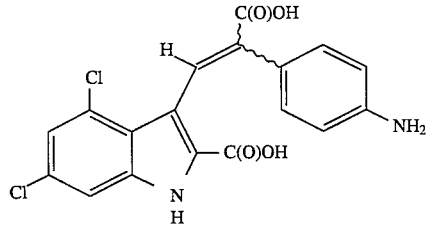

Prepare by the method of Example 3 using (E) and (Z)-2-(4-Aminophenyl)-3-(2-carboethoxy-4,6-dichloroindol-3-yl)propenoic acid, ethyl ester.

EXAMPLE 19

(E) and (Z)-2-Phenyl-3-(1-p-toluenesulfonyl-2-carboethoxy-4,6-dichloroindol-3-yl)-propenoic acid, t-butyl ester

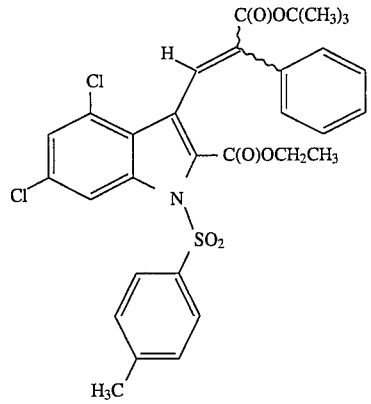

Combine (E) and (Z)-2-phenyl-3-(2-carboethoxy-4,6-dichloroindol-3-yl)-propenoic acid, t-butyl ester (5 mmol) and sodium hydride (5 mmol) in tetrahydrofuran (10 mL) and allow to stir until gas evolution ceases. Add p-toluenesulfonyl chloride (6 mmol). After 24 hour, pour the reaction mixture into water and extract with ethyl acetate. Dry the organic layer over magnesium sulfate, filter, and evaporate in vacuo. Chromatograph on silica gel to give the title compound.

EXAMPLE 20

(E) and (Z)-2-Phenyl-3-(1-p-toluenesulfonyl-2-carboethoxy-4,6-dichloroindol-3-yl)-propenoic acid

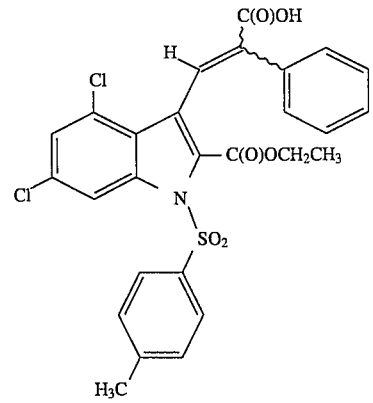

Cool a solution trifluoroacetic acid (5 mL) and anisole (2 mmol) in dichloromethane (10 mL) in an ice-bath. Add (E) and (Z)-2-phenyl-3-(1-p-toluenesulfonyl-2-carboethoxy-4,6-dichloroindol-3-yl)-propenoic acid, t-butyl ester (1 mmol) and stir for 3 hours. Evaporate in vacuo. Repeatedly, add carbon tetrachloride and evaporate in vacuo to remove residual trifluoroacetic acid. Triturate with hexane to give the title compound.

EXAMPLE 20.1

(E) and (Z)-2-Phenyl-3-(1-p-toluenesulfonyl-2-carboethoxy-4,6-dichloroindol-3-yl)-propenoic acid Combine (E) and (Z)-2-Phenyl-3-(1-p-toluenesulfonyl-2-carboethoxy-4,6-dichloroindol-3-yl)-Propenoic acid (4.3 g, 7.0 mmol) and dichloromethane (150 mL). Add trifluoroacetic acid (50 mL). After 3 hours, concentrate in vacuo to obtain a residue. Dissolve the residue in dichloromethane and extract twice with water. Dry the organic layer over MgSO$_4$, filter, and concentrate in vacuo to give the title compound: $^1$H NMR (CDCl$_3$) δ9.48 (br s, 1H), 8.09 (s, 1H), 7.91 (s, 1H), 7.62 (d, 2H, J=8.4 Hz), 7.27–7.07 (m, 8H), 4.14 (q, 2H, J=7.2 Hz), 2.38 (s, 3H), 1.22 (t, 3H, J=7.1 Hz).

EXAMPLE 21

(E) and (Z)-2-Phenyl-3-(1-p-toluenesulfonyl-2-carboethoxy-4,6-dichloroindol-3-yl)-propenoic acid chloride

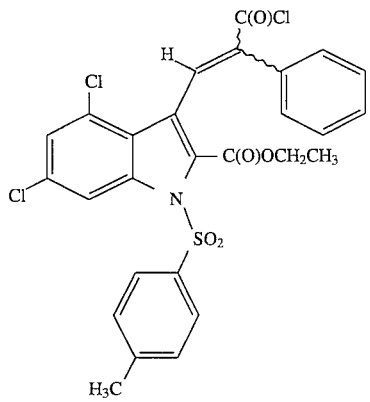

Combine (E) and (Z)-2-phenyl-3-(1-p-toluenesulfonyl-2-carboethoxy-4,6-dichloroindol-3-yl)-propenoic acid (5mmol) and oxalyl chloride (20 mL). Add dimethylformamide (0.1 mL) and heat to reflux. After 4 hours, evaporate in vacuo. Add hexane and evaporate in vacuo to give the title compound.

EXAMPLE 21.1

(E) and (Z)-2-Phenyl-3-(1-p-toluenesulfonyl-2-carboethoxy-4,6-dichloroindol-3-yl)-propenoic acid chloride Combine (E) and (Z)-2-phenyl-3-(1-p-toluenesulfonyl-2-carboethoxy-4,6-dichloroindol-3-yl)-propenoic acid (0.80 g, 1.43 mmol) and dichloromethane (20 mL). Add dimethylformamide (5 drops). Slowly add oxalyl chloride (0.16 mL, 1.86 mmol). After 4 hours, add oxalyl chloride (0.16 mL, 1.86 mmol). After 4 more hours, add oxalyl chloride (0.16 mL, 1.86 mmol). After 16 hours, evaporate in vacuo. Add hexane and evaporate in vacuo to give the title compound.

EXAMPLE 22

(E) and (Z)-N,N-Dimethyl-2-phenyl-3-(1-p-toluenesulfonyl-4,6-dichloroindol-3-yl-2-carboethoxy)propenoic amide Combine (E) and (Z)-2-phenyl-3-(1-p-toluenesulfonyl-2-carboethoxy-4,6-dichloroindol-3-yl)-propenoic acid chloride and tetrahydrofuran. Cool in an ice-bath. Add triethylamine (6 mmol). Add dimethylamine as a gas by slowly bubbling a stream of dimethylamine gas into the solution for 20 minutes. Warm to ambient temperature and stir for 24 hours. Evaporate in vacuo to give a residue. Partition the residue between 1M hydrochloric acid solution and ethyl acetate. Extract the aqueous layer with ethyl acetate. Dry the combined organic layers over magnesium sulfate, filter, and evaporate in vacuo. Chromatograph on silica gel to give the title compound.

EXAMPLE 22.1

(E) and (Z)-N,N-Dimethyl-2-phenyl-3-(1-p-toluenesulfonyl-4,6-dichloroindol-3-yl-2-carboethoxy)propenoic amide Combine (E) and (Z)-2-phenyl-3-(1-p-toluenesulfonyl-2-carboethoxy-4,6-dichloroindol-3-yl)-propenoic acid (0.81 g, 1.5 mmol), 1-hydroxybenzotriazole hydrate (232 mg, 1.72 mmol), triethylamine (0.24 mL, 1.7 mmol), and 1-(dimethylaminopropyl)-3-ethylcarbodiimide hydrochloride (330 mg, 1.72 mmol) in dichloromethane (5 mL). Add dimethylamine hydrochloride (1.72 mmol). After 3 hours, dilute the reaction mixture with water and extract with ethyl acetate. Separate the organic layer, extract with water and concentrate in vacuo to give residue. Chromatograph the residue on silica gel eluting with 3/2 cyclohexane/ethyl acetate to give a residue. Recrystallize that residue from ether/cyclohexane to give the title compound: mp 73°–81° C; IR (KBr) vmax 1732, 1638, 1389, 1371, 1269, 1196, 1177, 1007, 581 cm$^{-1}$; $^1$H NMR (CDCl$_3$) δ7.95 (d, 1H, J=1.7 Hz), 7.73 (m, 1H), 7.69 (m, 1H), 7.3–7.1 (m, 8H), 6.99 and 6.69 (s, 1H), 4.14 (q, 2H, J=7.2 Hz), 3.06 and 3.04 and 3.00 (s, 6H), 2.39 (s, 3H), 1.34 and 1.25 (t, 3H J=7.2 Hz). Elemental Analysis Calculated for C$_{29}$H$_{26}$Cl$_2$N$_2$O$_5$S: C, 59.49; H, 4.48; N, 4.78. Found: C, 60.87; H, 5.14; N, 4.67.

EXAMPLE 23

(E) and (Z)-N-Methyl-2-phenyl-3-(1-p-toluenesulfonyl-4,6-dichloroindol-3-yl-2-carboethoxy)propenoic amide Prepare by the method of Example 22 using methylamine as a gas.

EXAMPLE 23.1

(E) and (Z)-N-Methyl-2-phenyl-3-(1-p-toluenesulfonyl-4,6-dichloroindol-3-yl-2-carboethoxy)propenoic amide Combine (E) and (Z)-2-phenyl-3-(1-p-toluenesulfonyl-2-carboethoxy-4,6-dichloroindol-3-yl)-propenoic acid (800 mg, 1.43 mmol) 1-hydroxybenzotriazole hydrate (232 mg, 1.72 mmol), triethylamine (0.24 mL, 1.7 mmol), and 1-(dimethylaminopropyl)-3-ethylcarbodiimide hydrochloride (330 mg, 1.72 mmol) in dichloromethane (5 mL). Add methylamine hydrochloride (116 mg, 1.72 mmol). After 3 hours, dilute the reaction mixture with water and extract with ethyl acetate. Separate the organic layer, extract with water and concentrate in vacuo to give residue. Chromatograph the residue on silica gel eluting with 2/1 hexane/ethyl acetate to give a residue. Recrystallize that residue from ethyl acetate to give the title compound: IR (KBr) vmax 3441, 1722, 1514, 1383, 1370, 1267, 1204, 1194, 182 cm$^{-1}$; $^1$H NMR (DMSO-d$_6$) δ7.84 (m, 1H), 7.65 (d, 2H, J=8.6 Hz), 7.58 (m, 1H), 7.53 (m, 1H), 7.41 (d, 2H, J=8.6 Hz), 7.33 (s, 1H), 7.26–7.12 (m, 3H), 6.93 (m, 2H), 4.10 (q, 2H, J=7.2 Hz), 2.69 (d, 3H, J=4.6 Hz), 2.37 (s, 3 H), 1.13 (t, 3H, J=7.1 Hz). Elemental Analysis Calculated for C$_{28}$H$_{24}$Cl$_2$N$_2$O$_5$S: C, 58.85; H, 4.23; N, 4.90. Found: C, 58.82; H, 4.17; N, 4.76.

EXAMPLE 24

(E) and (Z)-N-Phenyl-2-phenyl-3-(1-p-toluenesulfonyl-4,6-dichloroindol-3-yl-2-carboethoxy)propenoic amide Prepare by the method of Example 22 using aniline.

EXAMPLE 24.1

(E) and (Z)-N-Phenyl-2-phenyl-3-(1-p-toluenesulfonyl-4,6-dichloroindol-3-yl-2-carboethoxy)propenoic amide Combine (E) and (Z)-2-phenyl-3-(1-p-toluenesulfonyl-2-carboethoxy-4,6-dichloroindol-3-yl)-propenoic acid (0.34 g, 0.61 mmol) and dichloromethane (20 mL). Add thionyl chloride (0.05 mL, 0.67 mmol). After 15 minutes, add aniline (0.064 mL, 0.67 mmol). After 2 hours, dilute with dichloromethane, extract with water and then with aqueous 1M hydrochloric acid solution. Separate the organic layer, dry over $MgSO_4$, and concentrate in vacuo to a residue. Chromatograph the residue on silica gel eluting with 3/1 hexane/ether to give the title compound as a solid: mp 84°–85° C.; $^1$H NMR ($CDCl_3$) δ7.90 (d, 2H, J=7.9 Hz), 7.61 (d, 2H, J=8.4 Hz), 7.49 (d, 2H, J=8.4 Hz), 7.33–7.11 (m, 12H), 4.21 (q, 2H, J=7.1 Hz), 2.39 (s, 3H), 1.28 (t, 3H, J=7.1 Hz). Elemental Analysis Calculated for $C_{33}H_{26}Cl_2N_2O_5S$: C, 62.56; H, 4.14; N, 4.42. Found: C, 60.10; H, 4.03; N, 4.14.

EXAMPLE 25

(E) and (Z)-N-Methyl-N-phenyl-2-phenyl-3-(1-p-toluenesulfonyl-4,6-dichloroindol-3-yl-2-carboethoxy)propenoic amide Prepare by the method of Example 22 using N-methylaniline.

EXAMPLE 26

(E) and (Z)-N-Benzyl-2-phenyl-3-(1-p-toluenesulfonyl-4,6-dichloroindol-3-yl-2-carboethoxy)propenoic amide Prepare by the method of Example 22 using benzylamine.

EXAMPLE 26.1

(E) and (Z)-N-Benzyl-2-phenyl-3-(1-p-toluenesulfonyl-4,6-dichloroindol-3-yl-2-carboethoxy)propenoic amide Prepare by the method of Example 22.1 using (E) and (Z)-2-phenyl-3-(1-p-toluenesulfonyl-2-carboethoxy-4,6-dichloroindol-3-yl)-propenoic acid (44 3 mg, 0.793 mmol) and benzylamine (95 mL, 0.87 mmol). Purify the residue by chromatograph on silica gel eluting with ether to give a residue. Recrystallize that residue from dichloromethane/ether to give the title compound: mp 150°–153° C.; IR (KBr) vmax 3401, 1730, 1670, 1516, 1371, 1265, 1194, 1182, 1007, 667, 581 cm$^{-1}$; $^1$H NMR ($CDCl_3$) δ7.88 (d, 1H, J=1.7 Hz), 7.83 (s, 1H), 7.60 (m, 1H), 7.58 (m, 1H), 7.3–7.1 (m, 11H), 7.1 (m, 2H), 5.89 (t, 1H, J=5.7 Hz), 4.54 (d, 2H, J=5.7 Hz), 4.21 (q, 2H, J=7.1 Hz), 2.38 (s, 3H), 1.26 (t, 3H, J=7.1 Hz). Elemental Analysis Calculated for $C_{34}H_{28}Cl_2N_2O_5S$: C, 63.06; H, 4.36; N, 4.33. Found: C, 63.07; H, 4.44; N, 4.34.

EXAMPLE 27

(E) and (Z)-N-Morphilino-2-phenyl-3-(1-p-toluenesulfonyl-4,6-dichloroindol-3-yl-2-carboethoxy)propenoic amide Prepare by the method of Example 26.1 using morpholine.

EXAMPLE 27.1

(E) and (Z)-N-Morphilino-2-phenyl-3-(1-p-toluenesulfonyl-4,6-dichloroindol-3-yl-2-carboethoxy)propenoic amide Prepare by the method of Example 22.1 using (E) and (Z)-2-phenyl-3-(1-p-toluenesulfonyl-2-carboethoxy-4,6-dichloro-indol-3-yl)-propenoic acid (450 mg, 0.806 mmol) and morpholine. Purify by chromatograph the residue on silica gel eluting with 1/1 cyclohexane/ethyl acetate to give the title compound: $^1$H NMR ($CDCl_3$) δ7.95 (d, 1H, J=1.7 Hz), 7.71 (d, 2H, J=8.4 Hz), 7.3–7.0 (m, 8H), 6.73 (s, 1H), 4.12 (q, 2H, J=7.2 Hz), 3.71 (bs, 4H), 3.51 (bs, 4H), 2.40 (s, 3H), 1.23 (t, 3H, J=7.2 Hz). Elemental Analysis Calculated for $C_{31}H_{28}Cl_2N_2O_6S$: C, 59.33; H, 4.50; N, 4.46. Found: C, 58.98; H, 4.53; N, 4.27.

EXAMPLE 28

(E) and (Z)-N-4-Methylpiperazino-2-phenyl-3-(1-p-toluenesulfonyl-4,6-dichloroindol-3-yl-2-carboethoxy)propenoic amide Prepare by the method of Example 22 using 4-methylpiperazine.

EXAMPLE 29

(E) and (Z)-N,N-Dimethyl-2-phenyl-3-(4,6-dichloroindol-3-yl-2-carboxylic acid)propenoic amide

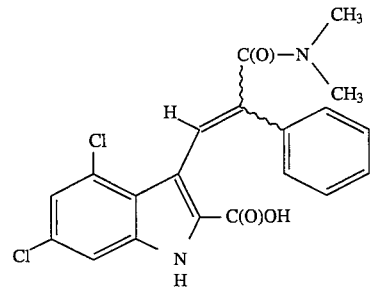

Combine (E) and (Z)-N,N-dimethyl-2-phenyl-3-(1-p-toluenesulfonyl-4,6-dichloroindol-3-yl-2-carboethoxy)propenoic amide (2 mmol), 2M potassium hydroxide solution (2 mL). Heat to reflux for 8 hours. Add water (20 mL) and evaporate in vacuo to remove the methanol. Add 2M hydrochloric acid solution until the pH is 2. Filter, rinse with water. Triturate with diethyl ether, filter, and recrystallize form dichloromethane/ether to give the title compound: partial mp 170°–176° C. (opaque yellow melt; gradual dec follows up to 210° C.); IR (KBr) vmax 3233, 1692, 1613, 1557, 1534, 1497, 1443, 1402, 1209 cm$^1$; $^1$H NMR (DMSO-$d_6$) δ13.27 (bs, 1H), 12.18 (s, 1H), 7.37 (d, 1H, J=1.7 Hz), 7.1 (m, 4H), 7.0 (m, 2H), 6.85 (s, 1H), 3.15 and 2.65 (s, 3H), 2.96 and 2.62 (s, 3H). Elemental Analysis Calculated for $C_{20}H_{16}Cl_2N_2O_3$: C, 59.57; H, 4.00; N, 6.95. Found: C, 58.33; H, 4.06; N, 6.61.

EXAMPLE 30

(E) and (Z)-N-Methyl-2-phenyl-3-(4,6-dichloroindol-3-yl-2-carboxylic acid)propenoic amide

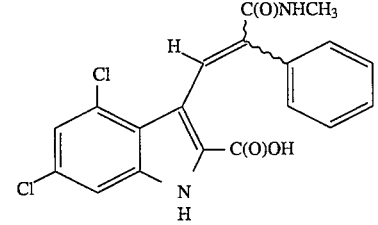

Prepare by the method of Example 29 using (E) and (Z)-N-methyl-2-phenyl-3-(1-p-toluenesulfonyl-4,6-dichloroindol-3-yl-2-carboethoxy)propenoic amide.

EXAMPLE 30.1

(E) and (Z)-N-Methyl-2-phenyl-3-(4-6-dichloroindol-3-yl-2-carboxylic acid)propenoic amide Combine (E) and (Z)-N-methyl-2-phenyl-3-(1-p-toluenesulfonyl-4,6-dichloroindol-3-yl-2-carboethoxy)propenoic amide (0.34 g, 0.59 mmol), lithium hydroxide hydrate (0.042 g, 1.76 mmol), tetrahydrofuran (12 mL), and water (5 mL). Heat to reflux. After 3 days, evaporate in vacuo to remove tetrahydrofuran, dilute to twice the volume with water, and acidify using 1M aqueous hydrochloric acid solution. Extract with ethyl acetate. Dry the organic layer over $MgSO_4$, filter, and evaporate in vacuo to give a residue. Recrystallize the residue from ethyl acetate/cyclohexane to give the title compound: IR (KBr) vmax 3421, 3233, 1665, 1632, 1528, 1298, 1242 $cm^{-1}$; $^1H$ NMR (DMSO-$d_6$) δ13.25 (bs, 1H), 12.06 (s, 1H), 7.66 (s, 1H), 7.35 (m, 1H), 7.31 (m, 1H), 7.10 (m, 4H), 6.93 (m, 2H), 2.70 (d, 3H, J=4.6 Hz). Elemental Analysis Calculated for $C_{19}H_{14}Cl_2N_2O_3$: C, 58.63; H, 3.63; N, 7.20. Found: C, 57.41; H, 3.81; N, 6.82.

EXAMPLE 31

(E) and (Z)-N-Phenyl-2-phenyl-3-(4,6-dichloroindol-3-yl-2-carboxylic acid)propenoic amide

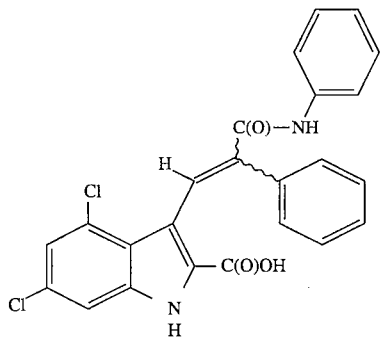

Prepare by the method of Example 29 using (E) and (Z)-N-phenyl-2-phenyl-3-(1-p-toluenesulfonyl-4,6-dichloroindol-3-yl-2-carboethoxy)propenoic amide.

EXAMPLE 31.1

(E) and (Z)-N-Phenyl-2-phenyl-3-(4,6-dichloroindol-3-yl-2-carboxylic acid)propenoic amide Prepare by the method of Example 30.1 using (E) and (Z)-N-phenyl-2-phenyl-3-(1-p-toluenesulfonyl-4,6-dichloronoindol-3-yl-2-carboethoxy)propenoic amide (0.68 g, 1.1 mmol) to give after recrystallization from first dichloromethane/ether and then acetone/ether, the title compound: mp 276° C. (dec); IR (KBr) vmax 3397, 3298, 1690, 1616, 1597, 1524, 1441, 1316, 1235, 1208 $cm^{-1}$; $^1H$ NMR (DMSO-$d_6$) δ13.31 (bs, 1H), 12.18 (s, 1H), 9.67 (s, 1H), 7.81 (s, 1H), 7.8–7.7 (m, 2H), 7.4–7.3 (m, 3H), 7.1 (m, 5H), 7.0 (m, 2H). Elemental Analysis calculated for $C_{24}H_{16}Cl_2N_2O_3$: C, 63,87; H, 3.57; N, 6.21. Found: C, 62.94; H, 3.82; N, 6.02.

EXAMPLE 32

(E) and (Z)-N-Methyl-N-phenyl-2-phenyl-3-(4,6-dichloroindol-3-yl-2-carboxylic acid)propenoic amide

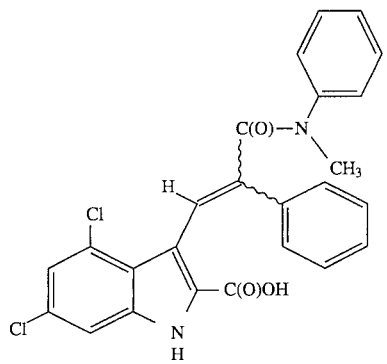

Prepare by the method of Example 29 using (E) and (Z)-N-methyl-N-phenyl-2-phenyl-3-(1-p-toluenesulfonyl-4,6-dichloroindol-3-yl-2-carboethoxy)propenoic amide.

EXAMPLE 33

(E) and (Z)-N-Benzyl-2-phenyl-3-(4,6-dichloroindol-3-yl-2-carboxylic acid)propenoic amide

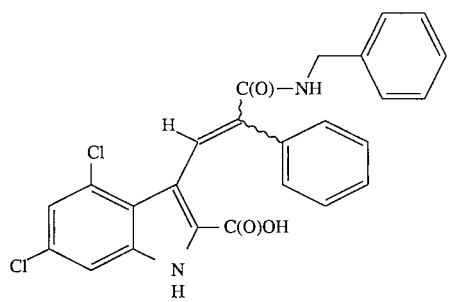

Prepare by the method of Example 29 using (E) and (Z)-N-benzyl-2-phenyl-3-(1-p-toluenesulfonyl-4,6-dichloroindol-3-yl-2-carboethoxy)propenoic amide.

EXAMPLE 33.1

(E) and (Z)-N-Benzyl-2-phenyl-3-(4,6dichloroindol-3-yl-2-carboxylic acid)propenoic amide Prepare by the method of Example 30.1 using (E) and (Z)-N-benzyl-2-phenyl-3-(1-p-toluenesulfonyl-4,6-dichloroindol-3-yl-2-carboethoxy)propenoic amide to give, after recrystallization from first ethyl acetate/cyclohexane and then acetone/acetonitrile, the title compound: mp 262° C. (dec); IR (KBr) vmax 3416, 3322, 1674, 1613, 1557, 1526, 1499, 1454, 1236, 1211 $cm^{-1}$; $^1H$ NMR (DMSO-$d_6$) δ12.07 (bs, 1H), 8.05 (t, 1H, J=6.1 Hz), 7.73 (s, 1H), 7.3–7.2 (m, 6H), 7.1 (m, 4H), 7.0–6.9 (m, 2H), 4.40 (d, 2 H, J=6.1 Hz). Elemental Analysis Calculated for $C_{25}H_{18}Cl_2N_2O_3$: C, 64.53; H, 3.90; N, 6.02. Found: C, 64.30; H, 3.75; N, 6.06.

EXAMPLE 34

(E) and (Z)-N-Morphilino-2-phenyl-3-(4,6-dichloroindol-3-yl-2-carboxylic acid)propenoic amide

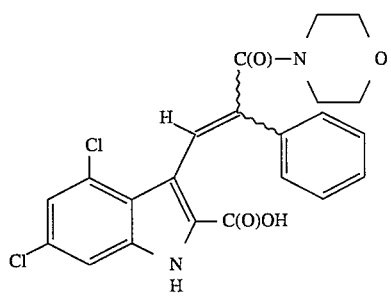

Prepare by the method of Example 29 using (E) and (Z)-N-morphilino-2-phenyl-3-(1-p-toluenesulfonyl-4,6-dichloroindol-3-yl-2-carboethoxy)propenoic amide.

EXAMPLE 34.1

(E) and (Z)-N-Morphilino-2-phenyl-3-(4,6-dichloroindol-3-yl-2-carboxylic acid)propenoic amide Prepare by the method of Example 30.1 using (E) and (Z)-N-morphilino-2-phenyl-3-(1-p-toluenesulfonyl-4,6-dichloroindol-3-yl-2-carboethoxy)propenoic amide to give, after recrystallization form acetone/ethyl acetate, the title compound: mp>275° C; IR (KBr) vmax 1711, 1605, 1466, 1443, 1254, 1233, 1198, 1173 cm$^{-1}$: $^1$H NMR (CDCl$_3$) δ13.40 (bs, 1H), 12.20 (s, 1H), 7.37 (d, 1H, J=1.8 Hz), 7.15–7.09 (m, 4H), 7.05–7.00 (m, 2H), 6.90 (s, 1H), 3.6(m, 4H), 3.33 (bs, 4H). Elemental Analysis Calculated for $C_{22}H_{18}Cl_2N_2O_4$: C, 59.34; H, 4.07; N, 6.29. Found: C, 59.17; H, 3.96; N, 6.16.

EXAMPLE 35

(E) and (Z)-N-4-Methylpiperazino-2-phenyl-3-(4,6,-dichloroindol-3-yl-2-carboxylic acid)propenoic amide

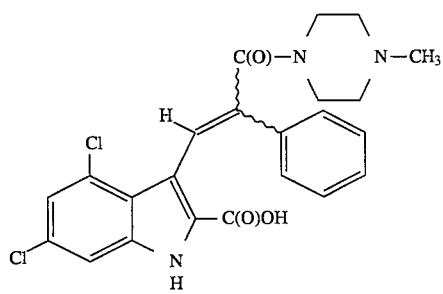

Combine (E) and (Z)-N-4-methylpiperazino-2-phenyl-3-(1-p-toluenesulfonyl-4,6-dichloroindol-3-yl-2-carboethoxy)propenoic amide (2 mmol), 2M potassium hydroxide solution (2 mL). Heat to reflux for 8 hours. Add 2M hydrochloric acid solution until the pH is 2. Evaporate in vacuo to remove the methanol and lyophilize to remove the water to obtain a residue. Triturate the residue repeatedly with ethanol. Evaporate the filtrate in vacuo to obtain a residue. Dissolve the residue in the minimum amount of isopropanol. Add propylene oxide and allow to stand until a solid forms. Filter and rinse with isopropanol to give the title compound.

EXAMPLE 36

(E) and (Z)-2-Phenyl-3-(2-carboethoxy-6-chloroindol-3-yl)-propenoic acid, methyl ester

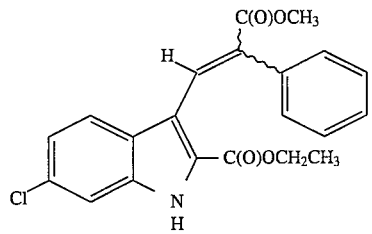

Prepare by the method of Example 7 using 2-phenyl-3-(tri-n-butylstannyl)-propenoic acid, methyl ester. Elem. Anal. calculated for $C_{21}H_{18}NO_4Cl$: C, 65.71; H,4.73; N, 3.65. Found: C, 65.72; H,4.72; N, 3.58.

EXAMPLE 37

(E) and (Z)-2-Phenyl-3-(2-carboethoxy-4,6-dichloroindol-3-yl)-propenoic acid, methyl ester

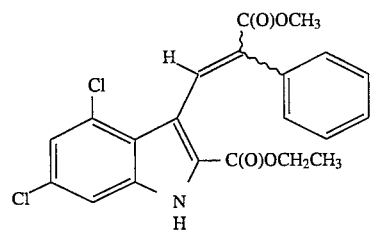

Prepare by the method of Example 1 using 2-phenyl-3-(tri-n-butylstannyl)-propenoic acid, methyl ester.

PREPARATION 4 a) 3-Methoxy-2-phenyl-propenoic acid, methyl ester

Combine hexane washed sodium hydride (24 g, 60% in oil, 580 mmol) and tetrahydrofuran (400mL). Cool to about 5° C. Simultaneously, add dropwise methyl phenylacetate (40 g, 270 mmol) and the methyl formate (35 g, 580 mmol). Add methanol (0.5 mL). Warm to ambient temperature. After 18 hours, pass nitrogen gas over the reaction mixture to remove the solvent to give a residue. Dissolve the residue in dimethylformamide (400 mL) and cool to about 5° C. Slowly add methyl iodide (76 g, 540 mmol). After the addition is complete, warm to ambient temperature. After 3 hours, pour the reaction mixture into water and extract 2 times with diethyl ether. Extract the combined organic layers 5 times with water and once with aqueous saturated sodium chloride solution. Dry the organic layer over MgSO$_4$ and evaporate in vacuo to give the title compound.

b) 3-Methoxy-2-(4-methylphenyl)-propenoic acid, methyl ester can be prepared by the method of Preparation 4 (a) using methyl (4-methylphenyl)acetate.

c) 3-Methoxy-2-(4-bromophenyl)-propenoic acid, methyl ester can be prepared by the method of Preparation 4 (a) using methyl (4-bromophenyl)acetate.

d) 3-Methoxy-2-(4-chlorophenyl)-propenoic acid, methyl ester can be prepared by the method of Preparation 4 (a) using methyl (4-chlorophenyl) acetate: $^1$H NMR (CDCl$_3$) δ7.56 (s, 1H), 7.31–7.24 (m, 4H), 3.74 (s, 3H), 3.65 (s, 3H).

e) 3-Methoxy-2-(4-(trifluoromethyl)phenyl)-propenoic acid, methyl ester can be prepared by the method of Preparation 4 (a) using methyl (4-(trifluoromethyl)phenyl)acetate: $^1$H NMR (CDCl$_3$) δ7.61 (s, 1H), 7.59 (d, 2H, J=8.2 Hz), 7.47 (d, 2H, J=8.2 Hz), 3.87 (s, 3H), 3.75 (s, H); $^{19}$F NMR (CDCl$_3$) δ −63.1.

f) 3-Methoxy-2-(2-chlorophenyl)-propenoic acid, methyl ester can be prepared by the method of Preparation 4 (a) using methyl (2-chlorophenyl)acetate: $^1$H NMR (CDCl$_3$0) δ7.57 (s, 1H), 7.43–7.39 (m, 1H), 7.26–7.21 (m, 3H), 3.83 (s, 3H), 3.70 (s, 3H).

PREPARATION 5 a) 3-Methoxy-2-(3-nitrophenyl)-propenoic acid, methyl ester

Combine (3-nitrophenyl)acetic acid (20.0 g, 110 mmol) and anhydrous methanol (125 mL). Add 7 drops of concentrated sulfuric acid. Heat to 50° C. After 14 hours, cool to ambient temperature. Evaporate in vacuo to give a residue. Partition the residue between water and diethyl ether. Separate the organic layer and extract with aqueous saturated sodium bicarbonate solution and aqueous saturated sodium chloride solution. Dry the organic layer over MgSO$_4$ and filter. Slowly evaporate to give methyl (3-nitrophenyl)acetate. $^1$H NMR (CDCl$_3$) δ8.17 (d, 1H, J=1.1 Hz), 8.14 (dd, 1H, J=1.0, 7.7 Hz), 7.63 (dd, 1H, J=1.1, 7.7 Hz), 7.52 (t, 1H, J=7.7 Hz), 3.75 (s, 2H), 3.73 (s, 3H).

Combine freshly prepared sodium methoxide (9.3 g, 172 mmol) and tetrahydrofuran (125 mL). Cool to 0° C. Add methyl formate (10.6 mL, 172 mmol). Add dropwise a solution of methyl (3-nitrophenyl)acetate (15.3 g, 78.3 mmol) in tetrahydrofuran (125 mL). After the addition is complete, warm the reaction mixture to ambient temperature. After 16 hours, evaporate in vacuo to give a residue. Dissolve the residue in dimethylformamide (125 mL). Add dropwise, methyl iodide (19.5 mL, 313 mmol). After 4 hours, dilute the reaction mixture with ethyl acetate and extract with water, saturated aqueous solution of sodium thiosulfate, and saturated aqueous solution of sodium chloride. Dry over MgSO$_4$, filter through a plug of silica gel eluting with dichloromethane to give the title compound: mp; 101–103° C.

b) 3-Methoxy-2-(4-iodophenyl)-propenoic acid, methyl ester can be prepared by the method of Preparation 5 (a) using (4-iodophenyl)acetic acid.

PREPARATION 5.1 a) 3-Methoxy-2-(4-fluorophenyl)-propenoic acid, methyl ester

Combine 4-fluorophenylacetic acid (10.6 g, 68.8 mmol) and anhydrous methanol (100 mL). Add concentrated sulfuric acid (3 drops). Heat at 50° C. After 12 hours, cool to ambient temperature and evaporate most of the solvent in vacuo. Dilute the evaporated reaction mixture with ether, extract with aqueous saturated sodium bicarbonate solution and brine. Dry over MgSO$_4$ filter and allow to stand until a solid forms. Collect the solid by filtration to give methyl 4-fluorophenylacetate which may be used without further purification.

Suspend sodium hydride (3.4 g, 142 mmol) in anhydrous tetrahydrofuran (100 mL). Cool in an ice/water bath. Add methyl formate (8.8 mL, 142 mmol), methanol (1 drop), and methyl 4-fluorophenylacetate. Warm slowly to ambient temperature. After 18 hours, concentrate in vacuo to give a residue. Dissolve the residue in dimethylformamide and cool in an ice/water bath. Add methyl iodide (8.0 mL, 130 mmol). Warm slowly to ambient temperature. After 3.5 hours, pour the reaction mixture into water and extract twice with ether. Dry the combined organic layers over MgSO$_4$ filter, and concentrate in vacuo to give the title compound: R$_f$=0.52 (silica gel, 2/1 hexane/ethyl acetate).

PREPARATION 6.1

3-Formyl-2-carboethoxy-4-6-dichloroindole

Combine 3,5-dichlorophenylhydrazine (300 g) and ethanol (2 L). Add ethyl pyruvate (153.6 mL) and sulfuric acid (25 mL). After 3 hours, evaporate in vacuo to obtain a residue. Cover the residue with ethyl acetate and water. Add solid sodium bicarbonate until the aqueous layer is neutralized. Separate the layers and extract the aqueous layer with ethyl acetate. Combine the organic layers, dry over MgSO$_4$, filter, and evaporate in vacuo to give ethyl pyruvate-3,5-dichlorophenylhydrazone.

Combine ethyl pyruvate-3,5-dichlorophenylhydrazone (100 g) and polyphosphoric acid (2 kg). Heat on a stream bath. After 5 hours, stop the heating and slowly add ice (100 g) to thin the solution. Pour the reaction mixture onto ice to give an aqueous suspension. Extract the aqueous suspension three times with ethyl acetate. Combine the organic layers, dry over MgSO$_4$, filter, and evaporate in vacuo to give a solid. Triturate the solid with diethyl ether, filter, and dry to give 2-carboethoxy-4,6-dichloroindole.

Combine 2-carboethoxy-4,6-dichloroindole (20.0 g, 0,077 mol), and dimethylformamide (9.0 mL, 0,117 mol) in dichloroethane (100 mL). Add phosphoryl chloride (18.0 g, 0.117 mmol). Heat to reflux. After 3.5 hours, cool the reaction mixture to ambient temperature to obtain a solid. Collect the solid by filtration, rinse with water. Combine the solid with aqueous 1M sodium acetate solution and stir. After 1 hour, filter, rinse with water, and dry to give the title compound.

PREPARATION 6.2

3-Formyl-2-carboethoxy-4,6-dichloroindole (10.0 g, 0.039

Combine 2-carboethoxy-4,6-dichloroindole (10.0 g, 0.039 mol), and dimethylformamide (4.5 mL, 0,057 mol) in dichloroethane (20 mL). Add phosphoryl chloride (8.9 g, 0,058 mmol). Heat to 80° C. After 18 hours, cool the reaction mixture to ambient temperature and combine with aqueous 1M sodium acetate solution and stir. After 18 hours, filter, rinse with water, and dry to give the title compound: mp 216–217° C; R$_f$=0.24 (silica gel, 1/1 ether/hexane); $^1$H NMR (CDCl$_3$) δ10.80 (s, 1H), 9.40 (br s, 1H), 7.39 (s, 1H), 7.35 (s, 1H), 4.52 (q, 2H, J=7.2 Hz), 1.47 (t, 3H, J=7.1 Hz).

EXAMPLE 37.1

(E) and (Z)-2-phenyl-3-(2-carboethoxy-4,6-dichloroindol-3-yl)-propenoic acid, methyl ester Combine 3-methoxy-2-phenyl-propenoic acid, methyl ester (15 g, 78 mmol) and 1,2-dichloroethane (200 mL). Add trimethylsilyl triflate (78 mmol) by syringe. After 15 minutes, add 2-carboethoxy-4,6-dichloroindole (60 mmol). Heat to 70° C. After 6.5 hours, cool the reaction mixture to ambient temperature and pour onto a 1/1 mixture of water/saturated aqueous solution of sodium bicarbonate. Extract 2 times with ethyl acetate. Combine the organic layers and extract with saturated aqueous solution of sodium chloride. Dry the organic layer over MgSO$_4$, filter, and evaporate in vacuo to give a residue. Chromatograph the residue on silica gel eluting sequentially with 15% ethyl acetate/hexane and then 50% ethyl acetate/hexane to give the title compound.

EXAMPLE 38

(E) and (Z)-2,(3-Nitrophenyl)-3-(2-carboethoxy-4,6-dichloroindo-3-yl)-propenoic acid, methyl ester

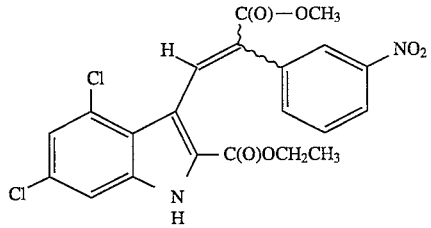

Combine 3-methoxy-2-(3-nitrophenyl)-propenoic acid, methyl ester (13.9 g, 58.8 mmol) and 1,2-dichloroethane (100 mL). Add dropwise trimethylsilyl triflate (11.4 mL, 58.5 mmol) by syringe. After 15 minutes, add portionwise 2-carboethoxy-4,6-dichloroindole (11.7 g, 45.2 mmol). Heat to 70° C. After 16 hours, cool to ambient temperature. Add aqueous saturated sodium bicarbonate solution. Extract with ethyl acetate. Separate the organic layer and extract with water and aqueous saturated sodium chloride solution. Dry the organic layer over $MgSO_4$ filter, and evaporate in vacuo to give a residue. Chromatograph the residue on silica gel eluting with 1/3 ethyl acetate/hexane to give the title compound: $R_f$=0.5 (30% ethyl acetate/cyclohexane).

Separate the isomers by fractional recrystallization from ethyl acetate/cyclohexane. Initially, mainly the Z isomer precipitates as a yellow powder, which can then be recrystallized from ether/cyclohexane to obtain Z isomer: mp 178°–180° C; IR (KBr) vmax 3408, 3316, 1715, 1530, 1443, 1350, 1319, 1238, 1209, 1182 cm$^{-1}$; $^1$H NMR (DMSO-d$_6$) δ12.46 (bs, 1H), 8.27 (t, 1H, J=1.9 Hz), 8.22 (dm, 1H, J=8.2 Hz), 7.92 (dm, 1H, J=8.0 Hz), 7.71 (t, 1H, J=8.0 Hz), 7.60 (s, 1H), 7.44 (d, 1H, J=1.7 Hz), 7.17 (d, 1H, J=1.7 Hz), 4.26 (q, 2H, J=7.1 Hz), 3.41 (s, 3H), 1.23 (t, 3H, J=7.1 Hz). Elemental Analysis Calculated for $C_{21}H_{16}C_{12}N_2O_6$: C, 54.44; 3.48; N, 6.05. Found: C, 54.41; H, 3.54; N, 6.03.

The E isomer then precipitates to give the E isomer: mp 173°–175° C; IR (KBr) vmax 3399, 3304, 1715, 1556, 1532, 1437, 1350, 1321, 1300, 1242 cm$^{-1}$; $^1$H NMR (DMSO-d$_6$) δ12.35 (bs, 1H), 8.25 (s, 1H), 7.96 (dm, 1H, J=7.6 Hz), 7.86 (m, 1H), 7.39 (t, 1H, J=7.6 Hz ), 7.36 (dm, 1H, J=7.6 Hz), 7.33 (d, 1H, J=1.7 Hz), 7.14 (d, 1H, J=1.7 Hz), 4.18 (q, 2H, J=7.1 Hz), 3.81 (s, 3H), 1.23 (t, 3H, J=7.1 Hz). Elemental Analysis Calculated for $C_{21}H_{16}C_{12}N_2O_6$: C, 54.44; H, 3.48; N, 6.05. Found: C, 5 4.55; H, 3.41; N, 5.93.

EXAMPLE 39

(E) and (Z)-2-(3-Aminophenyl)-3-(2-carboethoxy-4,6-dichloroindol-3yl)-propenoic acid, methyl ester

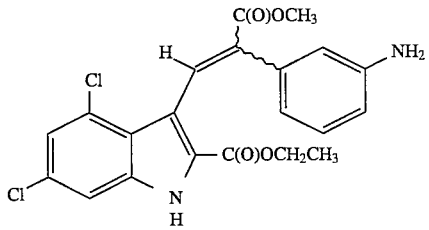

Combine (E) and (Z)-2-(3-nitrophenyl)-3-(2-carboethoxy-4,6-dichloroindol-3-yl)-propenoic acid, methyl ester (16.2 g, 35 mmol) and ethyl acetate (175 mL). Add portionwise tin (II) chloride dihydrate (47.2 g, 209 mmol). Heat to reflux. After 4 hours, cool the reaction mixture to ambient temperature. Slowly add, aqueous saturated sodium bicarbonate solution. Add water and ethyl acetate. Separate the aqueous layer and extract three times with ethyl acetate. Combine the organic layers and extract with aqueous saturated sodium solution. Dry over $MgSO_4$ filter, and evaporate in vacuo to give a residue. Chromatograph the residue on silica gel eluting with 1/2 ethyl acetate/hexane to give the title compound: mp 249°–251° C.; $^1$H NMR (DMSO-d$_6$) δ12.36 (s, 1H), 7.45 (d, 1H, J=1.7 Hz), 7.32 (s, 1H), 7.22 (d, 1H, J=1.7 Hz), 7.05 (t, 1H, J=7.8 Hz), 6.67 (d, 1H, J=1.9 Hz), 6.55–6.62 (m, 2H), 5.16 (s, 1H), 4.27 (q, 2H, J=7.1 Hz), 3.39 (s, 3H), 1.25 (t, 3H, J=7.1). Elemental Analysis Calculated for $C_{21}H_{18}Cl_2N_2O_4/2$ $H_2O$: C, 57.09; H, 4.22; N, 6.34. Found: C, 56.94; H, 4.04; N, 6.15.

EXAMPLE 40

(E) and (Z)-2-(3-Aminophenyl)-3-(4,6-dichloroindol-3-yl-2-carboxylic acid)-propenoic acid

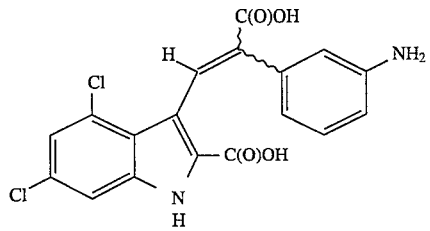

Prepare by the method of Example 3 using (E) and (Z)-2-(3-aminophenyl)-3-(2-carboethoxy-4,6-dichloroindol-3-yl)-propenoic acid, methyl ester (550 mg, 1.27 mmol) recrystallize from ethyl acetate/hexane to give the title compound. $^1$H NMR (DMSO-d$_6$) δ12.1 (s, 1H), 7.93 (s, 1H), 7.31 (d, 1H, J=1.6 Hz), 7.12 (d, 1H, J=1.1 Hz), 6.67 (t, 1H, J=7.6 Hz), 6.27 (1, 1H), 6.24 (d, 1H, J=1.1 Hz), 6.10 (d, 1H, J=7.6 Hz). Elemental Analysis Calculated for $C_{18}H_{12}Cl_2N_2O_4/H_2O$: C, 52.83; H, 3.45; N, 6.85. Found: C, 52.22; H, 3.59; N, 6.05.

EXAMPLE 40.1

(E) and (Z)-2-(3-Aminophenyl)-3-(4,6-dichloroindol-3-yl-2-carboxylic acid)-propenoic acid Combine (E) and (Z)-2-(3-aminophenyl)-3-(2-carboethoxy-4,6-dichloroindol-3-yl)-propenoic acid, methyl ester (550 mg, 1.27 mmol) in tetrahydrofuran (7 mL) and water (5 mL). Add lithium hydroxide hydrate (304 mg, 12.7 mmol). Heat to 70° C. After 24 hours, cool, evaporate the tetrahydrofuran in vacuo, and extract the aqueous phase with ethyl acetate. Filter the aqueous phase through celite, acidify with aqueous 0.5M sodium bisulfate solution to pH 4 and extract three times with ethyl acetate. Combine organic layers and extract with brine. Dry over $MgSO_4$ filter and evaporate in vacuo to give a residue. Recrystallize the residue from methanol to give the title compound: mp 211°–220° C.; IR (KBr) vmax 3430, 3246, 1694, 1611, 1240 cm$^{-1}$; $^1$H (DMSO-$_6$) δ12.1 (s, 1H), 7.93 (s, 1H), 7.31 (d, 1H, J=1.6 Hz), 7.12 (d, 1H, J=1.1 Hz), 6.67 (t, 1H, J=7.6 Hz), 6.2 7 (s, 1H), 6.24 (d, 1H, J=1.1 Hz), 6.10 (d, 1H, J=7.6 Hz). Elemental Analysis Calculated for $C_{18}H_{12}C_{12}N_2O_4$. 0.58

H₂O: C, 53.83; H, 3.30; N, 6.97. Found: C, 53.69; H, 3.37; N, 6.74.

EXAMPLE 41

(E) and (Z)-2-(4-Bromophenyl)-3-(2-carboethoxy-4,6-dichloroindol-3-yl)-propenoic acid, methyl ester

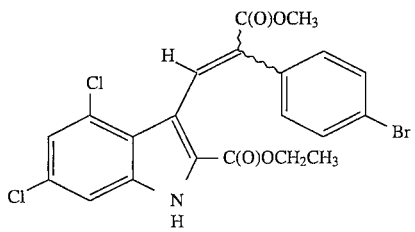

Prepare by the method of Example 37.1 using 2-carboethoxy-4,6-dichloroindole (4.44 g, 17.2 mmol), 3-methoxy-2-(4-bromophenyl)-propenoic acid, methyl ester (5.13 g, 18.92 mmol), and trimethylsilyl triflate (3.44 mL, 17.2 mmol) recrystallize from ethyl acetate to give the title compound.

EXAMPLE 42

(E) and (Z)-2-(4-Bromophenyl),3-(4,6-dichloroindol-3-yl-2-carboxylic acid)-propenoic acid

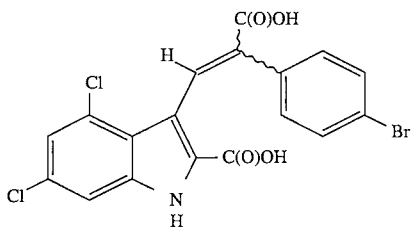

Combine (E) and (Z)-2-(4-bromophenyl)-3-(2-carboethoxy-4,6-dichloroindol-3-yl)-propenoic acid, methyl ester (5.52 g, 11.1 mmol), tetrahydrofuran (67 mL), methanol (33 mL), and aqueous 1M sodium hydroxide solution (66.6 mL). Heat to reflux. After 18 hours, cool the reaction mixture to 0° C. and acidify with 1M hydrochloric acid solution to give a solid. Filter the solid. Recrystallize from acetone/ethanol, filter, and dry to give the title compound. Elemental Analysis Calculated for $C_{18}H_{10}BrCl_2N_2O_4$/0.9 H₂O: C, 45.91; H, 2.52; N, 2.97. Found: C, 45.91; H, 2.30; N, 2.90.

EXAMPLE 43

(E) and (Z)-2-(4-Nitrophenyl)-3-(2-carboethoxy-4,6-dichloroindol-3-yl)-propenonitrile

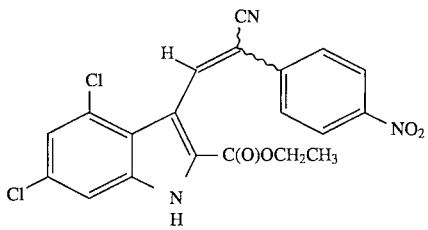

Combine 3-formyl-2-carboethoxy-4,6-dichloroindole (5.0 g, 17.48 mmol), 4-nitrophenylacetonitrile (2.83 g, 17.48 mmol), piperidine (0.2 mL), and ethanol (50 mL). Heat to reflux. After 16 hours, cool to ambient temperature. Cool to 0° C. to give a solid. Filter and dry to give the title compound: IR (KBr) νmax 3402, 3283, 2224, 1709, 1684, 1609, 1522, 1344, 1238 cm⁻¹; ¹H NMR (DMSO-₆) δ12.92 (s, 1H), 8.65 (s, 1H), 8.36 (d, 1H, J=8.9 Hz), 8.03 (d, 1H, J=8.9 Hz), 7.53 (d, 1H, J=1.6 Hz), 7.37 (d, 1H, J=1.6 Hz), 4.34 (q, 2H, J=7.1 Hz), 1.24 (t, 3H, J=7.1). Elemental Analysis Calculated for $C_{20}H_{13}Cl_2N_3O_4$: C, 55.83; H, 3.05; N, 9.77. Found: C, 55.65; H, 2.70; N, 9.67.

EXAMPLE 44

(E) and (Z)-2-(4-Aminophenyl)-3-(2-carboethoxy-4,6-dichloroindol-3-yl)-propenonitrile

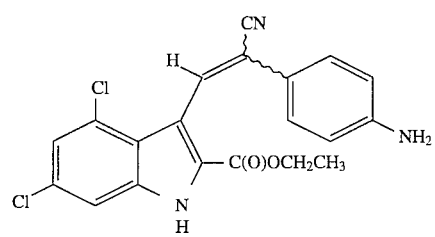

Combine (E) and (Z)-2-(4-nitrophenyl)-3-(2-carboethoxy-4,6-dichloroindol-3-yl)-propenonitrile (5.0 g, 11.6 mmol) and ethanol (75 mL). Add portionwise tin (II) chloride dihydrate (13.1 g, 58 mmol). Heat to 70° C. After 4 hours, cool the reaction mixture to ambient temperature. Evaporate in vacuo. Add water and slowly add, aqueous saturated sodium bicarbonate solution until the pH is about 7.5. Extract 2 times with ethyl acetate. Combine the organic layers and extract with aqueous saturated sodium chloride solution. Dry over MgSO₄, filter, and evaporate in vacuo to give the title compound.

EXAMPLE 44.1

(E) and (Z)-2-(4-Aminophenyl)-3-(2-carboethoxy-4,6-dichloroindol-3-yl)-propenonitrile Combine (E) and (Z)-2-(4-nitrophenyl)-3-(2-carboethoxy-4,6-dichloroindol-3-yl)-propenonitrile (6.93 g, 16.1 mmol) and ethanol (50 mL). Add portionwise tin (II) chloride dihydrate (18.2 g, 80.5 mmol). Heat to 70° C. After 4 hours, cool the reaction mixture to ambient temperature. Evaporate in vacuo. Add water and slowly add, aqueous saturated sodium bicarbonate solution until the pH is about 7.5. Extract 2 times with ethyl acetate. Combine the organic layers and extract with aqueous saturated sodium chloride solution. Dry over MgSO₄ filter, and evaporate vacuo to give a residue. Chromatograph the residue on silica gel eluting with 2/1 hexane/ethyl acetate to give the title compound: IR (KBr) νmax 3385, 3302, 2222, 1690, 1622, 1609, 1514, 1238 cm⁻¹; ¹H NMR (DMSO-₆) δ10.15 (s, 1H), 7.85 (s, 1H), 7.52 (d, 1H, J=7.4 Hz), 7.31 (s, 1H), 7.14 (d, 1H, J=1.3 Hz), 6.74 (d, 1H, J=7.4 Hz), 4.36 (q, 2H, J=7.1 Hz), 1.27 (t, 3H, J=7.1). Elemental analysis Calculated for $C_{20}H_{15}Cl_2N_3O_2$: C, 60.02; H, 3.78; N, 10.50. Found: C, 59.65; H, 3.48; N, 10.07.

EXAMPLE 45

(E) and (Z)-2-(4-Aminophenyl)-3-(2-carboethoxy-4,6-dichloroindol-3-yl)-propenoic acid amide

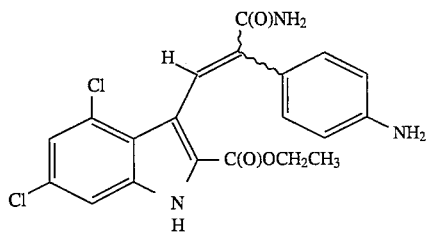

Combine (E) and (Z)-2-(4-aminophenyl)-3-(2-carboethoxy-4,6-dichloroindol-3-yl)-propenonitrile (1.0 g, 2.5 mmol), sulfuric acid (15 mL), acetic acid (15 mL), and water (0.3 mL). Heat to about 70° C. After 8 hours, cool to ambient temperature and pour the reaction mixture into ice-water. Adjust te pH to about 4 and extract with ethyl acetate. Dry over MgSO$_4$, filter, and evaporate in vacuo to give a residue. Chromatograph the residue on silica gel eluting with 1/1 ethyl acetate/hexane containing 5% acetic acid to give the title compound.

EXAMPLE 45.1

(E) and (Z)-2-(4-Aminophenyl)-3-(2-carboethoxy-4,6-dichloroindol-3-yl)-propenoic acid amide Combine (E) and (Z)-2-(4-aminophenyl)-3-(2-carboethoxy-4,6-dichloroindol-3-yl)-propenonitrile (6.20 g, 15.5 mmol), sulfuric acid (20 mL) and acetic acid (20 mL). Heat to about 70° C. After 3 hours, cool in a ice/water bath to give a solid. Collect by filtration give the title compound: $^1$H NMR (DMSO-$_6$) δ12.24–12.20 (s, 1H), 7.64 (s, 1H), 7.40 (m, 2H), 7.2 (s, 2H), 6.84 (d, 2H), 6.80 (d, 2H), 4.20 (q, 2H), 4.4–3.4 (bs, 2H), 1.25 (t, 3H).

EXAMPLE 46

(E) and (Z)-2-(4-Aminophenyl)-3-(4,6-dichloroindol-3-yl-2-carboxylic acid)-propenoic acid

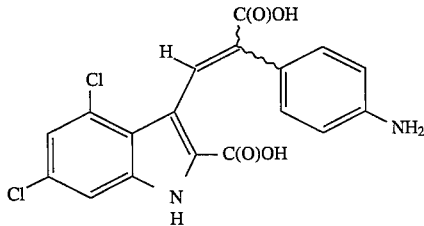

Combine (E) and (Z)-2-(4-Aminophenyl)-3-(2-carboethoxy-4,6-dichloroindol-3-yl)-propenoic acid amide (1.90 g, 5.38 mmol) and aqueous 6M sodium hydroxide solution (20 mL). Heat to 105° C. After 14 hours, cool to 0° C. and acidify to pH 3 with aqueous 6M hydrochloric acid solution to form a solid. Collect the solid by filtration to give the title compound: IR (KBr) vmax 3395, 3271, 1724, 1612, 1176, 1082 cm$^{-1}$: $^1$H NMR (DMSO-$_6$) δ12.12 (s, 1H), 7.87 (s, 1H), 7.33 (d, 1H, J=1.8 Hz), 7.10 (d, 1H, J=1.8 Hz), 6.62 (d, 2H, J=8.6 Hz), 6.23 (d, 2H, J=8.6 Hz).

EXAMPLE 47

(E) and (Z)-2-(4-Iodophenyl)-3-(2-carboethoxy-4,6-dichloroindol-3-yl)-propenoic acid, methyl ester

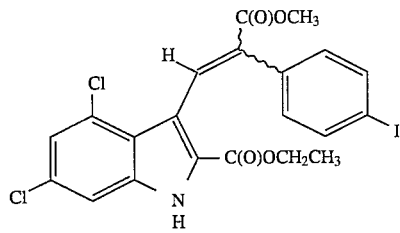

Prepare by the method of Example 37.1 using 2-carboethoxy-4,6-dichloroindole (2.83 g, 11.0 mmol), 3-methoxy-2-(4-iodophenyl)-propenoic acid, methyl ester (5.13 g, 18.92 mmol), and trimethylsilyl triflate (2.30 mL, 12.1 mmol). Recrystallize from ethyl acetate/cyclohexane to give the title compound: mp 213–215° C. (dec); IR (KBr) vmax 3416, 3306, 1748, 1717, 1614, 1485, 1321, 1294, 1240 cm$^{-1}$; $^1$H NMR (DMSO-$_6$) δ12.45 (bs, 1H), 8.14 (s, 1H), 7.70 and 7.50 (2d, 2H, J=8.5 Hz), 7.45 and 7.39 (2d, 1H, J=1.7 Hz), 7.22 and 7.21 (2d, 1H, J=1.7 Hz), 6.94 and 6.75 (2d, 2H, J=8.4 Hz), 4.19 (q, 2H, J=7.0 Hz), 3.78 and 3.64 (2s, 3H), 1.25 (t, 3H, J=7.0 Hz). Elemental Analysis Calculated for $C_{21}H_{16}Cl_2INO_4$: C, 46.35; H, 2.96; N, 2.57. Found: C, 45.96; H, 2.90; N, 2.65.

EXAMPLE 48

(E) and (Z)-2-(4-Iodophenyl)-3-(4,6-dichloroindol-3-yl-2-carboxylic acid)-propenoic acid

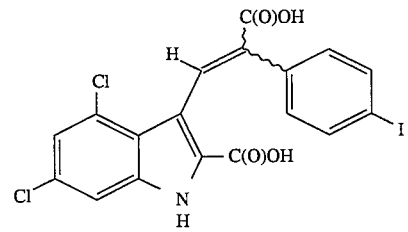

Prepare by the method of example 30.1 using (E) and (Z)-2-(4-iodophenyl)-3-(2-carboethoxy-4,6-dichloroindol-3-yl)-propenoic acid, methyl ester (0.95 g, 1.8 mmol) to obtain, after recrystallization from ethyl acetate the title compound: IR (KBr) vmax 3427, 3312, 3271, 1692, 1613, 1240, 1221 cm$^{-1}$; $^1$H NMR (DMSO-$_6$) δ13.09 (bs, 2H), 12.21 (s, 1H), 8.11 (s, 1H), 7.50–7.45 (m, 2H), 7.35 (d, 1H, J=1.8 Hz ), 7.17 (d, 1H, J=1.8 Hz), 6.80–6.75 (m, 2H).

Elemental Analysis Calculated for $C_{18}H10Cl_2INO_4$: C, 43.06; H, 2.01; N, 2.79. Found: C, 42.74; H, 2.02; N, 2.51.

EXAMPLE 49

(E) and (Z)-2-(4-Chlorophenyl)-3-(2-carboethoxy-4,6-dichloroindol-3-yl)-propenoic acid, methyl ester

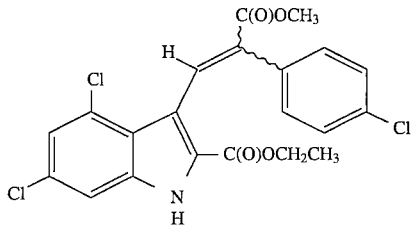

Prepare by the method of Example 37.1 using 2-carboethoxy-4,6-dichloroindole (2.83 g, 11.0 mmol), 3-methoxy-2-(4-chlorophenyl)-propenoic acid, methyl ester (5.13 g, 18.92 mmol), and trimethylsilyl triflate (2.30 mL, 12.1 mmol) to give the title compound: mp 185°–187° C; IR (KBr) vmax 3418, 3308, 3099, 3088, 3038, 2984, 2953, 2906, 1701, 1612, 1558, 1531, 1491, 1437, 1394, 1369, 1321, 1303, 1294, 1242, 1176, 1091, 1080, 1037, 1014, 981, 941, 923, 837, 796, 983, 765, 744, 721, 644, 592, 553, 534 cm$^{-1}$; $^1$H NMR (CDCl$_3$) δ9.23 (bs, 1H), 8.23 (s, 1H), 7.23 (s, 1 H), 7.12 (s, 1H), 7.10–6.99 (m, 4H), 4.31 (q, 2H, J=7.2 Hz), 3.87 (s, 3H), 1.34 (t, 3H, J=7.1 Hz). Elemental Analysis Calculated for $C_{21}H_{16}Cl_3NO_4$: C, 55.71; H, 3.56; N, 3.09. Found: C, 55.76; H, 3.43; N, 2.97.

EXAMPLE 50

(E) and (Z)-2-(4-Chlorophenyl)-3-(4,6-dichloroindol-3-yl-2-carboxylic acid)-propenoic acid

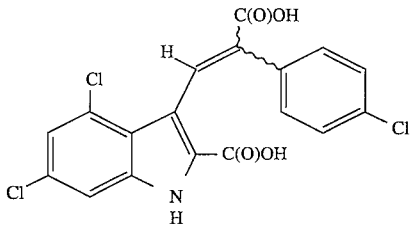

Prepare by the method of example 30.1 using (E) and (Z)-2-(4-Chlorophenyl)-3-(2-carboethoxy-4,6-dichloroindol-3-yl)-propenoic acid, methyl ester (0.95 g, 1.8 mmol) to obtain, after recrystallization from acetone/water the title compound: mp 252–254° C. (dec); IR (KBr) vmax 3429, 3271, 3161, 3099, 3090, 3049, 2694, 2661, 2660, 2615, 2542, 1695, 1635, 1614, 1558, 1535, 1493, 1456, 1435, 1410, 1394, 1369, 1338, 1294, 1234, 1219, 1178, 1091, 1080, 1004, 981, 933, 835, 790, 769, 725, 678, 642, 530, 590, 549, 534 cm$^{-1}$; $^1$H NMR (DMSO-$_6$) δ13.1 (bs, 1.5H), 12.2 (s, 1H), 8.11 (s, 1H), 7.34 (s, 1H), 7.17 (m, 3H), 6.97 (m, 2H). Elemental Analysis Calculated for $C_{18}H_{10}Cl_3NO_4$. 1.0 $C_3H_6O$: C, 53.76; H, 3.40; N, 3.01. Found: C, 53.27; H, 3.19; N, 2.92.

EXAMPLE 51

(E) and (Z)-2-(4-Methylphenyl)-3-(2-carboethoxy-4,6-dichloroindol-3-yl)-propenoic acid, methyl ester

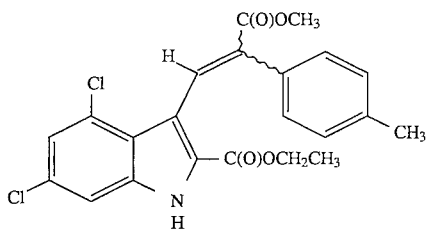

Prepare by the method of Example 37.1 using 2-carboethoxy-4,6-dichloroindole (2.83 g, 11.0 mmol), 3-methoxy-2-(4-methylphenyl)-propenoic acid, methyl ester (5.13 g, 18.92 mmol), and trimethylsilyl triflate (2.30 mL, 12.1 mmol) to give, after chromatography on silica gel eluting with 4/1 hexane/ethyl acetate, the title compound: $^1$H NMR (CDCl$_3$) δ12.32 and 12.28 (2 s, 1H), 8.08 (s, 1H), 7.38 (s, 1H), 7.2 (s, 1H), 6.8–7.0 (dd, 4H), 4.2 (q, 2H), 3.78 (s, 3H), 3.76 (s, 3H), 2.16 (s, 3H), 1.24 (t, 3H).

EXAMPLE 52

(E) and (Z)-2-(4-Methylphenyl)-3-4,6-dichloroindol-3-yl-2-carboxylic acid)-propenoic acid

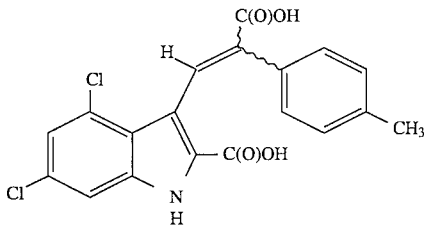

Combine (E) and (Z)-2-(4-methylphenyl)-3-(2-carboethoxy-4,6-dichloroindol-3-yl)-propenoic acid, methyl ester (2.73 g , 6.32 mmol) in tetrahydrofuran (40 mL) and methanol (20 mL). Add aqueous 1.0M sodium hydroxide solution (38 mL, 38 mmol). Heat to 70° C. After 24 hours, cool the reaction mixture and concentrate in vacuo, acidify with 1M hydrochloric acid solution, and extract with dichloromethane. Separate the organic layer, dry over MgSO$_4$, and evaporate in vacuo to give a residue. Recrystallization the residue from ethyl acetate/cyclohexane to give the title compound: $^1$H NMR (DMSO-$_6$) δ12.76 (bs, 2H), 12.12 (s, 1H), 8.02 (s, 1H), 7.32 (d, 1H, J=1.8 Hz), 7.14 (d, 1H, J=1.8 Hz), 6.89 (d, 2H J=8.5 Hz), 6.85 (d, 2H, J=8.5 Hz), 2.15 (s, 3H). Elemental Analysis Calculated for $C_{19}H_{13}Cl_2NO_4$.

H₂O: C, 58.48; H, 3.56; N, 3.59. Found: C, 57.20; H, 3.30; N, 3.30.

EXAMPLE 53

(E) and (Z)-2-(4-Trifluoromethylphenyl)-3-(2-carboethoxy-4,6-dichloroindol-3-yl)-propenoic acid, methyl ester

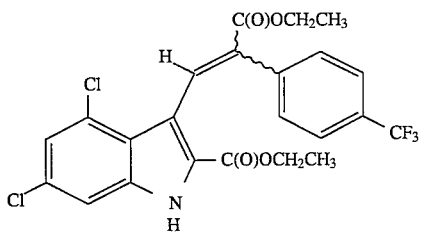

Prepare by the method of Example 37.1 using 2-carboethoxy-4,6-dichloroindole (5.07 g, 19.6 mmol), 3-methoxy-2-(4-(trifluoromethyl)phenyl)-propenoic acid, methyl ester (5.62 g, 21.6 mmol), and trimethylsilyl triflate (3.9 mL, 20 mmol) to give, after recrystallization from ether/cyclohexane, the title compound: IR (KBr) vmax 3304, 1717, 1705, 1682, 1325, 1298, 1244, 1169, 1126, 1111, 1069 cm⁻¹; MS m/z 514 (M++29), 486 (M++1), 466,454 (100).

EXAMPLE 54

(E) and (Z)-2-(4-Trifluoromethylphenyl1)-3-(4,6-dichloroindol-3-yl-2-carboxylic acid)-propenoic acid

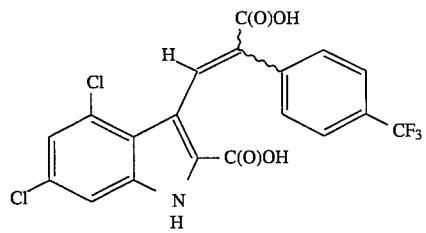

Prepare by the method of Example 3 using (E) and (Z)-2-(4-trifluoromethylphenyl)-3-(2-carboethoxy-4,6-dichlorindol-3-yl)-propenoic acid, methyl ester (5.0 g, 10 mmol) to give, after after recrystallization from first ethyl acetate and then acetone/cyclohexane, the title compound: IR (KBr) vmax 3096, 1692, 1615, 1327, 1244, 1219, 1171, 1130, 1111, 1069 cm⁻¹; ¹H NMR (DMSO-₆) δ13.13 (bs, 1H), 12.22 (s, 1H), 8.20 (s, 1H), 7.5 (m, 2H), 7.35 (d, 1H, J=3 Hz), 7.2 (m, 3H). Elemental Analysis Calculated for C₁₉H₁₀F₃Cl₂NO₄: C, 51.38; H, 2.27; N, 3.15. Found: C, 51.31; H, 2.85; N, 2.92.

EXAMPLE 55

(E) and (Z)-2-(2-Chlorophenyl)-3-(2-carboethoxy-4,6-dichloroindol-3-yl)-propenoic acid, methyl ester

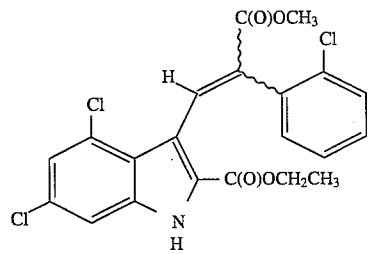

Prepare by the method of Example 37.1 using 2-carboethoxy-4,6-dichloroindole, 3-methoxy-2-(2-chlorophenyl)-propenoic acid, methyl ester (2.8 g, 12 mmol, and trimethylsilyl triflate to give, after recrystallization from ether/cyclohexane, the title compound: mp 201–206° C.; IR (KBr) vmax 3420, 3410, 3304, 3084, 3024, 2987, 2951, 2904, 1724, 1705, 1678, 1641, 1612, 1558, 1533, 1473, 1435, 1390, 1369, 1323, 1292, 1242, 1197, 1178, 1128, 1114, 1078, 1064, 1026, 981, 954, 939, 862, 841, 815, 761, 742, 694, 675, 642, 628, 592, 549. 534 cm⁻¹; ¹H NMR (CDCl₃) δ8.99 (bs, 1H), 8.32 (s, 1H), 7.32–6.96 (m, H), 4.35 (q, 2H, J=7.4 Hz), 3.88 (s, 3H), 1.37 (t, 3H, J=7.1 Hz). Elemental Analysis Calculated for C₂₁H₁₆Cl₃NO₄: C, 55.71; H, 3.56; N, 3.09. Found: C, 54.39; H, 3.68; N, 3.08.

EXAMPLE 56

(E) and (Z)-2-(2-Chlorophenyl)-3-(4,6-dichloroindol-3-yl-2-carboxylic acid)-propenoic acid

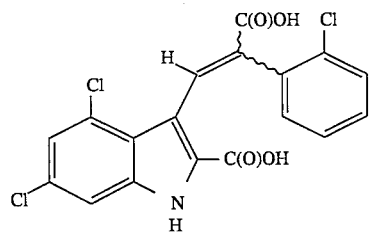

Prepare by the method of Example 3 using (E) and (Z)-2-(2-chlorophenyl)-3-(2-carboethoxy-4,6-dichloroindol-3-yl)-propenoic acid, methyl ester ((1.3 g, 2.9 mmol) to give, after recrystallization form acetone/water, the title compound: mp 244°–246° C. (dec); IR (KBr) vmax 3423, 3259, 3161, 3090, 2692, 2681, 2671, 2656, 2613, 2604, 2542, 1695, 1633, 1614, 1558, 1533, 1473, 1438, 1411, 1392, 1369, 1338, 1292, 1236, 1219. 1130, 1114, 1080, 1062, 1037, 981, 839, 1792, 779. 758, 740, 715, 673, 642, 590 cm⁻¹; ¹H NMR (DMSO-d₆) δ12.7 (bs, 1.2H), 12.17 (s, 1H), 8.16 (s, 1H), 7.33–6.99 (overlapping m, 6H). Elemental Analysis Calculated for C₁₈H₁₀Cl₃NO₄. 0.5 C₃H₆O: C, 53.26; H, 2.98; N, 3.18. Found: C, 53.53; H, 3.27; N, 2.91.

EXAMPLE 57

(E) and (Z)-2-(3-Nitrophenyl),3-(4,6-dichloroindoindol-3-yl-2-carboxylic acid)-propenoic acid

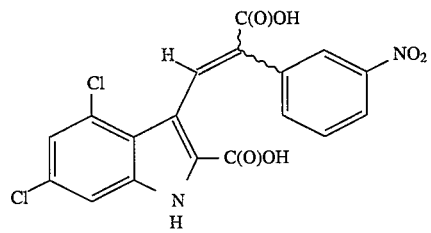

Prepare by the method of Example 3 using (E) and (Z)-2-(3-nitrophenyl)-3-(2-carboethoxy-4,6-dichloroindol-3-yl)-propenoic acid, methyl ester (550 mg, 1 27 mmol) to give, after recrystallization from ethyl acetate, the title compound:: mp 272°–275° C; IR (KBr) vmax 3414, 3298, 1691, 1612, 1530, 1350, 1242 cm⁻¹; ¹H NMR (DMSO-d₆) δ13.20 (bs, 1H), 12.28 (s, 1H), 8.27 (s, 1 H), 7.95–8.00 (m, 1H), 7.85–7.90 (m, 1H), 7.30–7.45 (m, 3H), 7.19 (s, 1H). Elemental Analysis Calculated for C₁₈H₁₀Cl₂N₂O₆. H₂O: C, 49.22; H, 2.75; N, 6.38. Found: C, 49.28; H, 2.36; N, 6.22.

EXAMPLE 58

(E) and (Z)-2-(Phenyl)-3-(1-p-toluenesulfonyl-2-carboethoxy-4,6-dichloroindol-3-yl)-propenoic acid amide Prepare by the method of Example 22.1 using (E) and (Z)-2-(phenyl)-3-(2-carboethoxy-4,6-dichloroindol-3-yl)-propenoic (0.77 g, 1.4 mmol) and ammonium chloride to give, after two recrystallizations from dichloromethane/ether the title compound: mp 205°–208° C; IR (KBr) νmax 1728, 1711, 1688, 1593, 1371, 1271, 1206, 1194, 1182, 1173, 669, 583 cm$^{-1}$; $^1$H NMR (CDCl$_3$) δ7.88 (d, 1H, J=1.7 Hz), 7.82 (s, 1H), 7.61 (m, 1H), 7.58 (s, 1H), 7.3–7.1 (m, 8H), 5.63 (bs, 1H), 5.57 (bs, 1H), 4.21 (q, 2H, J=7.2 Hz), 2.38 (s, 3H), 1.27 (t, 3H, J=7.2 Hz). Elemental Analysis Calculated for C$_{27}$H$_{22}$Cl$_2$N$_2$O$_5$S: C, 58.18; H, 3.98; N, 5.03. Found: C, 57.22; H, 4.12; N, 4.93.

EXAMPLE 59

(E) and (Z)-2-(Phenyl)-3-(4,6-dichloroindol-3-yl-2-carboxylic acid)-propenoic acid amide

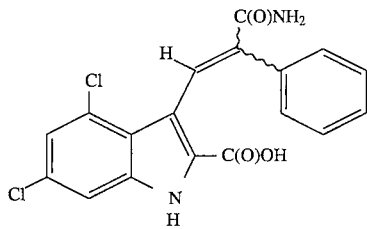

Prepare by the method of Example 30.1 using (E) and (Z)-2-(phenyl)-3-(2-carboethoxy-4,6-dichloroindol-3-yl)-propenoic acid amide (233 mg, 0.418 mmol) to give, after recrystallization from dichloromethane/ether, the title compound: mp 169° C. (dec); IR (KBr) νmax 3393, 3283, 1680, 1615, 1578, 1559, 1534, 1240 cm$^{-1}$; $^1$H NMR (DMSO-$_6$) δ13.24 (bs, 1H), 12.06 (s, 1H), 7.71 (s, 1H), 7.31 (d, 1H, J=1.7 Hz), 7.27 (bs, 1H), 7.1 (m, 4H), 6.9 (m, 3H). Elemental Analysis Calculated for C$_{18}$H$_{12}$Cl$_2$N$_2$O$_3$: C, 57.62; H, 3.22; N, 7.47. Found: C, 57.44; H, 3.80; N, 7.01.

EXAMPLE 60

(E) and (Z)-N-(2-Phenylethyl)-2-(phenyl)-3-(1-p-toluenesulfonyl-2-carboethoxy-4,6-dichloroindol-3-yl)propenoic acid amide Prepare by the method of Example 22.1 using (E) and (Z)-2-(phenyl)-3-(2-carboethoxy-4,6-dichloroindol-3-yl)-propenoic (1.08 g, 1.93 mmol) with phenethylamine to give, after recrystallization from ethyl acetate/cyclohexane, the title compound: mp 108°–112° C; IR (KBr) νmax 1730, 1514, 1371, 1269, 1194, 1181, 665, 581 cm$^{-1}$; $^1$H NMR (CDCl$_3$) δ7.87 (d, 1H, J=1.7 Hz), 7.75 (s, 1H), 7.59 (m, 1H), 7.57 (m, 1H), 7.3–7.1 (m, 11H), 7.0–6.9 (m, 2H), 5.56 (bt, 1H, J=5.6 Hz), 4.19 (q, 2H, J=7.2 Hz), 3.58 (q, 2H, J=6.5 Hz), 2.82 (t, 2H, J=6.8 Hz), 2.37 (s, 3H), 1.26 (t, H, J=7.2 Hz). Elemental Analysis Calculated for C$_{35}$H$_{30}$Cl$_2$N$_2$O$_5$S: C, 63.54; H, 4.57; N, 4.23. Found: C, 64.26; H, 4.74; N, 4.00.

EXAMPLE 61

(E) and (Z)-N-(2-Phenylethyl)-2-(phenyl)-3-(4,6-dichloroindol-3-yl-2-carboxylic acid)-propenoic acid amide

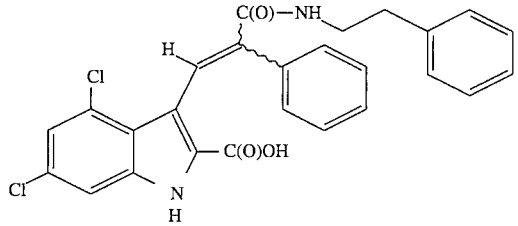

Prepare by the method of Example 30.1 using (E) and (Z)-N-(2-phenylethyl)-2-(phenyl)-3-(2-carboethoxy-4,6-dichloroindol-3-yl)-propenoic acid amide (0.87 g, 1.3 mmol) to give, after recrystallization from ethyl/cyclohexane, the title compound:: mp 195° C. (partial melt), 232° C. (dec); IR (KBr) νmax 3418, 1611, 1555, 1528, 1447, 1379, 1333, 1281, 700 cm$^{-1}$; $^1$NMR (DMSO-$_6$) δ12.43 (bs, 1H), 7.75 (s, 1H), 7.64 (bs, 1H), 7.4–7.2 (m, 6H), 6.97 (s, 5H), 6.84 (d, H, J=1.6 Hz), 3.43 (q, 2H, J=6.8 Hz), 2.81 (t, 2H, J=7.2 Hz). Elemental Analysis Calculated for C$_{26}$H$_{20}$Cl$_2$N$_2$O$_3$: C, 65.15; H, 4.21; N, 5.84. Found: C, 60.87; H, 4.12; N, 5.24.

EXAMPLE 62

(E) and (Z)-2-(Phenyl)-3-(2-carboethoxy-4,6-dichloroindol-3-yl)-propenonitrile

Combine 3-formyl-2-carboethoxy-4,6-dichloroindole (1.43 g, 5.0 mmol), phenylacetonitrile (0.59 g, 0.60 mL, 5.0 mmol), piperidine (4 drops), and ethanol (30 mL). Heat to reflux. After 16 hours, cool to ambient temperature. Cool to ambient temperature, dilute with ether to give a solid. Collect the solid by filtration, rinse with ether, and recrystallize from acetone/water to give the title compound: mp 215°–217° C. (dec); IR (KBr) νmax 3350, 3086, 3059, 3034, 2986, 2939, 2904, 2222, 1730, 1685, 1606, 1558, 1531, 1496, 1475, 1448, 1438, 1421, 1388, 1367, 1342, 1321, 1303, 1230, 1172, 1116, 1078, 1020, 983, 914, 848, 841, 810, 788, 763, 744, 688, 663, 653, 632, 613, 592, 536 cm$^{-1}$; $^1$H NMR (DMSO-$_6$) δ12.81 (s, 1H),
8.33 (s, 1H), 7.76 (d, 2H, J=7.0 Hz), 7.52 (m, 4H), 7.35 (s, 1H), 4.34 (q, 2H, J=6.7 Hz), 1.25 (t, 3H, J=6.8 Hz). Elemental Analysis Calculated for C$_{20}$H$_{14}$Cl$_2$N$_2$O$_2$: C, 62,35; H, 3.66; N, 7.27. Found: C, 58.38; H, 3.48; N, 6.66.

EXAMPLE 63

(E) and (Z)-2-(Phenyl)-3-(4,6-dichloroindol-3-yl-2-carboethoxy)-propenoic acid amide

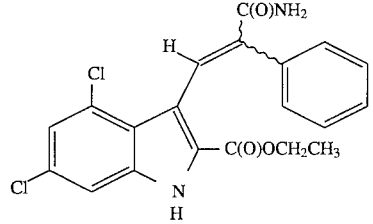

Combine (E) and (Z)-2-(phenyl)-3-(2-carboethoxy-4,6-dichloroindol-3-yl)-propenonitrile (225 mg, 0,584 mmol), sulfuric acid (3 mL), acetic acid (3 mL). Heat to about 70°

C. After 16 hours, cool to ambient temperature and pour the reaction mixture into ice-water to give a solid. Collect the solid by filtration, rinse with additional water and dry to give a residue. Recrystallize that residue from acetone/water to give the title compound: mp 267°–270° C (dec).

EXAMPLE 64

(E) and (Z)-2-(Phenyl)-3-(4,6-dichloroindol-3-yl-2-carboxylic acid)-propenoic acid amide

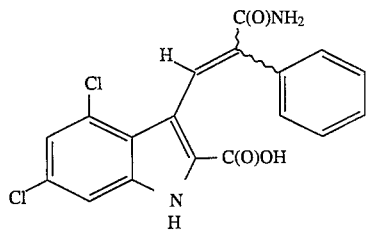

Prepare by the method of Example 30.1 using (E) and (Z)-2-(Phenyl)-3-(4,6-dichloroindol-3-yl-2-carboethoxy)-propenoic acid amide (202 mg, 0.50 mmol) to give the title compound: mp 169° C. (dec); IR (KBr) vmax 3393, 3283, 1680, 1615, 1578, 1559, 1534, 1240 cm$^{-1}$; $^1$H NMR (DMSO-$_6$) δ13.24 (bs, 1H), 12.06 (s, 1H), 7.71 (s, 1H), 7.31 (d, H, J=1.7 Hz), 7.27 (bs, 1H), 7.1 (m, 4H), 6.9 (m, 3H). Elemental Analysis Calculated for $C_{18}H_{12}Cl_2N_2O_3$: C, 57.62; H, 3.22; N, 7.47. Found: C, 57.44; H, 3.80; N, 7.01.

PREPARATION 7

3-Formyl-1-p-toluenesulfonyl-2-carboethoxy-4,6-dichloroindole

Combine 3-formyl-2-carboethoxy-4,6-dichloroindole (46.3 g. 162 mmol) and anhydrous potassium carbonate (44.9 g, 325 mmol) in dimethylformamide (600 mL). Add p-toluenesulfonyl chloride (42.9 g, 225 mmol). After 18 hours, pour the reaction mixture into water (3 L) and stir to give a solid. Filter, rinse with water and diethyl ether, and recrystallize from acetonitrile/dichloroethane to give the title compound: mp 189°–191° C. (dec); $R_f$=0.64 (silica gel, 1/1 ether/hexane); $^1$H NMR (CDCl$_3$) δ10.71 (s, 1H), 8.00 (m, 3H), 7.36 (m, 3H), 4.61 (q, 2H, J=7.2 Hz), 2.41 (s, 3H), 1.49 (t, 3H, J=7.1 Hz).

PREPARATION 8

3-Acetyl-1-p-toluenesulfonyl-2-carboethoxy-indole

Prepare by the method of Preparation 7 using 3-acetyl-2-carboethoxy-indole, Y. Murakami, et al., *Heterocycles* 22, 241–244 (1984) and Y. Murakami, et al., *Heterocycles* 14, 1941 (1980) and p-toluenesulfonyl chloride to give the title compound.

PREPARATION 9 t-Butyl diethylphosphonobromoacetate

Combine sodium hydroxide (65 g, 1.6 mol) and water (195 mL). Cool to −10° C. Add dropwise, bromine (42 mL, 0.81 mol) at such a rate that the temperature of the reaction does not rise above 0° C. Add t-butyl diethylphosphonoacetate (46.5 g, 184 mmol) at such a rate that the temperature of the reaction does not rise above 0° C. After 90 minutes, extract the reaction mixture three times with chloroform. Combine the organic layers and extract with waters dry over MgSO$_4$, filter, and evaporate in vacuo to give t-butyl diethylphosphonodibromoacetate: $R_f$=0.24 (silica gel, 1/1 ether/hexane); $^1$H NMR (CDCl$_3$) δ 4.31–4.24 (m, 5H), 1.51 (s, 9H), 1.40–1.35 (2 overlapping t, 6 H, J=7.0 Hz).

Combine t-butyl diethylphosphonodibromoacetate (75.6 g, 184 mmol) and isopropanol (190 mL). Cool to 0° C. Add a solution of tin (II) chloride (33.2 g, 175 mmol) in water (190 mL). After the addition is complete, warm to ambient temperature. After 1 hour, extract the reaction mixture three times with chloroform. Combine the organic layers and extract with water, dry over MgSO$_4$, filter, and evaporate in vacuo to give the title compound.

PREPARATION 10

(E) and (Z)-2-bromo-3-(1-p-toluenesulfonyl-2-carboethoxy-4,6-dichloroindol-3-yl)propenoic acid, t-butyl ester Combine t-butyl diethylphosphonobromoacetate (45.4 g, 137 mmol) and tetrahydrofuran (550 mL). Cool to −78° C. Add dropwise a solution of lithium bis(trimethylsilyl)amide (137 mL, 1.0M in tetrahydrofuran, 137 mmol). Add, portionwise over 30 minutes, 3-formyl-1-p-toluenesulfonyl-2-carboethoxy-4,6-dichloroindole (38.4 g, 87.2 mmol). After the addition is complete, warm to ambient temperature. After 18 hours, add water and evaporate in vacuo to remove the tetrahydrofuran. Extract with dichloromethane. Dry the organic layer over MgSO$_4$, filter, and evaporate in vacuo to give a residue. Recrystallize the powder from ethyl acetate/cyclohexane, filter, and dry to give the (Z)-isomer: mp 131°–132° C. $^1$H NMR (CDCl$_3$) δ8.21 (s, 1H), 7.95 (m, 3H), 7.30 (m, 3H), 4.42 (q, 2H, J=7.2 Hz), 2.41 (s, 3H), 1.56 (s, 9H), 1.36 (t, 3H, J=7.15 Hz). Elemental Analysis calculated for $C_{25}H_{24}BrCl_2NO_6S$: C, 48.64; H, 3.92; N, 2.26. Found: C, 48.44; H, 3.90; N, 2.22.

Chromatograph a mixture of (E) and (Z)-isomers on silica gel. Evaporate the early eluting fractions to give a residue enriched in the (E)-isomer. Recrystallize the residue from diethyl ether/pentane and cool to −20° C. to give the (E)-isomer: mp 117–119.5-C; $^1$H NMR (CDCl$_3$) δ7.99 (d, 1H, J=1.7 Hz), 7.96 (d, 2H, J=8.7 Hz), 7.50 (s, 1H), 7.33 (d, 2H, J=8.7 Hz), 7.27 (d, 1H, J=1.7 Hz), 4.42 (q, 2H, J=7.2 Hz), 2.42 (s, 3H), 1.39 (t, 3H, J=7.2 Hz), 1.00 (s, 9H).

PREPARATION 11

(Z)-2-bromo-3-methyl-3-(1-p-toluenesulfonyl-2-carboethoxy-indol-3-yl)propenoic acid, t-butyl ester Prepare by the method of Preparation 7 using 3-acetyl-1-p-toluenesulfonyl-2-carboethoxy-indole to give the title compound.

EXAMPLE 65

(E) and (Z)-2-Phenyl-3-(1-p-toluenesulfonyl-2-carboethoxy-4,6-dichloroindol-3-yl),propenoic acid, t-butyl ester

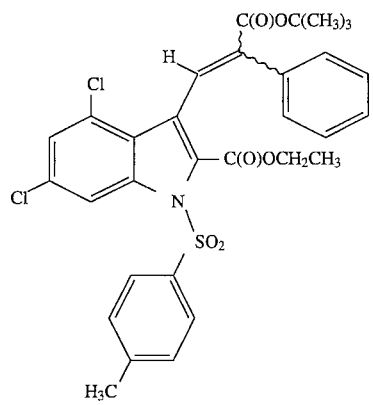

Combine (Z)-2-bromo-3-(1-p-toluenesulfonyl-2-carboethoxy-4,6-dichloroindol-3-yl)propenoic acid, t-butyl ester (6.0 g, 9.7 mmol) and toluene (110 mL). Add phenylboronic acid (1.8 g, 15 mmol: purify by suspension in water and heating at reflux for 2–3 h; concentrate in vacuo to give phenylboronic acid, substantially free of anhydride, which is used immediately without further purification), anhydrous potassium carbonate (2.7 g, 19 mmol), and tetrakis-triphenylphosphine palladium (0) (1.2 g, 1.0 mmol). Heat to 90°–100° C. After 3.5 hours, cool to ambient temperature. Concentrate in vacuo to give a residue. Combine the residue and dichloromethane and extract with with water, saturated aqueous sodium bicarbonate solution, saturated aqueous tartaric acid solution and water. Dry the organic layer over $MgSO_4$, filter, and concentrate in vacuo to give a residue. Chromatography on a short column of silica gel eluted with 3/1 cyclohexane/ether followed by chromatography on silica gel 15% ether in cyclohexane gave the title compound: $^1$H NMR ($CDCl_3$) δ7.90 (s, 1H), 7.81 (s, 1H), 7.62 (m, 2H), 7.26–7.02 (m, 8H), 4.12 (q, 2H, J=7.1 Hz), 2.39 (s, 3H), 1.53 (s, 9H), 1.24 (t, 3H, J=7.4 Hz). Anal. Calcd. for $C_{31}H_{29}Cl_2NO_6S$: C, 60.58; H, 4.76; N, 2.28. Found: C, 60.20; H, 4.77; N, 2.36.

EXAMPLE 66

(E) and (Z)-2-(4-Chlorophenyl )-3-(1-p-toluenesulfonyl-2-carboethoxy-4,6-dichloroindol-3-yl)-propenoic acid, t-butyl ester

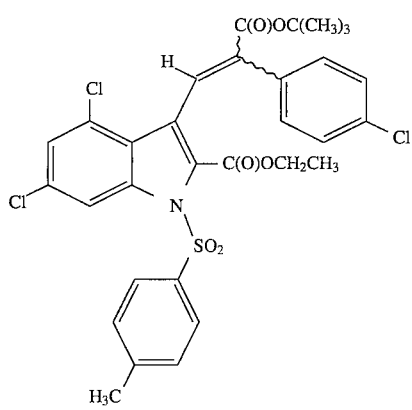

Prepare by the method of Example 65 using (Z)-2-bromo-3-(1-p-toluenesulfonyl-2-carboethoxy-4,6-dichloroindol-3-yl)propenoic acid, t-butyl ester (1.08 g, 1.75 mmol) and freshly hydrolyzed 4-chlorobenzeneboronic acid (0.41 g, 2.6 mmol) to give the title compound: $^1$H NMR ($CDCl_3$) δ7.93 (s, 1H), 7.84 (s, 1H), 7.60 (d, 2H, J=8.6 Hz), 7.26–7.23 (s overlapping d, 3H, J=9 Hz ), 7.07 (q, 4H, J=8.4 Hz ), 4.16 (q, 2H, J=7.2 Hz), 2.39 (s, 3H), 1.52 (s, 9H), 1.25 (t, 3H, J=7.2 Hz). Elemental Analysis Calculated for $C_{31}H_{28}Cl_3NO_6S$: C, 57.37; H, 4.35; N, 2.16. Found: C, 57.08; H, 4.43; N, 2.00.

EXAMPLE 67

(E) and (Z)-2-(4-chlorophenyl)-3(4,6-dichloroindol-3-yl-2-carboxylic acid-)-propenoic acid

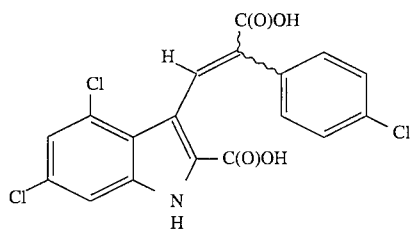

Combine (E) and (Z)-2-(4-chlorophenyl)-3-(1-p-toluendulfonyl-2-carboethoxy-4,6-dichloroindol-3-yl)-propenoic acid, t-butyl ester (213 mg, 0.328 mmol) and trifluoroacetic acid (1.0 mL) in dichloromethane (10 mL). After 45 minutes, dilute the reaction mixture with additional dichloromethane and extract with water. Separate the organic layer, dry over $MgSO_4$, and concentrate in vacuo to give a residue. Combine the residue, lithium hydroxide hydrate (34 mg, 0.81 mmol) and 1/1 tetrahydrofuran/water (10 mL). Heat at reflux. After 16 hours, evaporate the tetrahydrofuran in vacuo, dilute with additional water and acidify with aqueous potassium bisulfate. Extract with ethyl acetate. Extract the organic layer with water, separate, dry over $MgSO_4$, and concentrate in vacuo to give a residue. Recrystallize the residue from dichloromethane/methanol to give the title compound: mp 252°–254° C. (dec); $^1$H NMR (DMSO-$_6$) δ13.1 (bs, 1.5H), 12.2 (s, 1H), 8.11 (s, 1H), 7.34 (s, 1H), 7.17 (m, 3H), 6.97 (m, 2H).

EXAMPLE 68

(E) and (Z)-2-(4-Methoxyphenyl)-3-(1-p-toluenesulfonyl-2-carboethoxy-4,6-dichloroindol-3-yl)propenoic acid, t-butyl ester

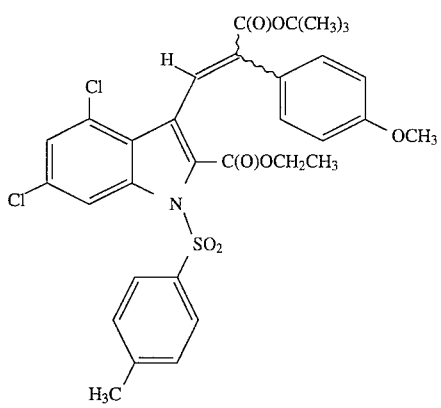

Combine (Z)-2-bromo-3-(1-p-toluenesulfonyl-2-carboethoxy-4,6-dichloroindol-3-yl)propenoic acid, t-butyl ester (623 mg, 1.01 mmol), toluene (50 mL), tris(dibenzylideneacetoneipalladium(0) (92.6 mg, 0.101 mmol), tri-2-furylphosphine (192 mg, 0.827 mmol) and powdered potassium carbonate (426 mg, 3.07 mmol). Add 4-methoxyphenylboronic acid (45 6 mg, 3.00 mmol (purified by suspension in water and heating at reflux for 2–3 hours; concentrate in vacuo to give 4-methoxyphenylboronic acid, substantially free of anhydride, which is used immediately without further purification). Heat to 55°–60° C. After 2 days, add 4-methoxyphenylboronic acid (480 mg, 3.16 mmol) and powdered potassium carbonate (42 4 mg, 3.07 mmol). After 6 days, cool to ambient temperature and filter through a short column of silica gel eluting with 3/1 cycloheaxane/ethyl acetate to give a residue. Chromatograph the residue on silica gel eluting with 3/1 cyclohexane/ether to give the title compound: $^1$H NMR (CDCl$_3$) δ7.91 (d, 1H, J=1.7 Hz), 7.75 (s, 1H), 7.63 (d, 2H, J=8.5 Hz), 7.24 (d, 1H, J=1.7 Hz), 7.21 (d, 2H, J=8.6 Hz), 6.98 (d, 2H, J=8.9 Hz), 6.64 (d, 2H, J=8.9 Hz), 4.15 (q, 2H, J=7.1 Hz), 3.74 (s, 3H), 2.37 (s, 3H), 1.53 (s, 9H), 1.23 (t, 3H, J=7.1 Hz).

EXAMPLE 69

(E) and (Z)-2-(4-Methoxyphenyl)-3-(4,6-dichloroindol-3-yl-2-carboxylic acid)propenoic acid

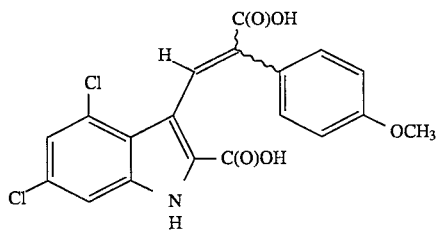

Combine (E) and (Z)-2-(4-methoxyphenyl)-3-(1-p-toluensulfonyl-2-carboethoxy-4,6-dichloroindol-3-yl)propenoic acid, t-butyl ester (427 mg) and 96% formic acid (6 mL). After 24 hours, evaporate in vacuo to obtain a residue and recrystallize that residue, if desired, from cyclohexane/ethyl acetate to obtain the intermediate (E) and (Z)-2-(4-methoxyphenyl)-3-(1-p-toluenesulfonyl-2-carboethoxy-4,6-dichloroindol-3-yl)propenoic acid: mp 175°–178° C.; IR (KBr) vmax 1728, 1692, 1371, 1271, 1250, 1179 cm$^{-1}$; $^1$H NMR (CDCl$_3$) δ8.01 (s, 1H), 7.92 (d, 1H, J=1.7 Hz), 7.63 (d, 2H, J=8.5 Hz), 7.26 (d, 1H, J=1.7 Hz), 7.22 (d, 2H, J=8.5 Hz), 7.01 (d, 2H, J=8.8 Hz), 6.67 (d, 2H, J=8.9 Hz), 4.16 (q, 2H, J=7.2 Hz), 3.76 (s, 3H), 2.38 (s, 3H), 1.24 (t, 3H, J=7.2 Hz).

Combine the intermediate (E) and (Z)-2-(4-Methoxyphenyl)-3-(1-p-toluenesulfonyl-2-carboethoxy-4,6-dichloroindol-3-yl)propenoic acid (258 mg, 0,438 mmol), lithium hydroxide hydrate (62 mg, 1.5 mmol),and in 3/1 tetrahydrofuran/water (13 mL). Heat to reflux. After 4 hours add another portion of lithium hydroxide hydrate (11 mg, 0.26 mmol). After 6.5 hours, evaporate the tetrahydrofuran in vacuo, dilute with additional water and acidify with aqueous potassium bisulfate. Extract with ethyl acetate. Extract the organic layer with water, separate, dry over MgSO$_4$, and concentrate in vacuo to give a residue. Recrystallize the residue from cyclohexane/ethyl acetate and then cyclohexane/acetone to give the title compound: mp 252° C. (dec, began turning amber at 242° C.); IR (KBr) vmax 1690, 1611, 1248, 1177 cm$^{-1}$; $^1$H NMR (DMSO-$_6$) δ13.5–12.3 (2H), 12.14 (s, 1H), 7.99 (s, 1H), 7.33 (d, 1H, J=1.7 Hz), 7.14 (d, 1H, J=1.7 Hz), 6.89 (d, 2H, J=8.7 Hz), 6.65 (d, 2 H, J=8.7 Hz) 3.62 (s, 3H). Elemental Analysis Calculated for C$_{19}$H$_{13}$Cl$_2$NO$_5$: C, 56.18; H, 3.23; N, 3.45. Found: C, 55.58; H, 3.31; N, 3.30.

EXAMPLE 70

(E) and (Z)-2-(2,4-Dichlorophenyl)-3-(1-p-toluenesulfonyl-2-carboethoxy-4,6-dichloroindol-3-yl)-propenoic acid, t-butyl ester

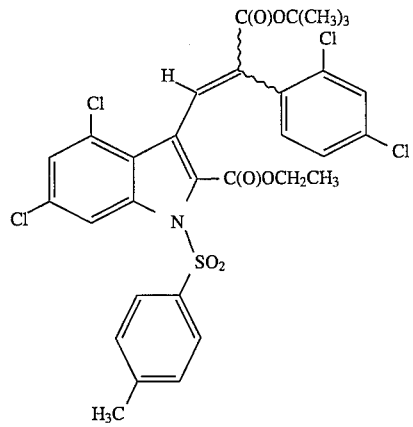

Prepare by the method of Example 65 using (Z)-2-bromo-3(1-p-toluenesulfonyl-2-carboethoxy-4,6-dichloroindol-3-yl)propenoic acid, t-butyl ester (1.08 g, 1.75 mmol) and freshly hydrolyzed 2,4-dichlorobenzeneboronic acid (0.41 g, 2.6 mmol) with heating at 90°–95° C. for 2.5 hours, then at 0° C. for 15 hours to give, after chromatography on silica gel eluting with 6/1 cyclohexane/ethyl acetate and recrystallization from cyclohexane, the title compound: mp 60.5°–163.5° C.; IR (KBr) vmax 1723, 1370, 1277, 1196, 1181, 1159, 579 cm$^{-1}$; $^1$H NMR (CDCl$_3$) δ7.94 (d, 1H, J=1.7 Hz), 7.91 (s, 1H), 7.62 (d, 2H, J=8.4 Hz), 7.35 (d, 1H, J=2.0 Hz), 7.28 (d, 1H, J=1.4 Hz), 7.23 (d, 2H, J=8.4 Hz), 6.86 (dd, 1H, J=8.3, 1.9 Hz), 6.75 (d, 1H, J=8.3 Hz), 4.26 (q, 2H, J=7.1 Hz), 2.40 (s, 3H), 1.49 (s, 9H), 1.28 (t, 3H, J=7.1 Hz). Elemental Analysis Calculated for C$_{31}$H$_{27}$Cl$_4$NO$_6$S: C, 54.48; H, 3.98; N, 2.05. Found: C, 54.21; H, 4.12; N, 1.96.

EXAMPLE 71

(E) and (Z)-2-(2,4-Dichlorophenyl)-3-(4,6-dichloroindol-3-yl-2-carboxylic acid-)-propenoic acid

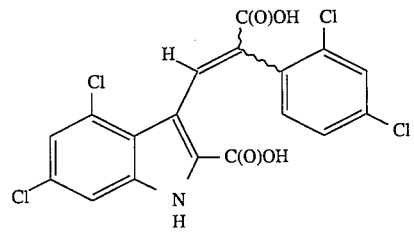

Prepare by the method of Example 69 using (E) and (Z)-2-(2,4-dichlorophenyl)-3-(1-p-toluenesulfonyl-2-carboethoxy-4,6-dichloroindol-3-yl)-propenoic acid, t-butyl ester (500 mg) to give, after recrystallization from cyclohexane/ethyl acetate, the title compound: mp 251° C. (dec); IR (KBr) vmax 1694, 1240, 1215 cm$^{-1}$; $^1$H NMR (DMSO-$_6$) δ12.9 (bs, 2H), 12.20 (s, 1H), 8.18 (s, 1H), 7.42 (d, 1H, J=2.2 Hz), 7.33 (d, 1H, J=1.8 Hz), 7.18 (d, 1H, J=1.8 Hz), 7.15 (dd, 1H, J=8.3, 2.2 Hz), 6.94 (d, 1H, J=8.3 Hz). Elemental Analysis Calculated for C$_{18}$H$_9$Cl$_4$NO$_4$: C, 48.57; H, 2.04; N, 3.15. Found: C, 48.28; H, 2.84; N, 2.81.

PREPARATION 12

1-Methoxy-1-trimethylsiloxy-2-phenyl-ethylene

Cool methyl phenylacetate (1.80 mL, 12.5 mmol) to 0° C. using and ice/water bath. Add dropwise and with vigorous stirring, a solution of trimethylsilyl triflate (2.70 mL, 4 mmol) and triethylamine (1.95 mL, 14 mmol) in dry ether (25 mL). When the addition is complete, warm slowly to ambient temperature. After 4.5 hours, cool in an ice/bath to obtain a heavier reddish oil. Remove the reddish oil by syringe. Evaporate the ether under high vacuum at 0° C. to obtain a residue and dissolve the residue in dichloromethane (25 mL) to give the title compound as a solution in dichloromethane which is used without further purification.

EXAMPLE 72

(E) and (Z)-2-Phenyl-3-(2-carboethoxy-4,6-dichloroindol-3-yl)-propenoic acid, methyl ester

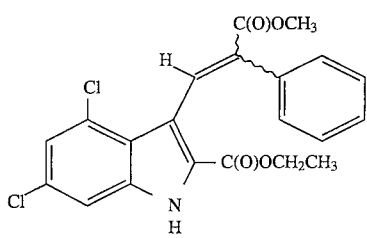

Combine triphenylphosphine oxide (556 mg, 2.00 mmol) and anhydrous dichloromethane (3 mL). Add dropwise a solution of trifluoromethanesulfonic anhydride (0.32 mL, 1.9 mmol) in anhydrous dichloromethane (1.5 mL). After 10 minutes, add another portion of triphenylphosphine oxide (556 mg, 2.00 mmol) to give a suspension. Cool to −78° C. the dichloromethane solution of 1-methoxy-1-trimethylsiloxy-2-phenyl-ethylene. Add 3-formyl-2-carboethoxy-4,6-dichloroindole (1.57 g, 5.49 mmol). Add 3.0 mL of the suspension obtained above. Warm to 0° C. over 1 hour. After 4 hours at 0° C., pour the reaction mixture into water and extract with ethyl acetate. Separate the organic layer and concentrate in vacuo to give a residue. Chromatograph the residue on silica gel eluting with 2.5/1 cyclohexane/ethyl acetate to give, in order of elution: threo-3-trimethylsilyloxy-2-phenyl-3-(2-carboethoxy-4,6-dichloroindol-3-yl)-propanoic acid, methyl ester as a white solid, erythro-3-hydroxy-2-phenyl-3-(2-carboethoxy-4,6-dichloroindol-3-yl)-propanoic acid, methyl ester, a mixture of erythro/threo-3-hydroxy-2-phenyl-3-(2-carboethoxy-4,6-dichloroindol-3-yl)-propanoic acid, methyl ester, and threo-3-hydroxy-2-phenyl-3-(2-carboethoxy-4,6-dichloroindol-3-yl)-propanoic acid, methyl ester.

Recrystallize threo-3-trimethylsilyloxy-2-phenyl-3-(2-caarboethoxy-4,6-dichloroindol-3-yl)-propanoic acid, methyl ester from cyclohexane to give a white solid: mp 150°–153° C.; IR (KBr) νmax 3329, 1730, 1688, 1238, 1167, 1080, 843 cm$^{-1}$; $^1$H NMR (CDCl$_3$) δ9.01 and 8.68 (major) (2s, 1H), 7.28 (d,< (2d, 1H, J=1.8 Hz), 7.07–6.95 (m, 5H), 6.76 and 6.62 (major) (2d, 1H, J=10.1 and 10.5 Hz), 4.93 and 4.72 (major) (2d, 1H, J=10.1 and 10.5 Hz), 4.54 and 4.41 and 4.37 (major) and 4.31 (major) and 4.28 (5q, 2H, J=7.1 Hz), 3.75 (major) and 3.74 (2s, 3H), 1.53 and 1.47 (major) (2t, 3H, J=7.1 Hz), −0.05 (major) and −0.07 (2s, 9H). Elemental Analysis Calculated for C$_{24}$H$_{27}$Cl$_2$NO$_5$Si: C, 56.69; H, 5.35; N, 2.75. Found: C, 56.72; H, 5.26; N, 2.75.

Recrystallize erythro/threo-3-hydroxy-2-phenyl-3-(2-carboethoxy-4,6-dichloroindol-3-yl)-propanoic acid, methyl ester from cyclohexane/ethyl acetate to give the erythro pair as a white solid: mp 206°–208° C.; IR (KBr) νmax 1740, 1686, 1246 cm$^{-1}$; $^1$H NMR (DMSO-$_6$) δ12.24 (bs, 1H), 7.49 (d, 1H, J=1.8 Hz), 7.48–7.25 (m, 5H), 7.29 (d, 1H, J=1.8 Hz), 6.44 (dd, 1H, J=9.9, 7.1 Hz), 5.24 (d, 1H, J=7.1 Hz), 4.56 (bs, 1H), 4.43 (q, 2H, J=7.1 Hz), 3.18 (s, 3H), 1.43 (t, 3H, J=7.1 Hz). Elemental Analysis Calculated for C$_{21}$H$_{19}$Cl$_2$NO$_5$S: C, 57.81; H, 4.39; N, 3.21. Found: C, 57.90; H, 4.43; N, 3.28. And the threo pair as a white solid: mp 177–178° C; IR (KBr) νmax 1736, 1723, 1686, 1310, 1244, 1167 cm$^{-1}$; $^1$H NMR (CDCl$_3$) δ8.99 (bs, 1 H), 7.15–7.10 ( m, 3H), 7.00 (m, 4H), 6.64 (dd, 1H, J=11.2, 10.1 Hz), 5.3 0 (bs, 1H), 4.50 (q, 2H, J=7.1 Hz), 4.38 (bd, 1H), 3.78 (s, 3H), 1.49 (t, 3H, J=7.1 Hz). Elemental Analysis Calculated C$_{21}$H$_{19}$Cl$_2$NO$_5$: C, 57.81; H, 4.39; N, 3.21. Found: C, 56.78; H, 4.35; N, 3.16.

Combine erythro/threo-3-hydroxy-2-phenyl-3-(2-carboethoxy-4,6-dichloroindol-3-yl)-propanoic acid, methyl ester from cyclohexane/ethyl acetate (232 mg, 0.532 mmol) and toluene (25 mL). Add p-toluenesulfonic acid (10 mg). Heat to reflux. After 2.5 hours, cool to ambient temperature. Extract the reaction mixture twice with water. Concentrate the organic layers in vacuo to give the title compound.

EXAMPLE 73

(E) and (Z)2-(3-Methoxyphenyl)-3-(2-carboethoxy-4,6-dichloroindol-3-yl)-propenoic acid, methyl ester

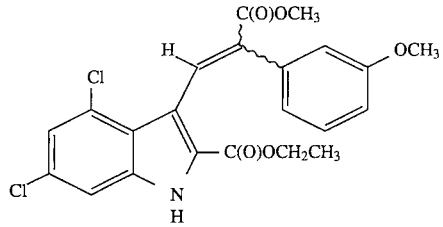

Prepare by the method of Example 72 using 3-formyl-2-carboethoxy-4,6-dichloroindole and 1-methoxy-1-trimethysiloxy-2-(3-methoxyphenyl)-ethylene prepared by the method of W. C. Lumma, Jr. and G. A. Berchtold, *J. Org. Chem.* 34, 1566–1572 (1969). Purify the aldol products by chromatography on silica gel eluting with 2/1 cyclohexane/ethyl acetate to give erythro/threo-3-hydroxy-2-(3-methoxyphenyl)-3-(2-carboethoxy-4,6-dichloroindol-3-yl)-propenoic acid, methyl ester and threo-3-hydroxy-2-(3-methoxyphenyl)-3-(2-carboethoxy-4,6-dichloroindol-3-yl)propanoic acid, methyl ester: mp 252° C. (dec); IR (KBr) νmax 3401, 1736, 1690, 1611, 1559, 1435, 1319, 1242, 1165 cm$^{-1}$; $^1$H NMR (CDCl$_3$) δ8.96 (bs, 1H), 7.13 (d, 1H, J=1.6 Hz), 7.03 (bs, 1H), 6.89 (t, 1H, J=8.0 Hz), 6.80 (bs, 1H), 6.67 (dd. 2H, J=11.3, 10.1 Hz), 6.54 (ddd, 1H, J=8.2, 2.5, 0.9 Hz), 5.26 (bs, 1H), 4.49 (q, 2H, J=7.1 Hz), 4.39 (m, 1H), 3.78 (s, 3H), 3.65 (s, 3H), 1.48 (t, 3H, J=7.1 Hz).

Combine erythro/threo-3-hydroxy-2-(3-methoxyphenyl)-3-(2-carboethoxy-4,6-dichloroindol-3-yl)-propanoic acid, methyl ester from cyclohexane/ethyl acetate and toluene (25 mL). Add p-toluenesulfonic acid (10 mg). Heat to reflux. After 2.5 hours, cool to ambient temperature. Extract the reaction mixture twice with water. Concentrate the organic layers in vacuo to give a residue. Chromatograph the residue on silica gel eluting with 4/1 cyclohexane/ethyl acetate to give the title compound: mp 137°–141° C. (partial melt), 147°–150° C. (clear melt); IR (KBr) νmax 3302, 1717, 1678, 1609, 1559, 1435, 1321, 1289, 1242, 1179 cm$^{-1}$; $^1$H NMR (CDCl$_3$) δ9.34 (bs, 1H-Z isomer), 9.15 (bs, 1H-E isomer), 8.18 (s, 1H-E isomer), 7.45 (s, 1H-Z isomer), 7.33 (t, 1H-Z isomer, J=0.9 Hz), 7.16 (d, 1H-E isomer, J=1.7 Hz), 7.1 (m, 2H-E isomer+2H-Z isomer), 7.01 (m, 1H-E isomer), 6.92 (m, 1H-Z isomer), 6.7–6.6 (m, 2H-E isomer+2 H-Z isomer), 4.34 (t, 2H-E isomer, J=7.1 Hz), 4.27 (t, 2H-Z isomer, J=7.1 Hz), 3.86 (s, 3H-E isomer), 3.85 (s, 3H-Z isomer), 3.59 (s, 3H-Z isomer), 3.54 (s, 3H-E isomer), 1.35 (t, 3H-E isomer, J=7.1 Hz), 1.32 (t, 3H-Z isomer, J=7.1 Hz).

EXAMPLE 74

(E) and (Z)-2-(3-Methoxyphenyl)-3-(2-carboethoxy-4,6-dichloroindol-3-yl-2-carboxylic acid)-propenoic acid

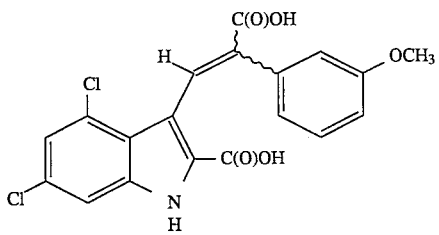

Prepare by the method of Example 3 to give, after chromatograph on silica gel eluting with 6% acetic acid in dichloromethane followed by recrystallization from acetone/water, the title compound: mp 269° C. (dec); IR (KBr) vmax 3414, 3405, 3352, 1690, 1613, 1559, 1289, 1248, 1215 cm$^{-1}$; $^1$H NMR (DMSO-$_6$) δ13.03 (bs, 2H), 12.15 (s, 1H), 8.05 (s, 1H), 7.33 (d, 1H, J=1.7 Hz), 7.16 (d, 1H, J=1.7 Hz), 7.00 (t, 1H, J=8.0 Hz), 6.64 (ddd, 1H, J=8.3, 2.6, 1.0 Hz), 6.6–6.5 (m, 2H), 3.52 (s, 3H). Elemental Analysis Calculated for $C_{19}H_{13}Cl_2NO_5S$: C, 56.18; H, 3.23; N, 3.45. Found: C, 55.87; H, 3.07; N, 3.23.

What is claimed is:

1. A compound of the formula:

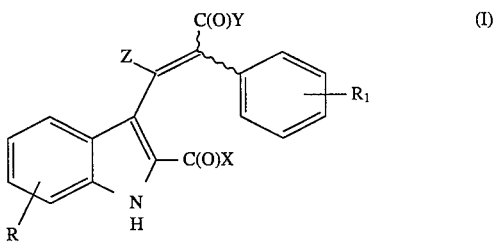

wherein

Z is hydrogen, —CH$_3$, or —C$_2$H$_5$;

X and Y are represented by —OH, a physiologically acceptable ester, or a physiologically acceptable amide;

R is represented by from 1 to 3 substituents independently chosen from the group: hydrogen, C$_{1-4}$ alkyl, C$_{1-4}$ alkoxy, halogen, —CF$_3$, or —OCF$_3$;

R$_1$ is represented by from 1 to 3 substituents independently chosen from the group: hydrogen, nitro, amino, C$_{1-4}$ alkyl, C$_{1-4}$ alkoxy, halogen, —CF$_3$, or —OCF$_3$;

or pharmaceutically acceptable addition salts thereof.

2. A compound of claim 1 wherein Z is hydrogen.
3. A compound of claim 2 wherein R is 4,6-dichloro.
4. A compound of claim 3 wherein X and Y are ethoxy.
5. A compound of claim 3 wherein X and Y are —OH.
6. A compound of claim 3 wherein X and Y are —NHCH$_3$.
7. A compound of claim 3 wherein X is —OH and Y is a physiologically acceptable amide.
8. A compound of claim 7 wherein X is —OH and Y is —NHPh.
9. A compound of claim 2 wherein R is 6-chloro.
10. A compound of claim 9 wherein X is —OH and Y is a physiologically acceptable amide.
11. A compound of claim 10 wherein X is —OH and Y is —NHPh.
12. A compound of claim 9 wherein X and Y are ethoxy.
13. A compound of claim 9 wherein X and Y are —OH.
14. A compound of claim 2 wherein R is 5,6-dichloro.
15. A compound of claim 14 wherein X and Y are ethoxy.
16. A compound of claim 14 wherein X and Y are —OH.
17. A compound of claim 1 wherein the compound is (E) or (Z)-2-Phenyl-3-(2-carboethoxy-4,6-dichloroindol-3-yl)propenoic acid, methyl ester or a mixture thereof.
18. A compound of claim 1 wherein the compound is (E) or (Z)-2-(3-Nitrophenyl)-3-(2-carboethoxy-4,6-dichloroindol-3-yl)-propenoic acid, methyl ester or a mixture thereof.
19. A compound of claim 1 wherein the compound is (E) or (Z)-2-(3-Aminophenyl)-3-(2-carboethoxy-4,6-dichloroindol-3-yl)-propenoic acid, methyl ester or a mixture thereof.
20. A compound of claim 1 wherein the compound is (E) or (Z)-2-(3-Aminophenyl)-3-(4,6-dichloroindol-3-yl-2-carboxylic acid)-propenoic acid or a mixture thereof.
21. A compound of claim 1 wherein the compound is (E) or (Z)-2-(4-Bromophenyl)-3-(2-carboethoxy-4,6-dichloroindol-3-yl)-propenoic acid, methyl ester or a mixture thereof.
22. A compound of claim 1 wherein the compound is (E) or (Z)-2-(4-Bromophenyl)-3-(4,6-dichloroindol-3-yl-2-carboxylic acid)-propenoic acid or a mixture thereof.
23. A compound of claim 1 wherein the compound is (E) or (Z)-2-(4-Aminophenyl)-3-(2-carboethoxy-4,6-dichloroindol-3-yl)-propenoic acid amide or a mixture thereof.
24. A compound of claim 1 wherein the compound is (E) or (Z)-2-(4-Methylphenyl)-3-(2-carboethoxy-4,6-dichloroindol-3-yl)-propenoic acid, methyl ester or a mixture thereof.
25. A compound of claim 1 wherein the compound is (E) or (Z)-2-(4-Methylphenyl)-3-(4,6-dichloroindol-3-yl-2-carboxylic acid)propenoic acid or a mixture thereof.
26. A compound of claim 1 wherein the compound is (E) or (Z)-2-Phenyl-3-(2-carboethoxy-4,6-dichloroindol-3-yl)propenoic acid, ethyl ester or a mixture thereof.
27. A compound of claim 1 wherein the compound is (E) or (Z)-2-Phenyl-3-(4,6-dichloroindol-3-yl-2-carboxylic acid)-propenoic acid or a mixture thereof.
28. A compound of claim 1 wherein the compound is (E) or (Z)-2-Phenyl-3-(5,6-dichloroindol-3-yl-2-carboxylic acid)-propenoic acid or a mixture thereof.
29. A compound of claim 1 wherein the compound is (E) or (Z)-2-Phenyl-3-(6-chloroindol-3-yl-2-carboxylic acid)propenoic acid or a mixture thereof.
30. A compound of claim 1 wherein the compound is (E) or (Z)-2-(4-Methoxyphenyl)-3-(4,6-dichloroindol-3-yl-2-carboxylic acid)propenoic acid or a mixture thereof.
31. A compound of claim 1 wherein the compound is (E) or (Z)-2-(4-Methylphenyl)-3-(2-carboethoxy-4,6-dichloroindol-3-yl)propenoic acid, ethyl ester or a mixture thereof.
32. A compound of claim 1 wherein the compound is (E) or (Z)-2-(4-Methylphenyl)-3-(2-carboethoxy-4,6-dichlorodindol-3-yl)propenoic acid, methyl ester or a mixture thereof.
33. A compound of claim 1 wherein the compound is (E) or (Z)-N-Methyl-2-phenyl-3-(4,6-dichloroindol-3-yl-2-carboxylic acid)propenoic amide or a mixture thereof.
34. A compound of claim 1 wherein the compound is (E) or (Z)-2-Phenyl-3-(2-carboethoxy-5,6-dichloroindol-3-yl)propenoic acid, ethyl ester or a mixture thereof.

35. A compound of claim 1 wherein the compound is (E) or (Z)-2-Phenyl-3-(2-carboethoxy-6-chloroindol-3-yl)propenoic acid, ethyl ester or a mixture thereof.

36. A compound of claim 1 wherein the compound is (E) or (Z)-2-Phenyl-3-(2-carboethoxy-4,6-dichloroindol-3-yl-)propenoic acid, t-butyl ester or a mixture thereof.

37. A compound of claim 1 wherein the compound is (E) or (Z)-N,N-Dimethyl-2-phenyl-3-(4,6-dichloroindol-3-yl-2-carboxylic acid)propenoic amide or a mixture thereof.

38. A compound of claim 1 wherein the compound is (E) or (Z)-N-Phenyl-2-phenyl-3-(4,6-dichloroindol-3-yl-2-carboxylic acid)propenoic amide or a mixture thereof.

39. A compound of claim 1 wherein the compound is (E) or (Z)-N-Benzyl-2-phenyl-3-(4,6-dichloroindol-3-yl-2-carboxylic acid)propenoic amide or a mixture thereof.

40. A compound of claim 1 wherein the compound is (E) or (Z)-N-Morphilino-2-phenyl-3-(4,6-dichloroindol-3-yl-2-carboxylic acid)propenoic amide or a mixture thereof.

41. A compound of claim 1 wherein the compound is (E) or (Z)-2-Phenyl-3-(2-carboethoxy-6-chloroindol-3-yl)propenoic acid, methyl ester or a mixture thereof.

42. A compound of claim 1 wherein the compound is (E) or (Z)-2-(4-Aminophenyl)-3-(4,6-dichloroindol-3-yl-2-carboxylic acid)-propenoic acid or a mixture thereof.

43. A compound of claim 1 wherein the compound is (E) or (Z)-2-(4-Iodophenyl)-3-(2-carboethoxy-4,6-dichloroindol-3-yl)-propenoic acid, methyl ester or a mixture thereof.

44. A compound of claim 1 wherein the compound is (E) or (Z)-2-(4-Iodophenyl)-3-(4,6-dichloroindol-3-yl-2-carboxylic acid)-propenoic acid or a mixture thereof.

45. A compound of claim 1 wherein the compound is (E) or (Z)-2-(4-Chlorophenyl)-3-(2-carboethoxy-4,6-dichloroindol- 3-yl)-propenoic acid, methyl ester or a mixture thereof.

46. A compound of claim 1 wherein the compound is (E) or (Z)-2-(4-Chlorophenyl)-3-(4,6-dichloroindol-3-yl-2-carboxylic acid)-propenoic acid or a mixture thereof.

47. A compound of claim 1 wherein the compound is (E) or (Z)-2-(4-Trifluoromethylphenyl)-3-(2-carboethoxy-4,6-dichloroindol-3-yl)-propenoic acid, methyl ester or a mixture thereof.

48. A compound of claim 1 wherein the compound is (E) or (Z)-2-(4-Trifluoromethylphenyl)-3-(4,6-dichloroindol-3-yl-2-carboxylic acid)-propenoic acid or a mixture thereof.

49. A compound of claim 1 wherein the compound is or (Z)-2-(2-Chlorophenyl)-3-(2-carboethoxy-4,6-dichloroindol-3-yl)-propenoic acid, methyl ester or a mixture thereof.

50. A compound of claim 1 wherein the compound is (E) or (Z)-2-(2-Chlorophenyl)-3-(4,6-dichloroindol-3-yl-2-carboxylic acid)-propenoic acid or a mixture thereof.

51. A compound of claim 1 wherein the compound is (E) or (Z)-2-(3-Nitrophenyl)-3-(4,6-dichloroindol-3-yl-2-carboxylic acid)-propenoic acid or a mixture thereof.

52. A compound of claim 1 wherein the compound is (E) or (Z)-2-(Phenyl)-3-(4,6-dichloroindol-3-yl-2-carboxylic acid)-propenoic acid amide or a mixture thereof.

53. A compound of claim 1 wherein the compound is (E) or (Z)-N-(2-Phenylethyl)-2-(phenyl)-3-(4,6-dichloroindol-3-yl-2-carboxylic acid)-propenoic acid amide or a mixture thereof.

54. A compound of claim 1 wherein the compound is (E) or (Z)-2-(Phenyl)-3-(4,6-dichloroindol-3-yl-2-carboethoxy)propenoic acid amide or a mixture thereof.

55. A compound of claim 1 wherein the compound is (E) or (Z)-2-(Phenyl)-3-(4,6-dichloroindol-3-yl-2-carboxylic acid)-propenoic acid amide or a mixture thereof.

56. A compound of claim 1 wherein the compound is (E) or (Z)-2-(4-Chlorophenyl)-3-(4,6-dichloroindol-3-yl-2-carboxylic acid-)-propenoic acid or a mixture thereof.

57. A compound of claim 1 wherein the compound is (E) or (Z)-2-(2,4-Dichlorophenyl)-3-(4,6-dichloroindol-3-yl-2-carboxylic acid-)-propenoic acid or a mixture thereof.

58. A compound of claim 1 wherein the compound is (E) or (Z)-2-(3-Methoxyphenyl)-3-(2-carboethoxy-4,6-dichloroindol-3-yl)-propenoic acid, methyl ester or a mixture thereof.

59. A compound of claim 1 wherein the compound is (E) or (Z)-2-(3-Methoxyphenyl)-3-(2-carboethoxy-4,6-dichloroindol-3-yl-2-carboxylic acid)-propenoic acid or a mixture thereof.

60. A method for antagonizing the effects of excitatory amino acids upon the NMDA receptor complex comprising administering to a patient in need thereof, an antagonistic amount of a compound according the claim 1.

61. A method for the treatment of neurodegenerative diseases comprising administering to a patient in need thereof an effective amount of a compound according to claim 1.

62. A method for preventing ischemic/hypoxic/hypoglycemic damage to cerebral tissue comprising administering to a patient in need thereof an effective amount of a compound according to claim 1.

63. A method for the treatment of anxiety comprising administering an anxiolytic amount of a compound according to claim 1.

64. A method for producing an analgesic effect comprising administering to a patient in need thereof an analgesic amount of a compound according to claim 1.

65. A pharmaceutical composition comprising an effective amount of a compound according to claim 1 in admixture with a pharmaceutically accepted carrier.

* * * * *

UNITED STATES PATENT AND TRADEMARK OFFICE
CERTIFICATE OF CORRECTION

PATENT NO.    :  5,519,048

DATED         :  May 21, 1996

INVENTOR(s)   :  Salituro et al.

It is certified that error appears in the above-identified patent and that said Letters Patent is hereby corrected as shown below:

Cover Page, Line 3 of Abstract, patent reads: " prpopenoic " and should read -- propenoic -- .
Column 3, Line 45, patent reads: " 6dichloroindol " and should read -- 6-dichloroindol -- .
Column 4, Line 18, patent reads: " propenoic " and should read -- propenoic acid -- .
Column 4, Line 38, patent reads: " y12- " and should read -- y1-2- --.
Column 4, Line 66, patent reads: " propenoic " and should read -- propenoic acid --.
Column 7, Line 62, patent reads: " be easily be " and should read -- easily be -- .
Column 8, line 26, patent reads: " pysiologically " and should read -- physiologically -- .
Column 8, Line 29, patent reads: " an suitable " and should read -- a suitable -- .
Column 10, Line 15, patent reads: " an vinyl " and should read -- a vinyl -- .
Column 10, Line 55, patent reads: " form " and should read -- from -- .
Column 18, Line 59, patent reads: " be easily be " and should read -- easily be -- .
Column 19, Line 25, patent reads: " an suitable " and should read -- a suitable -- .
Column 21, Line 7, patent reads: " as in well " and should read -- is well -- .
Column 23, Line 24, patent reads: " under lying " and should read -- underlying -- .
Column 25, Line 19, patent reads: " diehyl " and should read -- diethyl -- .
Column 28, Line 20, patent reads: " with ethyl dry the " and should read -- with ethyl acetate and dry the --.
Column 28, Line 43, patent reads: " ester ester " and should read -- ester -- .
Column 28, Line 44, patent reads: " 1g " and should read -- 1.1g -- .
Column 28, Line 47, patent reads: " 0§C " and should read -- 60°C-- .
Column 30, Line 9, patent reads: " -2, " and should read -- -2- -- .
Column 33, Line 25, patent reads: " -4-dichloroindol- " and should read -- -4, 6-dichloroindol- --.
Column 38, Line 41, patent reads: " form " and should read -- from -- .
Column 41, Line 35, patent reads: " C12 " and should read -- $Cl_2$ -- .
Column 43, Line 9, patent reads: " (CDC130) " and should read -- $(CDCl_3)$ -- .
Column 44, Line 30, patent reads: " 0,077 " and should read -- 0.077 --.
Column 44, Line 30, patent reads: " 0,117 " and should read -- 0.117 --.
Column 44, Line 40, patent reads: " dichloroindole (10.0 g, 0.039 " and should read -- dichloroindole -- .
Column 45, Line 5, patent reads: " -2, " and should read -- -2- -- .
Column 45, Line 41, patent reads: " $C_{21}H_{16}C_{12}N_2O_6$: C, 54.44; 3.48; " and should read -- $C_{21}H_{16}Cl_2N_2O_6$: C, 54.44; H, 3.48; -- .

UNITED STATES PATENT AND TRADEMARK OFFICE
CERTIFICATE OF CORRECTION

PATENT NO. : 5,519,048

DATED : May 21, 1996

INVENTOR(s) : Salituro et al.

It is certified that error appears in the above-identified patent and that said Letters Patent is hereby corrected as shown below:

Column 45, Line 50, patent reads: " $C_{21}H_{16}C_{12}N_2O_6$: " and should read -- $C_{21}H_{16}Cl_2N_2O_6$: --.

Column 45, Line 51, patent reads: " 5 4.55 " and should read -- 54.55 --.

Column 45, Line 56, patent reads: " -3yl " and should read -- -3-yl --.

Column 46, Line 63, patent reads: " $^1H(DMSO-_6)$ " and should read -- $^1H$ NMR (DMSO-$d_6$)--.

Column 46, Line 65, patent reads: " 6.2 7 " and should read -- 6.27 --.

Column 46, Line 67, patent reads: " $C_{18}H_{12}C_{12}N_2O_4$ " and should read -- $C_{18}H_{12}Cl_2N_2O_4$ --.

Column 47, Line 1, patent reads: " $H_{20}$ " and should read -- $H_2O$ --. line 18 of the Column 47, Line 26, patent reads: " Bromophenyl),3- " and should read -- Bromopheynyl)-3- --.

Column 48, Line 3, patent reads: " (DMSO-$_6$) " and should read -- (DMSO-$d_6$) -- : Column 48, Line 56, patent reads: " evaporate vacuo " and should read -- evaporate in vacuo --.

Column 49, Line 20, patent reads: " Adjust te " and should read -- Adjust the -- .

Column 50, Line 55, patent reads: " (DMSO-$_6$) " and should read -- (DMSO-$d_6$) -- .

Column 51, Line 1, patent reads: " H10 " and should read -- $H_{10}$ -- .

Column 51, Line 56, patent reads: " (DMSO-$_6$) " and should read -- (DMSO-$d_6$) --.

Column 52, Line 55, patent reads: " (DMSO-$_6$) " and should read -- (DMSO-$d_6$) -- .

Column 53, Line 6, patent reads: " $C(O)OCH_2CH_3$ " and should read -- $C(O)OCH_3$ --. Column 53, Line 44, patent reads: " after after " and should read -- after -- .

Column 53, Line 46, patent reads: " (DMSO-$_6$) " and should read -- (DMSO-$d_6$) --..

Column 54, Line 11, patent reads: " (m, H) " and should read -- (m, 6H), -- .

Column 54, Line 38, patent reads: " 1792, " and should read -- 792, --. Column 54, Line 45, patent reads: " , 3-(4,6-dichloroindoindol " and should read -- -3-(4,6-dichloroindol --.

Column 55, Line 7, patent reads: " propenoic " and should read -- propenoic acid --.

Column 55, Line 38, patent reads: " ether,the " and should read -- ether, the -- .

UNITED STATES PATENT AND TRADEMARK OFFICE
CERTIFICATE OF CORRECTION

PATENT NO. : 5,519,048

DATED : May 21, 1996

INVENTOR(s) : Salituro et al.

It is certified that error appears in the above-identified patent and that said Letters Patent is hereby corrected as shown below:

Column 55, Line 41, patent reads " (DMSO-6) and should read -- (DMSO-d6) --.

Column 55, Line 64, patent reads: " 1.26 (t, H, " and should read -- 1.26 (t, 3H, -- .

Column 56, Line 21, patent reads: " $^1$NMR (DMSO-$_6$) " and should read -- $^1$H NMR (DMSO-d$_6$) --. Column 56, Line 23, patent reads: " H, " and should read -- 1H, -- .

Column 56, Line 44, patent reads: " (DMSO-$_6$) " and should read -- (DMSO-d$_6$) --.

Column 56, Line 66, patent reads: " 0,584 " and should read -- 0.584 -- .

Column 57, Line 26, patent reads: " (DMSO-$_6$) " and should read -- (DMSO-d$_6$) -- .

Column 59, Line 32, patent reads: " with with " and should read -- with -- .

Column 60, Line 11, patent reads: " -3( " and should read -- -3-( -- .

Column 60, Line 25, patent reads: " toluendulfonyl " and should read -- toluenesulfonyl -- .

Column 60, Line 41, patent reads: " (DMSO-$_6$) " and should read -- (DMSO-d$_6$) -- .

Column 61, Line 4, patent reads: " 45 6 " and should read -- 456 -- .

Column 61, Line 9, patent reads: " 42 4 " and should read -- 424 -- .

Column 61, Line 12, patent reads: " 3/1cyclohexane " and should read -- 3/1 cyclohexane--.

Column 61, Line 50, patent reads: " 0,438 " and should read -- 0.438 -- .

Column 61, Line 62, patent reads: " (DMSO-$_6$) " and should read -- (DMSO-d$_6$) --.

Column 62, Line 29, patent reads: " 0°C " and should read -- 70°C -- .

Column 62, Line 32, patent reads: " 60.5° " and should read -- 160.5° --.

Column 62, Line 61, patent reads: " (DMSO-$_6$) " and should read -- (DMSO-d$_6$) -- .

Column 63, Line 53, patent reads: " caarboethoxy " and should read -- carboethoxy -- . Column 63, Line 57, patent reads: " (d,< (2d,1H " and should read -- (d, < 1H -- .

Column 63, Line 57, patent reads: " J=1.8 Hz), 7.07 " and should read -- J=1.8 Hz), 7.25-7.2 (m, << 1H), 7.18 (major) and 7.14 (2d, 1H, J=1.8 Hz), 7.07 -- .

Column 64, Line 3, patent reads: " (DMSO-$_6$) " and should read -- (DMSO-d$_6$) -- .

Column 64, Line 8, patent reads: " NO$_5$S: " and should read -- NO$_5$: .

UNITED STATES PATENT AND TRADEMARK OFFICE
CERTIFICATE OF CORRECTION

PATENT NO. : 5,519,048

DATED : May 21, 1996

INVENTOR(s) : Salituro et al.

It is certified that error appears in the above-identified patent and that said Letters Patent is hereby corrected as shown below:

Column 64, Line 13, patent reads: " 5.3 0 " and should read -- 5.30 -- .

Column 64, Line 26, patent reads: " (Z)2 " and should read -- (Z)-2 -- .

Column 65, Line 28, patent reads: " (DMSO-$_6$) " and should read -- (DMSO-d$_6$) -- .

Column 65, Line 32, patent reads: " NO$_5$S: " and should read -- NO$_5$: -- as found on page 121, line 23 of the specification.

Column 66, Line 60, patent reads: " dichlorodindol " and should read -- dichloroindol --

Column 67, Line 45, patent reads: " is or " and should read -- is (E) or -- .

Signed and Sealed this

Twenty-first Day of October 1997

Attest:

BRUCE LEHMAN

Attesting Officer

Commissioner of Patents and Trademarks